United States Patent
Chazenbalk

(10) Patent No.: US 11,913,027 B2
(45) Date of Patent: *Feb. 27, 2024

(54) METHODS OF TREATMENT USING PLURIPOTENT HUMAN ADIPOSE ADULT STEM CELLS

(71) Applicant: THE REGENTS OF THE UNIVERSITY OF CALIFORNIA, Oakland, CA (US)

(72) Inventor: Gregorio Chazenbalk, Studio City, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 54 days.

This patent is subject to a terminal disclaimer.

(21) Appl. No.: 17/305,483

(22) Filed: Jul. 8, 2021

(65) Prior Publication Data

US 2021/0403872 A1 Dec. 30, 2021

Related U.S. Application Data

(60) Continuation of application No. 16/179,798, filed on Nov. 2, 2018, now Pat. No. 11,066,647, which is a division of application No. 14/893,014, filed as application No. PCT/US2014/039137 on May 22, 2014, now Pat. No. 10,131,880.

(60) Provisional application No. 61/826,417, filed on May 22, 2013.

(51) Int. Cl.
*C12N 5/0775* (2010.01)
*A61K 35/28* (2015.01)
*C12N 5/074* (2010.01)

(52) U.S. Cl.
CPC ............ *C12N 5/0667* (2013.01); *A61K 35/28* (2013.01); *C12N 5/0607* (2013.01); *C12N 2500/02* (2013.01); *C12N 2501/734* (2013.01); *C12N 2506/1384* (2013.01)

(58) Field of Classification Search
CPC .............................. C12N 5/0667; A61K 35/28
See application file for complete search history.

(56) References Cited

U.S. PATENT DOCUMENTS

| | | |
|---|---|---|
| 7,078,230 B2 | 7/2006 | Wilkinson et al. |
| 7,470,537 B2 | 12/2008 | Hedrick et al. |
| 8,119,398 B2 | 2/2012 | Sayre et al. |
| 2001/0033834 A1 | 10/2001 | Wilkinson et al. |
| 2005/0032218 A1 | 2/2005 | Gerlach |
| 2007/0110729 A1 | 5/2007 | Kang |
| 2009/0304644 A1 | 12/2009 | Hedrick et al. |
| 2009/0317367 A1 | 12/2009 | Chazenbalk et al. |
| 2010/0330047 A1 | 12/2010 | Valorani |
| 2011/0020930 A1 | 1/2011 | Wise et al. |
| 2011/0070647 A1 | 3/2011 | Dezawa et al. |
| 2012/0028933 A1 | 2/2012 | Baust et al. |
| 2012/0244129 A1 | 9/2012 | Dezawa et al. |
| 2015/0258145 A1 | 9/2015 | Crawford et al. |

FOREIGN PATENT DOCUMENTS

| | | |
|---|---|---|
| EP | 2333049 A1 | 6/2011 |
| WO | WO2010069008 A1 | 6/2010 |
| WO | WO2011072461 A1 | 6/2011 |
| WO | WO2012133942 A1 | 10/2012 |

OTHER PUBLICATIONS

Aoki et al., "Generation of Induced Pluripotent Stem cells from Human Adipose-Derived Stem cells Without c-MYC", Tissue Engineering: Part A, 2010, vol. 16, No. 7, pp. 2197-2206 (Year: 2010).*
Gimble et al., "Adipose-Derived Stem Cells for Regenerative Medicine", Circulation Research, 2007, vol. 100, pp. 1249-1260. (Year: 2007).*
Safford et al., "Stem cell Therapy for Neurologic Disorders: Therapeutic Potential of Adipose-Derived Stem Cells", Current Drug Targets, 2005, vol. 6, pp. 57-62. (Year: 2005).*
Baer, Patrick C. et al. "Adipose-DerivedMesenchymal Stromal/Stem Cells: Tissue Localization, Characterization, and Heterogeneity" Stem Cells International, vol. 2012, Article ID 812693, 11 pages.
Baglioni, Silvana et al. "Characterization of human adult stem-cell populations isolated from visceral and subcutaneous adipose tissue" The FASEB Journal, Oct. 2009, vol. 23:3494-3505.
Kuroda, Yasumasa et al. "Unique multipotent cells in adult human mesenchymal cell populations" PNAS, May 11, 2010, 107(19):8639-8643.
Kuroda, Yasumasa et al. "Mesenchymal Stem Cells and Their Subpopulation, Pluripotent Muse Cells, in Basic Research and Regenerative Medicine" The Anatomical Record, 2014, 297:98-110.
Locke, Michelle et al. "Human adipose-derived stem cells: isolation, characterization and applications in surgery" ANZ J Surg, 2009, 79:235-244.
Riekstina, Una et al. "Embryonic Stem Cell Marker Expression Pattern in Human Mesenchymal Stem Cells Derived from Bone Marrow, Adipose Tissue, Heart and Dermis" Stem Cell Reviews, 2009, 5(4):378-386.

(Continued)

*Primary Examiner* — Laura Schuberg
(74) *Attorney, Agent, or Firm* — Karen S. Canady; canady + lortz LLP

(57) ABSTRACT

Methods for the efficient isolation and use of pluripotent adipose-derived stem cells (PASCs) are provided. In certain embodiments the methods involve providing an adipose tissue sample from which the stromal vascular fraction is co-cultured with the adipocyte fraction. PASCs can be isolated with a high degree of purification without requiring an additional cell enrichment process (e.g. cell sorting). PASCs and their conditioned media can be used for tissue regeneration within hours of harvesting the adipose tissue, and without requiring cell expansion. PASCs can grow as floating individual cells, as clusters of cells, or attached to surface(s) of the culture vessel. PASCs do not produce teratomas in vivo, nor do they induce immunorejection upon transplantation, and they achieve a high efficiency in grafting. The cells and compositions can be used for cell therapy and to screen new drugs.

19 Claims, 24 Drawing Sheets

(56) References Cited

OTHER PUBLICATIONS

Schaffler, Andreas et al. "Concise Review: Adipose Tissue-Derived Stromal Cells-Basic and Clinical Implications for Novel Cell-Based Therapies" Stem Cells, 2007, 25:818-827.

Wakao, Shohei, et al. "Multilineage-differentiating stress-enduring (Muse) cells are a primary source of induced pluripotent stem cells in human fibroblasts" PNAS, Jun. 14, 2011, 108(24):9875-9880.

Wilson, A. et al. "Adipose-derived stem cells for clinical applications: a review" Cell Proliferation, 2011, 44:86-98.

International Search Report and Written Opinion dated Oct. 27, 2014 from corresponding International Application PCT/US14/39137 filed May 22, 2013 (WO2014190150).

Machine translation of Publication WO2012133942 dated Oct. 14, 2012 (International Application PCT/JP2012/059422 filed Mar. 30, 2012) "Pluripotent stem cell capable of being isolated from fat tissue or umbilical cord of biological body".

Blaber et al., "Analysis of in vitro secretion profiles from adipose-derived cell populations", Journal of Translational Medicine, 2012, 10:172-, pp. 1-16.

Chazenbalk et al., "Novel Pathway of Adipogenesis through Cross-Talk between Adipose Tissue Macrophages, Adipose Stem cells and Adipocytes: Evidence of Cell Plasticity", PLoS, 2011, vol. 6, No. 3, e17834, pp. 1-8.

Schwarz et al., "Effects of different media on proliferation and differentiation capacity of canine, equine and porcine adipose derived stem cells", Research in Veterinary Science, 2011, vol. 93, pp. 457-462.

Lumeng et al "Macrophages block insulin action in adipocytes by altering expression of signaling and glucose transport proteins", American Journal Physiology, Endocrinology and Metabolism, 2007, vol. 292, No. 1, pp. E166-E174, pp. 1-23.

Carraro et al., "Islets of preadicpocytes highly committed to differentiation in cultures of adherent rat adipocytes. Light- and electron-microscopic observations", Cell and Tissue Research, 1991, vol. 264, No. 2, pp. 243-251.

Miyagi et al., "Application of Hypothermia to Autologous Stem Cell Purging", Cryobiology, 2001, vol. 42, pp. 190-195.

Heneidi, Saleh et al., "Awakened by cellular stress: isolation and characterization of a novel population of pluripotent stem cells derived from human adipose tissue." PLoS One. Jun. 5, 2013;8(6):e64752. doi: 10.1371/journal.pone.0064752. Print 2013.

Simerman, Ariel A. et al., "A mystery unraveled: nontumorigenic pluripotent stem cells in human adult tissues." Expert Opin Biol Ther. Jul. 2014;14(7):917-29. doi: 10.1517/14712598.2014.900538. Epub Apr. 19, 2014.

Extended European Search Report dated Oct. 13, 2016, from corresponding EP Patent Application No. 14801169.5.

\* cited by examiner

FIG. 7
Capacity of PASCs for self renewal
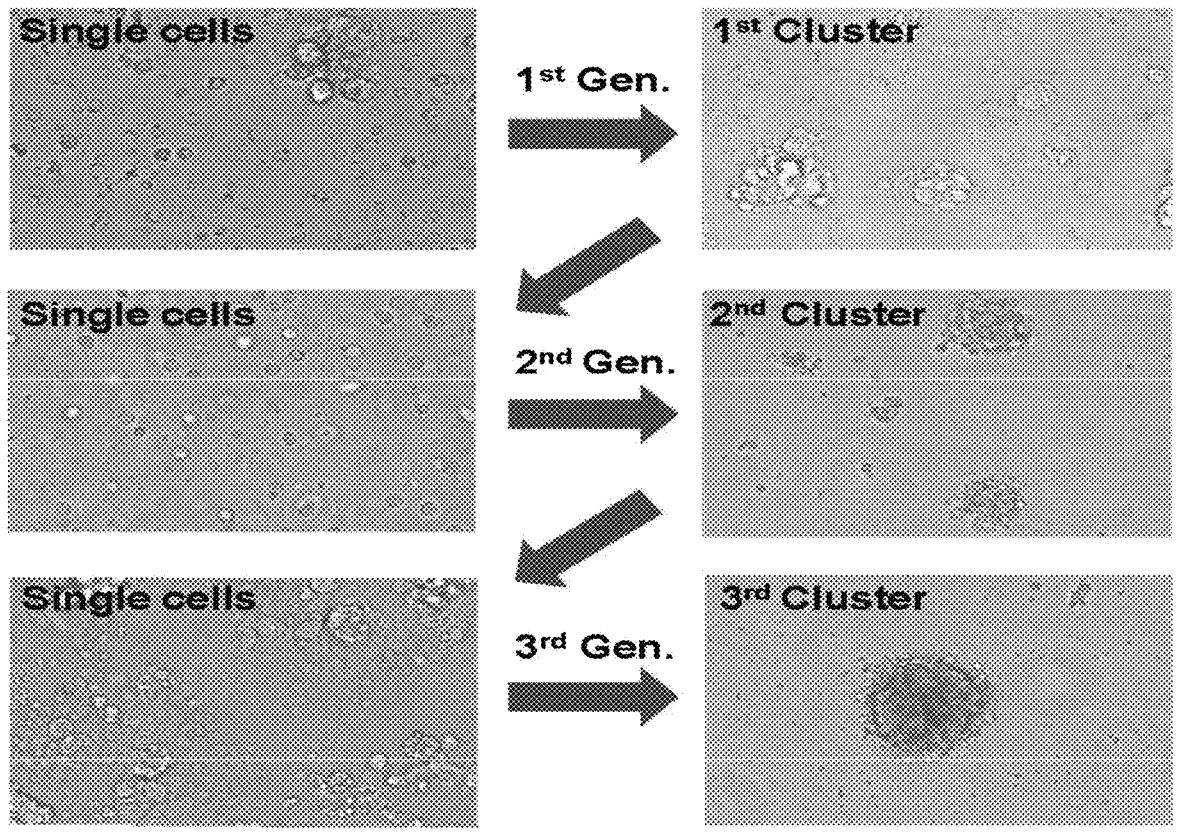
FIG. 8  PASCs have normal karyotype
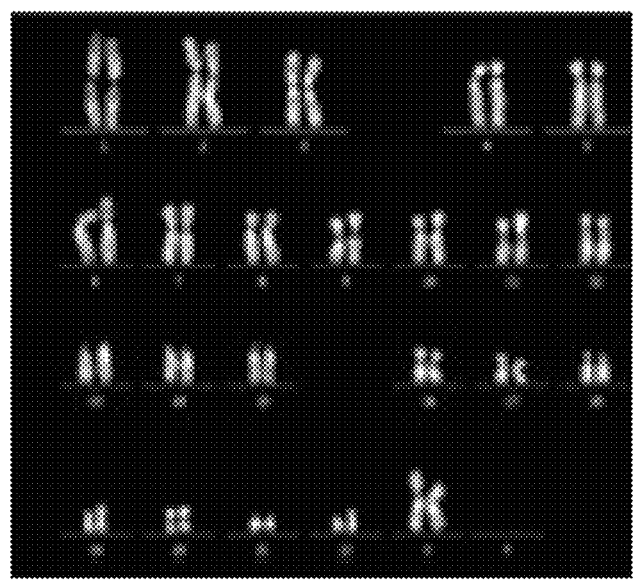

Mesenchymal Differentiation

FIG. 12A
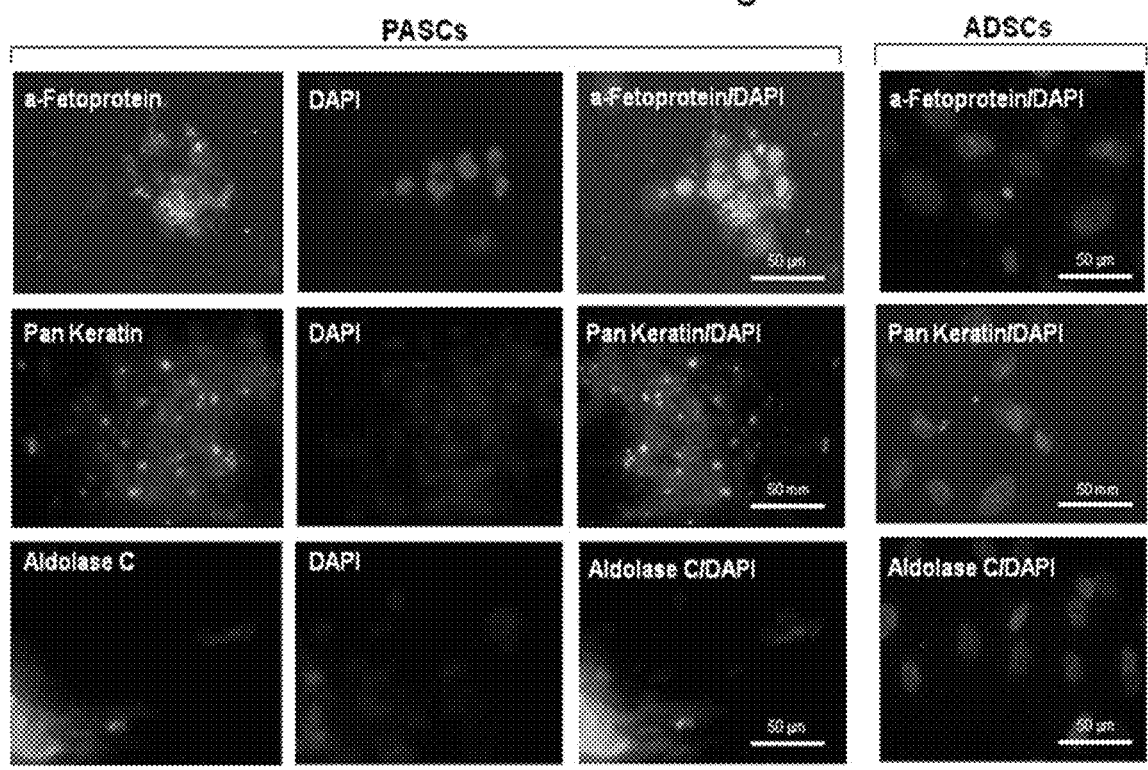
FIG. 12B Differentiation of PASCs to hepatocytes
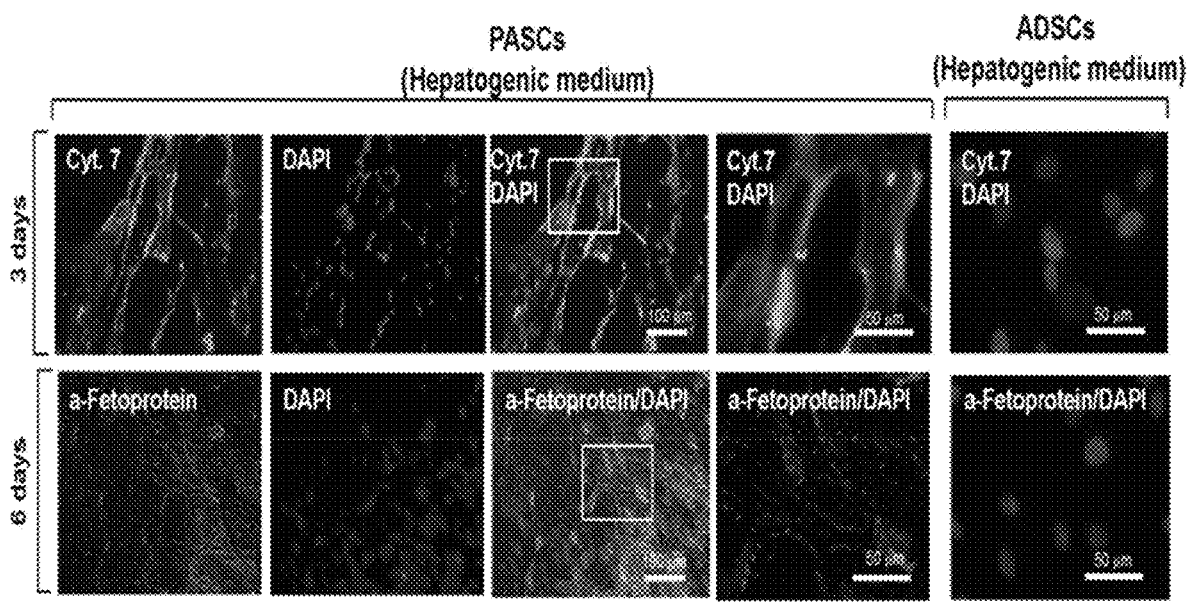

Differentiation of PASCs to neural cells in neural differentiation medium #2

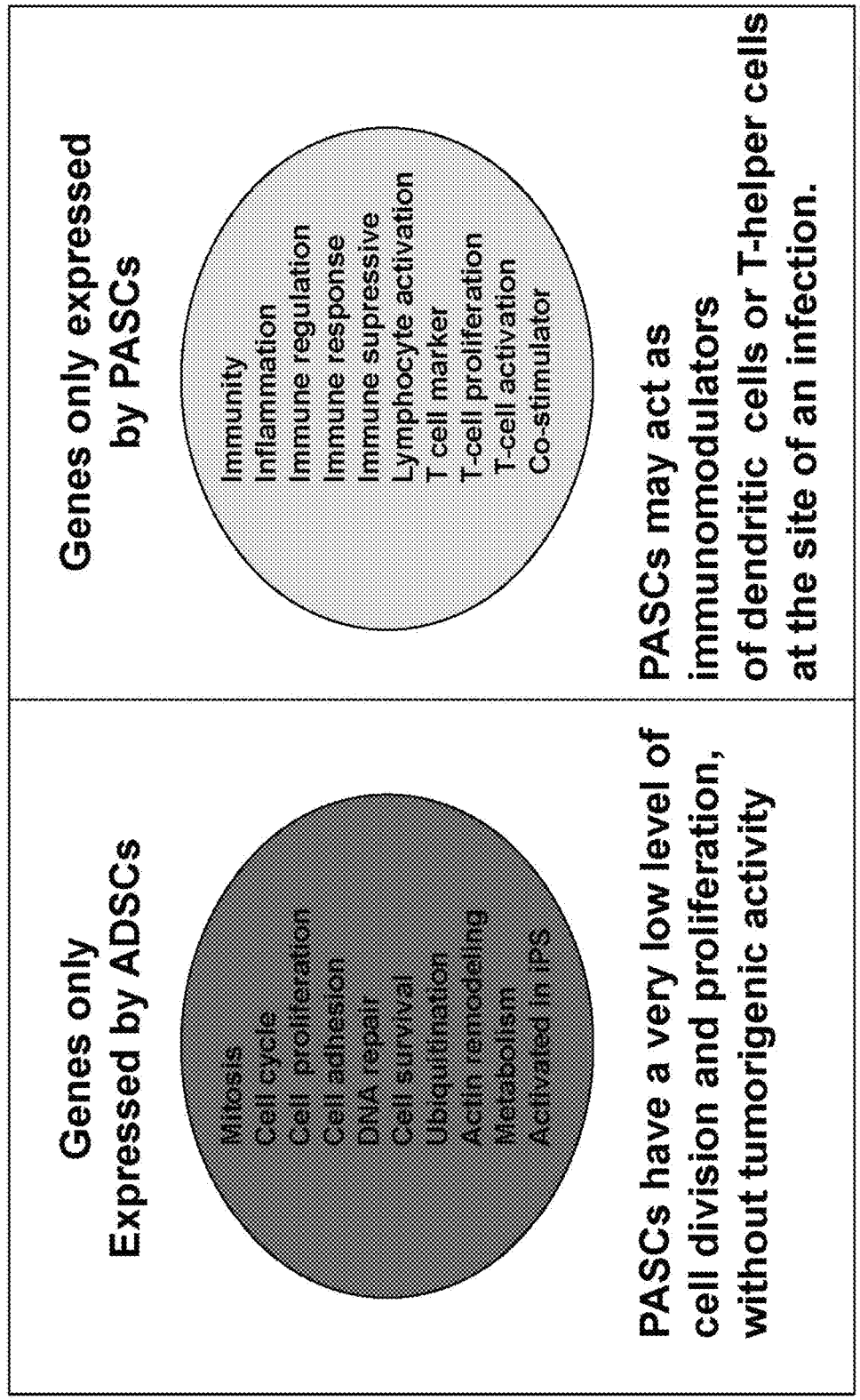

Effect of PASCs transplantation in diabetic mouse model

METHODS OF TREATMENT USING PLURIPOTENT HUMAN ADIPOSE ADULT STEM CELLS

This application is a continuation of U.S. patent application Ser. No. 16/179,798, filed Nov. 2, 2018, which is a divisional of U.S. patent application Ser. No. 14/893,014, filed Nov. 20, 2015, which is a national stage of PCT/US14/39137, filed May 22, 2014, which application claims priority to U.S. provisional patent application No. 61/826,417, filed May 22, 2013, the entire contents of which are incorporated herein by reference.

BACKGROUND

Pluripotent stem cells have the ability to differentiate into all types of cells (endodermal, ectodermal and mesodermal origin) and therefore have the potential to regenerate any kind of tissue with proper manipulation. Currently, two gold standard pluripotent stem cells are known, embryonic stem cells (ESCs) and induced pluripotent stem cells, which are reprogrammed adult somatic cells (iPSCs).

ES cells have unequivocally taken center stage in the field of stem cell research. ES cells exhibit the potential to treat a plethora of previously irreversible disorders through their capacity to generate tissues and thus to revolutionize regenerative medicine (1-3). However, evidence has since emerged that ES cells exhibit high rates of immunorejection upon transplantation and form teratomas as a result of their unbridled proliferation (4). In conjunction with debates surrounding the bioethical issues concerning the usage of human embryos, this teratogenic propensity precludes the practical application of ES cells in regenerative medicine.

Addressing the ethical dilemmas surrounding the use of ES cells for cell therapy, iPS cells became of interest in the stem cell field (5-6). iPS cells have the capacity to re-program, through an intricate mechanism involving the induction of the so-called "Yamanaka factors," including Nanog, Oct 3/4, Sox2, c-Myc and Klf4, which subsequently became the characteristic markers that establish pluripotency: the ability to self-renew and generate cells from the three germ lines and thus form teratomas (7-9). Though iPS cells resolve concerns of immunorejection because they can be generated from a patient's own, or autologous, cells, as well as the ethical issues that hinder the use of stem cells extracted from human embryos, the production of teratomas upon transplantation as a result of unbridled cell proliferation and extremely low survival rate of both iPS and ES cells upon reintroduction to the host organism, impede the translational use of these cells (10-12). Furthermore, it has also been found that mature iPS cells possess an epigenetic memory, defined by the remnants of posttranslational histone and DNA modifications, preventative of entirely successful reprogramming, often restricting their physiological function to that of a cell within the same lineage as the original stem cell source (13-15). Investigators have made attempts to address these issues, but to little avail (16-17). Despite excessive monetary and temporal efforts devoted to the study of both ES cells and iPS cells, there has been little progress made in overcoming the hurdles facing these stem cells and their use for cell therapy.

Other, non-reprogrammed pluripotent stem cell populations have caught the attention of the scientific community as an alternative to ethically contentious ES cells and genetically modified iPS cells. However, though multiple populations of adult stem cells have been put forth, many have faced a great deal of suspicion due to irreproducibility. Isolated from bone marrow, multipotent adult progenitor cells (MAPCs), both pluripotent and non-tumorigenic, were reported to contribute to chimeric offspring when injected into a mouse model and to regenerate damaged tissue in vivo (18-19). Human marrow-isolated adult multilineage inducible (MIAMI) cells and very small embryonic-like stem cells (VSELs), isolated from umbilical cord blood in addition to bone marrow, were soon to follow, exhibiting similar pluripotent and non-tumorigenic properties. Like VSELs, unrestricted somatic stem cells (USSCs), isolated from umbilical cord blood, are reportedly pluripotent but lack the classic pluripotent stem cell marker expression (20). These adult pluripotent stem cell lines have all been publically flagged for further investigation and reproduction, or in the case of VSELs, negated entirely. Stimulus-triggered acquisition of pluripotency (STAP), characterized by exposing splenic CD45+ lymphocytes to acidic conditions followed by incubation with leukaemia inhibitory factor (LIF), has recently been described as a method of bestowing pluripotency upon somatic cells (21). However, STAP cells form teratomas, hindering their clinical application. STAP cells are currently under investigation to determine the overall validity of the published results as well as the mechanism behind their reprogramming.

A population of human pluripotent stem cells with a high post-transplantation survival rate that does not undergo teratogenesis in vivo can facilitate treatment of many disorders affecting human beings. Recently, a group of researchers from Tohoku University, Japan, isolated and cultured a stem cell population isolated from skin and bone marrow with pluripotent characteristics (22-23). These cells named Muse cells (Differentiating Stress-Enduring Multilineage Cells) can be created in vitro under cellular stress conditions. Muse cells grow while forming cell clusters. Muse cells have been characterized as mesenchymal stem cells that have the ability to express a set of genes associated with pluripotency.

Furthermore, Muse cells can differentiate into endodermal, ectodermal, and mesodermal cells both in vitro and in vivo. More importantly, unlike ESCs and iPSCs, when Muse cells are transplanted (by local or i.v. injection) into immunodeficient mouse models for tissue regeneration, Muse cells integrate into damaged skin, muscle, or liver and regenerate new tissue. Muse cells do not undergo tumorigenic proliferation, and therefore would not be prone to produce teratomas in vivo, nor do induce immuno-rejection in the host upon autologous transplantation (22-23). Furthermore, in contrast to iPSCs, Muse cells do not require introduction of exogenous genes for their pluripotency. In addition, Muse cells are shown to home into the damage site in vivo and spontaneously differentiate into tissue specific cells according to the microenvironment to contribute to tissue regeneration when infused into blood stream (22).

Muse cells have the potential to make critical contributions to tissue regeneration, but are hindered due to difficulties associated with extraction of bone marrow stromal cells and human skin fibroblasts, and time-consuming purification methods including cell sorting, cell cloning by limiting dilution, long periods of cell culture which lead to a final production of only 1,000,000 Muse cells from of bone marrow stromal cells or human skin fibroblasts after SSEA3 cell sorting and one month of cell expansion. There thus remains a need for isolation of non-tumorigenic pluripotent cells as a source of tissue regeneration, and for improved methods of isolating such cells.

SUMMARY

Advances in stem cell therapy face major clinical limitations, particularly challenged by autologous transplantation of human pluripotent stem cells that does not undergo teratogenesis in vivo with a high post-transplantation survival rate. Hostile host factors of the engraftment microenvironment such as hypoxia, nutrition deprivation, pro-inflammatory cytokines, and reactive oxygen species can each contribute to unwanted differentiation or apoptosis. The invention addresses these needs and others by providing cells, methods and compositions for ameliorating tissue damage and disease, as well as for use in identifying, screening and testing new therapeutic agents.

In one embodiment, the invention provides a method of isolating pluripotent adipose stem cells (PASCs) from adipose tissue. The method typically comprises the steps of: (a) providing an adipose tissue sample; (b) subjecting cells in said sample to stress conditions; (c) co-culturing adipocytes and a stromal vascular fraction for 2-36 hours, typically for 6-8 hours; (d) recovering the viable cells; and (e) optionally culturing the recovered cells. In one embodiment, the stress conditions of step (b) comprise incubating the cells in a medium containing a proteolytic enzyme. The co-culturing of step (c) can be performed in the presence of a proteolytic enzyme as well. In a more specific embodiment, the enzyme is collagenase.

The stress conditions of step (b) include, but are not limited to, protease treatment, exposing cells to starvation conditions (no nutrients, no glucose), hypoxic conditions (lack of oxygen), low temperatures, heat shock, and lysis by mechanical procedures such as sonication. Two or more such stressors may be used together. Under these conditions, a highly purified population of PASCs is isolated without the need for time-consuming cell sorting methods, magnetic beads or special devices and prolonged cell culture procedures. The stress conditions are typically applied through the co-culturing step. For example, the cells obtained from adipose tissue are treated initially with protease (e.g., collagenase) for about 45 minutes at 37° C., followed by the stress conditions of step (b), in which the cells are exposed to hypoxic conditions at 4° C. for 2-8 hours (or overnight; step (c)), during which time the proteolytic activity is permitted to continue.

In a typical embodiment, the co-culturing is performed in the absence of serum. For example, the co-culturing can be performed in Dulbecco's Minimum Essential Medium (DMEM), or a similar basic medium known in the art. The co-culturing can be as simple as storing the cells in a 50 ml centrifuge tube. Stressors can be applied, for example, by closing the cap of the tube to create hypoxic conditions, placing the tube or other container into a refrigerator (cooling), as well as by using a nutrient-free medium (starvation).

In one embodiment, the co-culturing is performed for 4-24 hours. Typically, the co-culturing is performed for 6-8 hours (or overnight). The length of the co-culturing can be modified to accommodate timing considerations. For example, if isolated PASCs are required on an urgent basis, such as for treatment of traumatic injury, steps (b) and (c) can be shortened, and multiple stressors applied, to accelerate the process of selecting for stress-resistant cells.

In one embodiment, the recovering of step (d) comprises recovering at least 200,000 PASCs/ml of lipoaspirate material. This is equivalent to 200,000,000 PASCs retrieved with one liter of lipoaspirate material. In other embodiments, the recovering comprises recovering at least 50,000,000 PASCs, or at least 100,000,000 PASCs/lt of lipoaspirate material. These quantities of PASCs are typically recoverable within 6-8 hours (or overnight) of initiating the stress conditions of step (b). In some embodiments, at least 500,000,000 PASCs/liter of lipoaspirate are recovered within 8 hours of initiating the stress conditions of step (b). In other embodiments, the PASCs are recovered within 12-16 hours. In one embodiment, the method is performed without cell-sorting. In one embodiment, the recovering of viable cells comprises centrifuging the culture medium, removing the supernatant, washing the remaining cell pellet and resuspending the cell pellet in a buffer solution and/or culture medium. In some embodiments, the recovering of viable cells comprises providing red cell lysis buffer in the solution or culture medium containing the cells.

The invention further provides PASCs as described herein. The PASCs are typically present in a composition that is essentially free of other cell types (e.g., at least 95% pure, and in some embodiments, at least 99% pure). Also provided is a composition comprising PASCs isolated according to the method described herein, or progeny thereof, and a therapeutically acceptable culture medium. Also provided is a composition comprising conditioned medium that has been recovered from a culture of PASCs isolated in accordance with the methods described herein. Culture conditioned medium contains factors (cytokines, chemokines, growth factors, peptides, proteins) secreted by PASCs kept in culture for 24-72 hours. The conditioned medium is typically prepared from PASCs that have been cultured under standard conditions (e.g. DMEM, 10% fetal calf serum at 37C, 5% CO2). These factors released into the conditioned medium of PASCs have anti-inflammatory and/or immunomodulatory properties that can be used for treatment of disease, particularly immunological or autoimmune diseases.

In one embodiment, the composition comprises PASCs isolated from lipoaspiration. In one embodiment, the lipoaspiration is performed on the subject to whom the composition is administered. Both autologous and allogeneic transplantation of PASCs are contemplated. In a typical embodiment, the composition is administered to the subject within 6-24 hours of the lipoaspiration or less.

The invention additionally provides a method of ameliorating tissue damage in a subject. Typically, the method comprises administering a composition of the invention to the subject. Where the composition comprises PASCs, it may be administered under conditions permitting the PASCs of the composition to divide and to populate a site of tissue damage, although migration of PASCs to the site of damage is not required in all embodiments.

In some embodiments, the tissue damage comprises traumatic injury or disease-associated damage. Representative examples of traumatic injury comprises hypoxia, bone injury, laceration, and gunshot wound. In another embodiment, the disease-associated damage comprises damage associated with diabetes, vascular disease, infection, degenerative neurological disease, cancer, Huntington's Disease, Multiple Sclerosis, Rheumatoid Arthritis, Lupus, Diabetes type I, Crohn's disease.

BRIEF DESCRIPTION OF THE DRAWINGS

FIG. 7 indicates the capacity of PASCs for self-renewal. Expansion of PASCs in suspension only requires a gentle pipetting to disaggregate PASC clusters to single cells. These individual cells start forming clusters of cells. Once cell clusters are larger than 50 μm, the process of expansion is repeated again (third generation). PASCs have a low growth rate of 1-½ days/cell division.

FIG. 8 shows that PASCs isolated from lipoaspirate of normal woman show normal karyotype and 23 pairs of chromosomes including the sex chromosomes XX (female donor).

FIGS. 12A-12B show PASCs differentiation to endodermal cell lineages. (12A) Spontaneous differentiation of PASCs into a mesodermal lineage was determined using α-fetoprotein (a marker for development of endoderm and progenitors of hepatocytes) and pan keratin (marker for filaments characteristic of biliary tract epithelial cell) antibodies (12B) PASCs differentiation to hepatocyte like cells was determined in in hepatogenic differentiation medium (3 and 6 days) using and cytokeratin 7 (a marker for an intermediate filament protein in biliary cells) α-fetoprotein antibodies. ADSCs were used as negative controls.

FIG. 15 illustrates microarray analysis of functional group of genes that are expressed in PASCs and not in ADSCs, and vice versa. PASCs show very low expression of genes associated with mitosis, cell cycle, cell proliferation, cell adhesion, DNA repair, cell survival, ubiquitination, actin remodeling, metabolism and genes. In contrast, PASCs exhibit a very high level of expression of genes related to immunity, inflammation, immune regulation, immune response, immune suppression, lymphocyte activation, T cell marker, T cell proliferation, T cell activation, co-stimulation. PASCs may regulate dendritic cells or T-helper cells at the site of an infection.

DETAILED DESCRIPTION

Figures 1A, 1B, 1C:
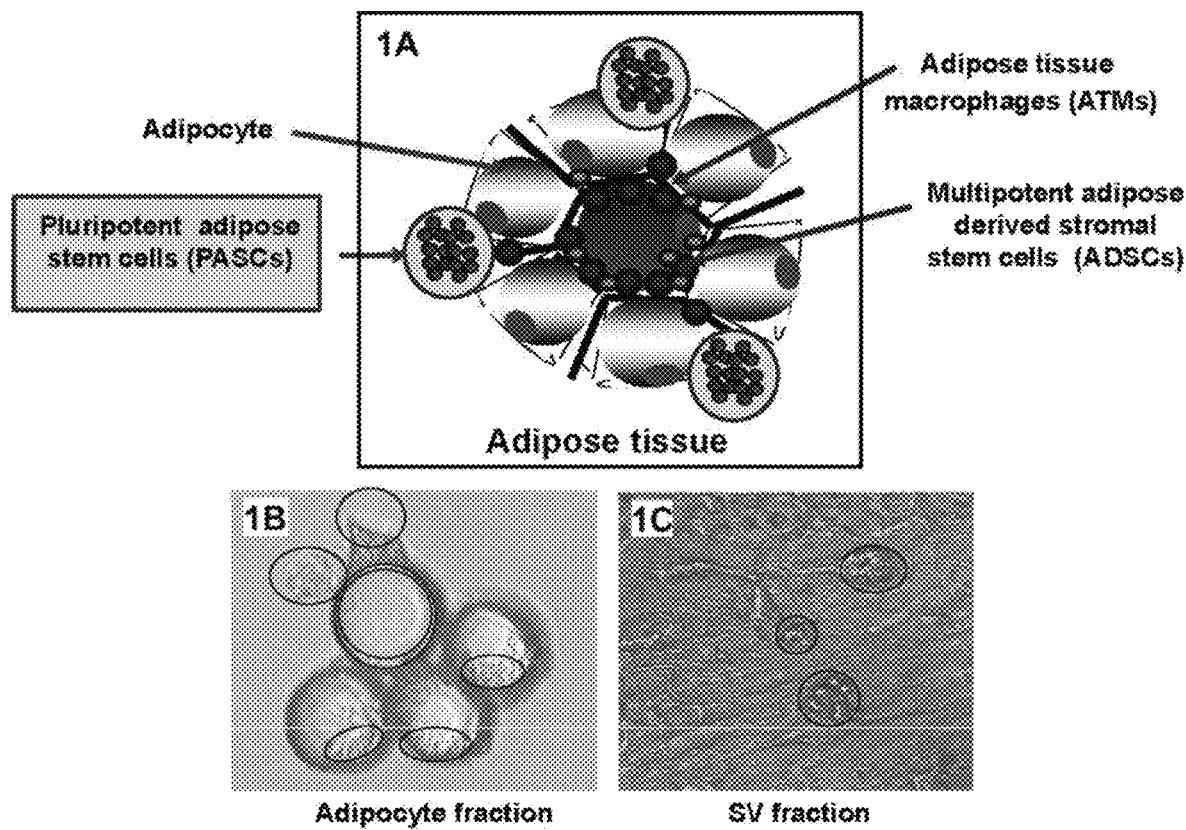
FIGS. 1A-1C illustrates PASCs in (1A) adipose tissue which also contains adipocytes, the stromal vascular fraction including adipose tissue macrophages (ATMs) and multipotent adipose stem cells (ADSCs) among other cell types, (1B) adipocyte fraction (floating cells) (photomicrograph) and in (1C) the stromal vascular fraction (photomicrograph image), PASCs are present in both fractions (marked with circles).

The invention described herein overcomes major clinical limitations, particularly addressing the problems posed by autologous transplantation with pluripotent stem cells that do undergo teratogenesis in vivo, and the need for a high post-transplantation survival rate. Hostile host factors of the engraftment microenvironment such as hypoxia, nutrition deprivation, pro-inflammatory cytokines, and reactive oxygen species can each contribute to unwanted differentiation or apoptosis.

The invention provides the isolation and characterization of a new population of adipose tissue (AT) derived pluripotent stem cells, termed Pluripotent Adipose Stem Cells ("PASCs"). PASCs are isolated using severe cellular stress conditions, including long-term exposure to the proteolytic enzyme collagenase, serum deprivation, low temperatures and hypoxia. Under these conditions, a highly purified population of PASCs is isolated without the utilization of cell sorting methods, magnetic beads or special devices and prolonged cell culture procedures.

The complete process of liposuction, collagen digestion of the aspirated fat, followed by PASCs isolation (100,000,000-200,000,000 PASCs/l of lipoaspirate material), and injection of PASCs (via i.v. or into the damage tissue) takes about 5-7 hours. This procedure is extremely fast and efficient, making it particularly useful in cases of acute injury, stroke, massive heart attack, or burn, in which it is critical to begin the treatment of damaged tissue by enhancing the tissue environment for rapid healing and restoration of function. All procedures can be performed in the same operating room.

Harvesting human adipose tissue by lipoaspiration is a safe and non-invasive procedure (24), and hundreds of millions of adipose cells can be isolated from 1-2 liters of lipoaspirate material (25). Because this procedure takes less than an hour, adipose tissue could prove the ideal source for Muse cell isolation as opposed to bone marrow or dermis.

Using lipoaspirate material, the invention provides a novel methodology for the isolation of a population of human Muse cells under severe cellular stress conditions (e.g., long term incubation with proteolytic enzyme, 4° C., serum deprivation, and/or hypoxia). Purification of human PASCs does not require the use of cell sorting, magnetic beads, special devices, or cell culture procedures.

PASCs can grow either in suspension, forming cell spheres, similar to human ES cell-derived embryoid bodies. However, in adherent culture dishes, PASCs initially form aggregates that start to differentiate into progenitors and mature cells, losing their pluripotency as previously reported (26). Immunocytochemistry studies demonstrate that PASCs express pluripotent stem markers including SSEA3, TR-1-60, Oct3/4, Nanog and Sox2 (26).

PASCs can spontaneously differentiate into mesenchymal, endodermal and ectodermal cell lineages with an efficiency of 23%, 20% and 22%, respectively (26). Interestingly, PASCs preferentially differentiate spontaneously into adipocytes (61%), suggesting that PASCs have an epigenetic memory of their tissue of origin. It may be possible that adipose tissue acts as a natural reservoir for the cells, and without stress PASCs may remain in a dormant state (26-28).

Upon introduction to specific culture conditions, PASCs can differentiate to mesenchymal (adipocytes, skeletal and smooth muscle cells), endodermal (hepatocytes and biliary ducts) and ectodermal (neural cells) cell lineages with an efficiency between 80-90%.

Microarray data confirmed that PASCs over-express the pluripotent stem cell markers SOX2, OCT3/4, (POU5F1) and REX1 3-4 fold in comparison to previously studied multipotent adipose stem cells (ASCs), indicating the intrinsic pluripotent and differential capacity of PASCs. Concordantly, PASCs exhibit up-regulation of genes associated with embryonic development, albeit at a much lower level than is observed for hESCs or iPSCs.

Microarray analysis reveals that PASCs highly express genes involved in cellular protection against oxidative stress. For example, PASCs over-express ALDH1A2 (47-fold change versus ASCs) and SOD2 (41-fold change versus ASCs) which have anti-oxidative stress and anti-apoptotic functions (27, 28). Additionally, these cells also exhibit up regulation of CXCL2 gene expression, a critical chemokine involved in stem cell homing (29-30).

PASCs have a relatively low expression of many genes involved in tissue development, cellular assembly and organization, cellular function and maintenance, DNA replication, repair, and cell cycling in comparison with ADSCs. These results suggest an intrinsic non-tumorigenic capacity of PASCs, similar to previously published data of the regenerative properties of Muse cells in the absence of the production of teratomas upon transplantation in vivo (22-23). However, under abnormal stress conditions (e.g. programming Muse cells with the Yamanaka's factors), it may be possible to activate endogenous Muse cells, which could account for the small population of cells that are converted into iPS cells (23). Such a theory is supported by previous studies regarding the possible role of adult organ-specific positive Oct4 (+) stem cells during asymmetric division in the generation of cancer cells (31).

Many genes related to DNA repair are up-regulated in PASCs, indicating a potentially high capacity to resist DNA damage as a result of severe cellular stress. Furthermore, several ABC-cassette genes were differentially expressed in PASCs, indicating that active expression of drug transporter genes may play a role in observed stress resistance.

Many of the differentially expressed genes in PASCs are highly conserved, with homologues present in numerous small organisms (yeast, *S. Cerevisiae, C. elegans, chlamydomonas, T. californica, drosophila*, etc.). This indicates the possibility that PASCs play a role in a highly conserved cellular mechanism related to cell survival in response to severe cellular stress (32-33).

In various embodiments, new methods are provided for the isolation and proliferation of a population of pluripotent stem cells. These cells can be isolated with a high degree of purity (>90%) by using a simple yet highly efficient purification technique involving severe cellular stress conditions. The methods described herein provide a significant number of cells without the need of cell sorting, nanobeads techniques and long-time cell expansion. Moreover, lipoaspiration is a safe and non-invasive procedure that allows for rapid procurement of suitable source material for therapeutic applications.

Without being bound by a particular theory, it is believed that the cells that give rise to pluripotent adipose stem cells (PASCs) isolated according to the methods described herein, are small cells that are present in adipose tissue in both adipocyte fraction (top layer, PASCs are surrounding adipocytes) as well as in the stromal vascular fraction (SVF). The adipose SVF contains different cell types including adipose tissue macrophages (ATMs), multipotent adipose stem cells (ADSCs), endothelial cells, pericytes among others.

PASCs, prior to cellular stress disruption, are present in a quiescent state under normal physiological circumstances within the cellular niche (34-35). Multiple adult stem cell lineages have been shown to exist in a quiescent state at various time points throughout their lifespan, including hematopoietic stem cells and epithelial stem cells, which allegedly plays a role in the preservation of their self-renewal (36-37).

Paracrine/autocrine interactions between the adipocyte fraction and the cellular components present in the SVF could be critical contributors to disruption of the quiescent stage (normal physiological circumstances), and inducing the release and activation of PASCs from both fractions. This paracrine interaction involves cell-cell contact as well as secretion of soluble factors (cytokines, growth factors, etc), which could play a significant role in such an activation process.

Definitions

The term stem cells (stammzellen), established over a century ago by German scientist Ernst Haeckel (38-40), refers to cells with the capacity of self-renewal and the ability to differentiate into various cell types. Based on their ability to give rise to adult tissues of the three embryonic germ cell lineages, there are different types of stem cells.

The term 'unipotent' stem cells" refers to cells having the ability to differentiate into one cell type, for example, a muscle stem cell differentiating into a mature muscle cell.

The term "oligopotent stem cells" refers to the capacity of such cells to differentiate into few, but not all, cell types within a specific tissue (e.g. lymphoid or myeloid stem cells) (41).

The term "multipotent stem cells" refers to the ability of such cells to differentiate into all cell types from a specific germ layer, which includes mesenchymal stem cell (MSC) (42-43). For example, adipose derived stem cells (ADSCs) are multipotent stem cells that have the potential to differentiate only into mesenchymal cell lineages, including adipocytes, chondrocytes, osteoblasts, and myoblasts in vitro and to undergo differentiation in vivo, in a manner similar to that of multipotent stromal cells derived from bone marrow (24, 44).

The 'totipotent' stem cell is the most primitive stem cell, most commonly known as the zygote, capable of differentiation into embryonic and extraembryonic cell types (placenta) and even create an entire organism (45-46).

By "pluripotency" and "pluripotent stem cells" or "PSCs", it is meant that such cells have the ability to differentiate into all types of cells in an organism. Pluripotent cells are characterized by the expression of several pluripotency markers known by one of ordinary skill in the art. Such markers include, but are not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In certain embodiments pluripotent cells are capable of forming or contributing to ectoderm, mesoderm, or endoderm tissues in a living organism.

Because embryonic stem cells ("ESCs") and induced pluripotent stem cells ("iPSCs") exhibit self-renewal that is frequently uncontrolled and often materializes in teratoma formation, cell pluripotency is often erroneously defined as the inherent capacity of cells to differentiate into all types of cell and to produce teratomas.

As used herein, "PASCs (pluripotent adipose stem cells) are positive for SSEA-3, SSEA-4, Oct 3/4, SOX-2, TRA1-60, and NANOG. PASCs are isolated from adipose tissue under severe stress conditions, and are distinguished from iPSCs and ESCs in that the PASCs described herein exhibit both low proliferative and telomerase activities, a normal karyotype, as well as asymmetric growth, and do not undergo tumorigenesis or teratoma formation when transplanted into a host organism (e.g. immunodeficient mice). In addition, hES and iPS cells express the above-listed markers at a level that is many thousand-fold higher than the low level of expression observed in PASCs. PASCs differ from Muse (multilineage differentiating stress-enduring) cells in their expression of cell markers. PASCS have the capability to differentiate to any type of cell of mesodermal, endodermal or ectodermal origin.

The term "multipotent stem cells" refers to the ability of such cells to differentiate into all cell types from a specific germ layer, which includes the increasingly popular mesenchymal stem cell (MSC) (42-43). For example, adipose-derived stem cells (ADSCs) are multipotent stem cells that have the potential to differentiate only into mesenchymal cell lineages including adipocytes, chondrocytes, osteoblasts, and myoblasts in vitro and to undergo differentiation in vivo, in a manner similar to that of multipotent stromal cells derived from bone marrow (24, 44).

Muse (Multi-lineage differentiating stress enduring) cells are pluripotent stem cells present in mesenchymal tissue of the body. These cells are highly resistant to cellular stress. Muse cells are SSEA3(+)/CD105(+) cells isolated by cell sorting and without use of stress conditions. Muse cells are able to generate cells representative of all three germ layers and do not undergo teratoma formation when transplanted into a host environment in vivo. (22-23).

The terms "primary cells", "primary cell lines", and "primary cultures" are used interchangeably herein to refer to cells and cell cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary adipose cells of the present invention are maintained for fewer than 10 passages in vitro prior to use.

As used herein, "co-culturing" of cells refers to maintaining two or more populations of cells in contact with each other such that the conditions permit autocrine and/or paracrine interactions between the cell populations. The co-culturing environment can be a conventional cell culture environment, or it can be incubation or storage of the cell populations in a common vessel, such as a centrifuge tube or culture flask.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human or veterinary subject, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans. Also contemplated are veterinary subjects, including, but not limited to, horses, cattle, dogs, cats, sheep, pigs, goats, rabbits, and rodents.

By "adipose" is meant any fat tissue. The adipose tissue may be brown or white adipose tissue, derived from, omental/visceral, mammary, gonadal, or other adipose tissue site. In certain embodiments the adipose is subcutaneous white adipose tissue or visceral adipose tissue or any other tissue containing adipose cells. The adipose tissue may be from any organism having fat tissue. Preferably, the adipose tissue is mammalian, most preferably the adipose tissue is human. A convenient source of adipose tissue is from liposuction surgery, however, the source of adipose tissue need not be so limited.

For isolation of primary cells from tissue, an appropriate solution containing collagenase (0.1%) may be used for dispersion or suspension. Such solution will generally be a balanced salt solution, e.g. Iscove's modified DMEM, normal saline, PBS, Hank's balanced salt solution, etc., in conjunction with an acceptable buffer at low concentration, generally from 5-25 mM. Convenient buffers include HEPES, phosphate buffers, lactate buffers, etc. Collagenase digestion releases all cells present in adipose tissue, including (i) the adipocyte fraction (floating cells in the top layer) and (ii) the stromal vascular fraction (cells able to precipitate after centrifugation, e.g. adipose tissue macrophages, adipose derived stem cells, endothelial cells, fibroblasts). PASCs are present in both the adipocyte and stromal vascular fractions. This digestion is typically performed by incubation of the lipoaspirate material with an equal volume of DMEM containing 0.1% collagenase for 30-45 min at 37° C. in a shaking incubator at 110 rpm.

"Severe cellular stress" includes, but it is not limited to, exposing cells to collagenase, a proteolytic enzyme that breaks the peptide bonds in collagen. Collagen is a vital part of the extracellular matrix in flesh and connective tissue in the animal body. In contrast to serine proteases (trypsin, chymotrypsin, and elastase), collagenase does not undergo self-degradation, making a very effective protease. Severe cellular stress also includes exposing cells to starvation conditions (no nutrients, no glucose), hypoxic conditions (lack of oxygen), low temperatures, heat shock, and lysis by mechanical procedures such as sonication.

Methods of Isolation of PASCs

Figure 4:
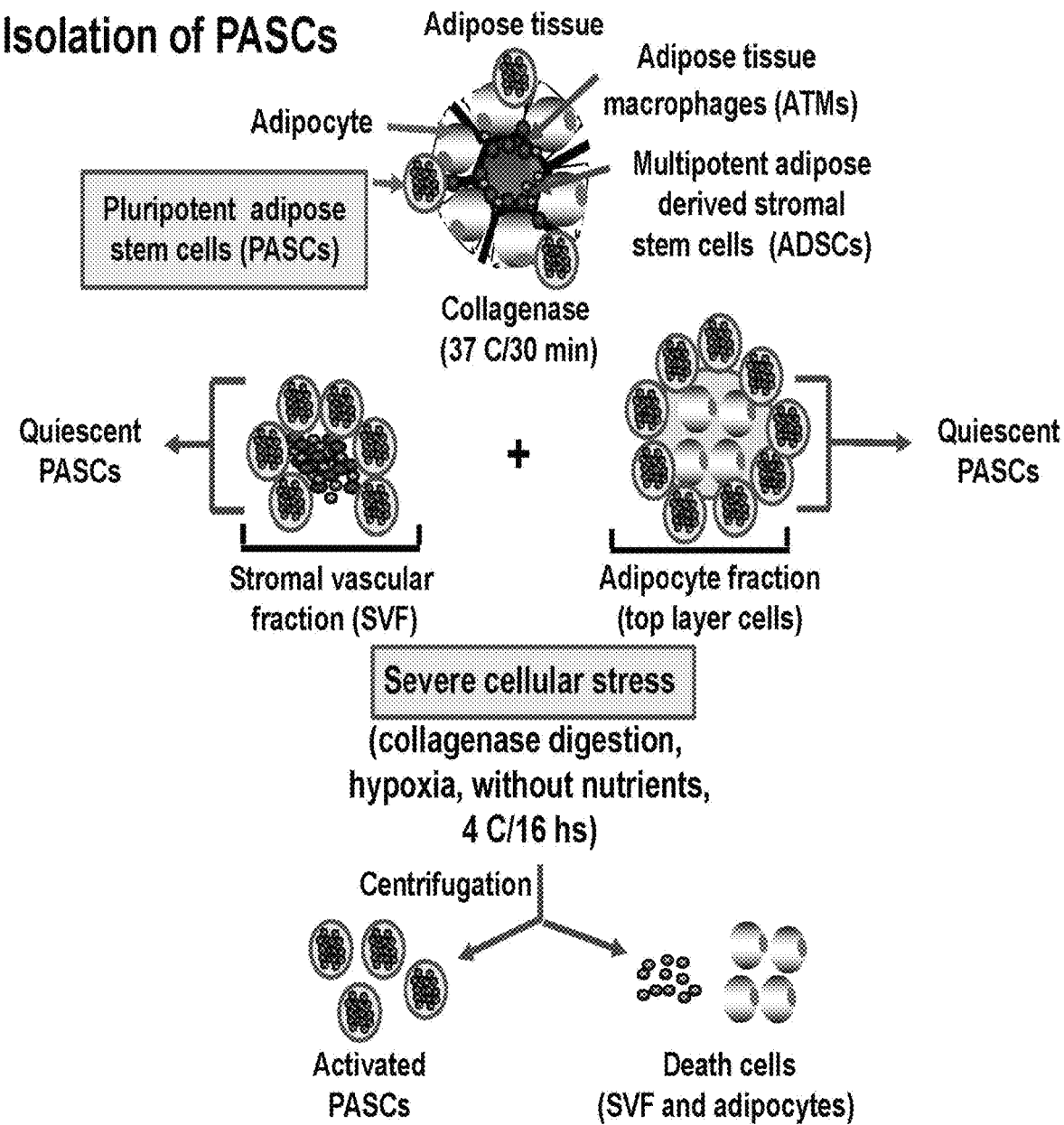
FIG. 4 illustrates the presence of pluripotent adipose stem cells (PASCs) in adipose tissue. After collagenase treatment and centrifugation, the adipocyte fraction (floating cells) and the stromal vascular fraction (SVF) (cell pellet) are released from adipose tissue. The digested material is then subjected to severe cellular stress which includes long incubation with collagenase (6-8 hrs), lack of nutrients, low temperature, high hypoxia and also the paracrine/autocrine interaction between the adipocyte fraction and the stromal vascular fraction, which lead to the release of cytokines/chemokines from adipocytes and cells present in the SVF. PASCs are the only cell type that can survive such external stress conditions. PASCs are present in both the adipocyte and stromal vascular fractions.
Figure 5:
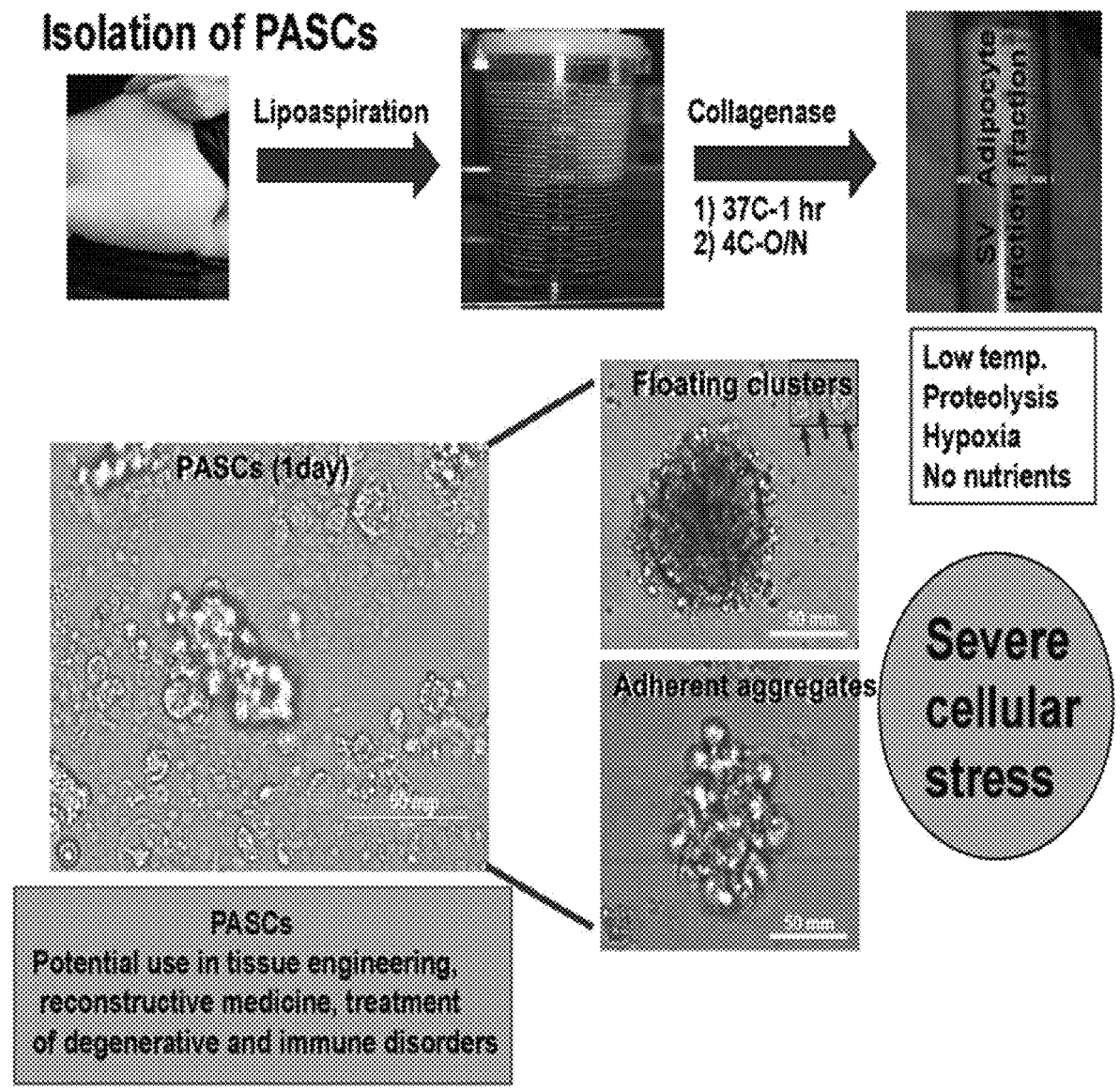
FIG. 5 illustrates a simple scheme of PASCs isolation from lipoaspirate material. After 30 min/37° C. digestion of adipose tissue, all cells released from adipose tissue were exposed to severe cellular stress (extended incubation with collagenase, lack of nutrients, low temperature, high hypoxia, release of cytokines/chemokines from adipocytes and other cell components). PASCs are the only cell type that can survive such external stress. PASCs are present in both adipocyte and stromal vascular fractions. PASCs can grow as individual cells and also by forming clusters of cells in suspension, as well as growing as adherent cells. Based on their pluripotent characteristics, non-teratoma formation and high percentage of grafting, PASCs have the potential to be used use in tissue engineering, reconstructive medicine, and treatment of degenerative and immune disorders

One non-limiting approach to the differentiation and proliferation of PASCs can be performed as described below and schematically illustrated in FIGS. 4-5. Briefly, adipose tissue can be collected by lipoaspiration from a subject (e.g., a human, a non-human mammal) of any sex, age and race under local anesthesia. The tissue is harvested from subcutaneous abdominal tissues or/and other part of the body containing fat (e.g. tights) by simple procedures, e.g., manually by using specific syringes, or using an automatic lipoaspirator following standard protocols. Blood that normally is presented in the lipoaspirate material is removed by several washes with PBS (or other buffer). The lipoaspirate material is then subjected to centrifugation to remove oil (top lawyer) and tumenescent solution (low lawyer) from the adipose tissue (middle lawyer). The concentrated adipose tissue is then digested with a proteolytic enzyme, such as 0.02-1% collagenase, typically 0.1% collagenase, and incubated at 37° C. for 30 minutes using a shaker incubator at 100 rpm. Digested material is then kept at 2-12° C., typically at 4° C., for about 4, 6, 8, 10, 12, 16, 18, 20, 22, 24, 26, 28, or 30 hours, preferably for about 6-8 hours (FIG. 5). During that process, samples can be slightly shaken (20-30 rpm) or rotated in angle (90°-180°, to maximize cell-cell contact between adipocyte fraction and SVF fraction). Hypoxic conditions typically means an environment of 0.01% to 10% oxygen. In one embodiment, the hypoxic condition is an environment of 0.01% to 5% oxygen, such as, for example, about 1% oxygen.

In some embodiments, the proteolytic enzyme is a serine protease enzymes (e.g., trypsin, chymotrypsin); aspartate protease (e.g. pepsin); cystein protease (e.g. papain, chymopapain); metalloproteinases (e.g. thermolysin, glutamate protease). Concentrations of these proteolytic enzymes vary according to their efficiency to activate and release PASCs. Severe cellular stress conditions could also include vortexing the cells for short (30 seconds) to long periods of time (10 min), optionally including additional proteolysis. Other alternative methods for severe cellular stress conditions include sonication of the cells (externally) at different power potential (1-50 kHz) at different times (1 min to 1 hour) and/or different temperatures (4-37° C.), optionally including additional proteolysis.

The resuspended material is then centrifuged at 1,000 rpm/4° C./10 min. The adipocyte fraction (floating cells) is removed by aspiration from the stromal vascular fraction (cell pellet). This stromal vascular fraction contains living PASCs that are resistant to the long collagenase/lack of nutrients/4° C./hypoxia treatment (FIG. 5) and other death cell components, non-resistant to such environment including ADSCs, adipose tissue macrophages, endothelial cells (FIG. 5). These dead cells are removed from the PASCs by successive washes, e.g., in DMEM/5% FCS/antibiotics. Highly purified PASCs can grow as individual cells or by forming cell clusters in suspension, or attached to a cell culture dish (FIG. 5). PASCs maintain their pluripotent characteristics indefinitely. Isolation, differentiation and proliferation of PASCs can be easily performed by any cell biologist (Ph.D., Master in Science, technician) after receiving the appropriate training.

In various embodiments, methods are provided for the isolation and proliferation of a population of pluripotent adipose stem cells (PASCs). In contrast to induced pluripotent stem cells, the pluripotent adipose stem cells of the invention can be isolated without the use of genetic manipulation. Moreover, the methods described herein provide a significant number of cells without the need for long time cell expansion.

In certain embodiments, human adipose tissue is used as a source of pluripotent adipose stem cells because cell isolation from this tissue requires a minimally-invasive technique. In adipose tissue, different cell types (adipose derived stem cells, progenitors, and mature cells) are highly abundant. However, the methods described herein need not be limited to the use of adipose tissue and other tissues (e.g., bone marrow, skin, blood, etc.) can similarly be used. Harvesting cells from adipose tissue offers significant advantages over cell isolation from bone marrow. The harvesting procedure of cells from adipose tissue is less painful and many more cells may be harvested. For example, the number of ADSCs (mesenchymal origin) present in adipose tissue is 100 to 1000 times higher per milliliter than that of mesenchymal stem cells in bone marrow (26).

In one embodiment, the invention provides a method of isolating pluripotent adipose stem cells (PASCs) from adipose tissue. The method typically comprises the steps of: (a) providing an adipocyte tissue sample; (b) subjecting cells in said sample to initial stress conditions; (c) co-culturing adipocytes and a stromal vascular fraction for 2-36 hours; (d) recovering the viable cells; and (e) optionally culturing the recovered cells. In one embodiment, the stress conditions of step (b) comprise incubating the cells in a medium containing a proteolytic enzyme. The co-culturing of step (c) can be performed in the presence of a proteolytic enzyme as well. In a more specific embodiment, the enzyme is collagenase.

The adipose tissue sample may be obtained via means known to those skilled in the art, including lipoaspiration. In one embodiment, the lipoaspiration is performed on a subject to whom the isolated PASCs will be administered. Alternatively, the lipoaspirate may be obtained from a suitable donor, preferably one allogeneic with the recipient. Typically, the sample is used immediately upon collection from the donor, usually within about 1-2 hours of collection. Optionally, the lipoaspirate material can be kept at 4° C. up to 48 hours after the lipoaspiration procedure. Considerations of histocompatibility are of greatest concern when the PASCs are to be administered to a host for therapeutic purposes. Such considerations are of lesser or no importance to other applications, such as some cases of experimental use, screening or testing, and where conditioned medium (and not cells) will be administered to the recipient. Preliminary data, however, show that allotransplantation (transplant of PASCs from one individual to another) can be performed without immunorejection by the host individual.

PASCs isolated from adipose tissue may be cultured in vitro under various culture conditions. PASCs are typically grown as undifferentiated pluripotent stem cells in non-adherent culture dishes/flasks. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin. Because PASCs have a mesenchymal origin, various custom cell culture media designed to grow mesenchymal stem cells under optimal conditions can be utilized. These special culture media are commercially available from companies such as BD, Stem Cell Technology, and the like.

In one embodiment, the adipose cells are maintained in culture in the absence of feeder layer cells. In certain embodiments the culture may contain growth factors to which the cells are responsive. Growth factors, as defined herein, are molecules capable of promoting survival, growth and/or differentiation of cells, either in culture or in the intact tissue. Growth factors include polypeptides and non-polypeptide factors.

PASCs can be more easily isolated than Muse cells (another pluripotent stem cell isolated under stress conditions) because isolation of PASCs does not require cell sorting, culture procedures.

The stress conditions of step (b) include, but are not limited to, protease treatment, exposing cells to starvation conditions (no nutrients, no glucose), hypoxic conditions (lack of oxygen), low temperatures, heat shock, and lysis by mechanical procedures such as sonication. Two or more such stressors may be used together. The stress conditions are typically applied for 20-60 minutes, and may continue through the co-culturing step. For example, the cells obtained from adipose tissue can be treated initially with protease (e.g., collagenase) for about 45 minutes at 37° C. (step (b)), followed by storage in hypoxic conditions at 4° C. for 2-8 hours (or overnight; step (c)), during which time the proteolytic activity is permitted to continue. In another embodiment, the stress conditions comprise incubating the adipose tissue in collagenase for 30-45 minutes at 37° C., followed by 6-8 hours co-culturing of the cells at 4° C. (refrigerator). The decrease of temperature of the cells from 37° C. to 4° C. is, in one embodiment, gradual (around 1° C. every 7-8 min).

In a typical embodiment, the co-culturing is performed in the absence of serum. For example, the co-culturing can be performed in Dulbecco's Minimum Essential Medium (DMEM), or a similar basic medium known in the art. The co-culturing can be as simple as storing the cells in a centrifuge tube without or with slight shaking or angle rotation. Stressors can be applied, for example, by closing the cap of the tube to create hypoxic conditions, placing the tube or other container into a refrigerator (cooling), as well as using a nutrient-free medium (starvation).

In one embodiment, the co-culturing is performed for 4-24 hours. The length of the co-culturing can be modified to accommodate timing considerations. For example, if isolated PASCs are required on an urgent basis, such as for treatment of traumatic injury, steps (b) and (c) can be shortened, and multiple stressors applied, to accelerate the process of selecting for stress-resistant cells.

In one embodiment, the recovering of step (d) comprises recovering at least 200,000 PASCs. In other embodiments, the recovering comprises recovering at least 50,000, 100,000, 500,000 PASCs, or at least 1,000,000 PASCs. These quantities of PASCs are typically recoverable within 24 hours of initiating the stress conditions of step (b). In some embodiments, at least 500,000 PASCs are recovered within 8 hours of initiating the stress conditions of step (b). In other embodiments, the PASCs are recovered within one week. In one embodiment, the method is performed without cell-sorting. Typically, 100,000,000 PASCs can be obtained from 1 liter of lipoaspirate material 6 hours after lipoaspiration. PASCs are normally present as individual cells or form clusters, and can grow in suspension as well as form adherent cells (FIG. 5).

Cells, Compositions & Conditioned Media

PASCs are highly abundant in the adipocyte and stromal vascular fraction obtained from adipose tissue (FIG. 1). PASCs have the potential to be used for autologous tissue engineering and regenerative medicine in humans. Furthermore, PASCs have the potential to not only differentiate to progenitors, but also to mature cells from the three germ line cells (any kind of cell present in the body). PASCs can be used for the treatment of many disorders as well as for the testing of new drugs.

In one embodiment, the PASCs, such as those recovered using the isolation method described here, are SSEA-3 and/or CD105 positive. In some embodiments, the cells express one or more markers of pluripotency selected from the group consisting of SSEA3, Nanog, Oct3/4, Sox2, Klf4, and TR1-60. In some embodiments, the cells express one or more markers of endodermal progenitor cells, such as Cytokeratin 19, HNF-3 alpha/FoxA1, EOMES, HNF-3 beta/ FoxA2, FABP1/L-FABP, SOX7, FABP2/I-FABP, SOX17, GATA-4, TCF-2/HNF-1 beta, and Goosecoid. In some embodiments, the cells express one or more markers selected from the group consisting of alpha-Fetoprotein/ AFP, HNF-4 alpha/NR2A1, beta-Catenin, MIXL1, GATA-4, SALL4, GATA-6, SOX7, GDF-1, SOX17, and GDF-3. In other embodiments, the cells express one or more markers of mesodermal progenitor cells, such as EpCAM/CD326, NCAM/CD56, cardiac sarcomic actin, and BODIPY C-16. In yet other embodiments, the cells express one or more markers of ectodermal progenitor cells, such as BMP-4, Noggin, Chordin, Otx2, FGF-8, p63/TP73L, FoxJ3, Pax2, GBX2, Pax6, Nestin, and beta-III Tubulin.

Adipose tissue is important in metabolic homeostasis through its role as an energy depot and endocrine organ (47-48). Adipose tissue is composed of adipocytes (mature cells), the stromal vascular fraction containing adipose tissue macrophages (ATMs), mesenchymal stem cells named adipose stem cells (ADSCs) and the population disclosed herein, named pluripotent adipose stem cells (PASCs), which are highly abundant in both the adipocyte and stromal vascular fractions, among other components (FIG. 1).

Adipogenesis, the process by which ADSCs are converted to adipocytes involves three major stages: (i) hASC commitment to the preadipocyte phenotype, characterized by the formation of conversion of typical spindle-shape cells to more rounded cells containing cytoplasmic lipid inclusions (pre-adipocytes); (ii) early-stage preadipocyte differentiation to adipocytes (immature adipocytes), and (iii) late-stage preadipocyte differentiation into adipocytes, characterized by cell-cycle arrest with further activation of PPARγ and C/EBPα. These pro-adipogenic events are further modulated by other transcriptional factors to promote gradual intracellular lipid accumulation and maturation into adipocytes (FIG. 2) (49-52).

Figure 2:
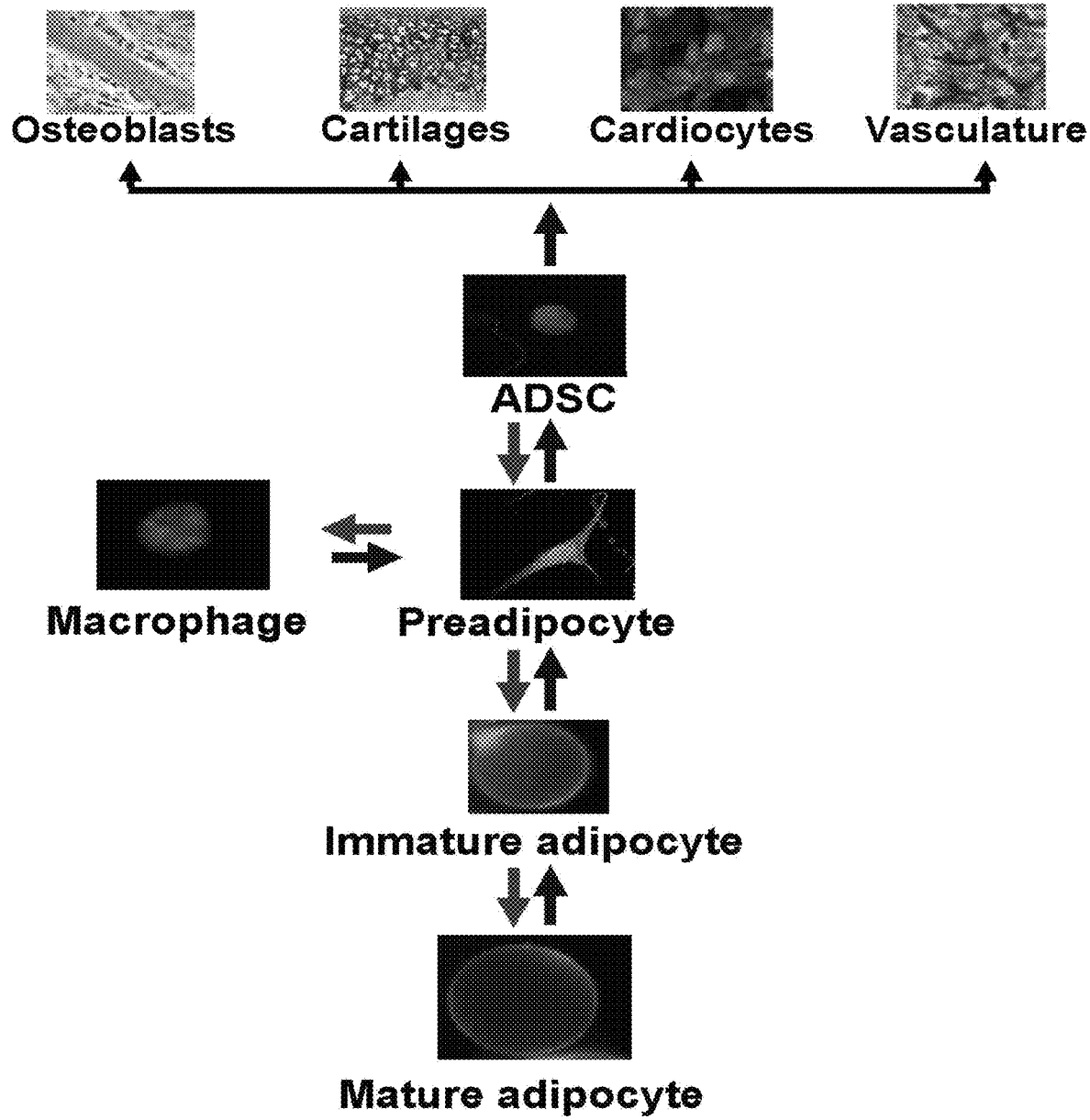
FIG. 2 illustrates the high degree of cell plasticity in the different cell components of adipose tissue. ADSCs can differentiate along adipocyte, osteoblast, chondrocyte, and other mesenchymal cell lineages in a manner similar to that of multipotent stromal cells derived from bone marrow. It is generally accepted that mature adipocytes do not regularly undergo mitosis, and thus, an increase in adipocytes usually reflects a differentiation of preadipocytes. However, several studies indicate that mature adipocytes could also have proliferative activity. Recent studies suggest adipocytes can dedifferentiate to preadipocytes and can even differentiate to a multipotent cell population. Of note, preadipocytes have also been observed to rapidly and efficiently differentiate into typical macrophages and vice-versa demonstrating significant plasticity of these cells.

ADSCs are multipotent stem cells that have the potential to differentiate only into mesenchymal cell lineages including adipocytes, chondrocytes, osteoblasts, and myoblasts in vitro and to undergo differentiation in vivo, in a manner similar to that of multipotent stromal cells derived from bone marrow (24-25, 44) (FIG. 2).

Figure 3:
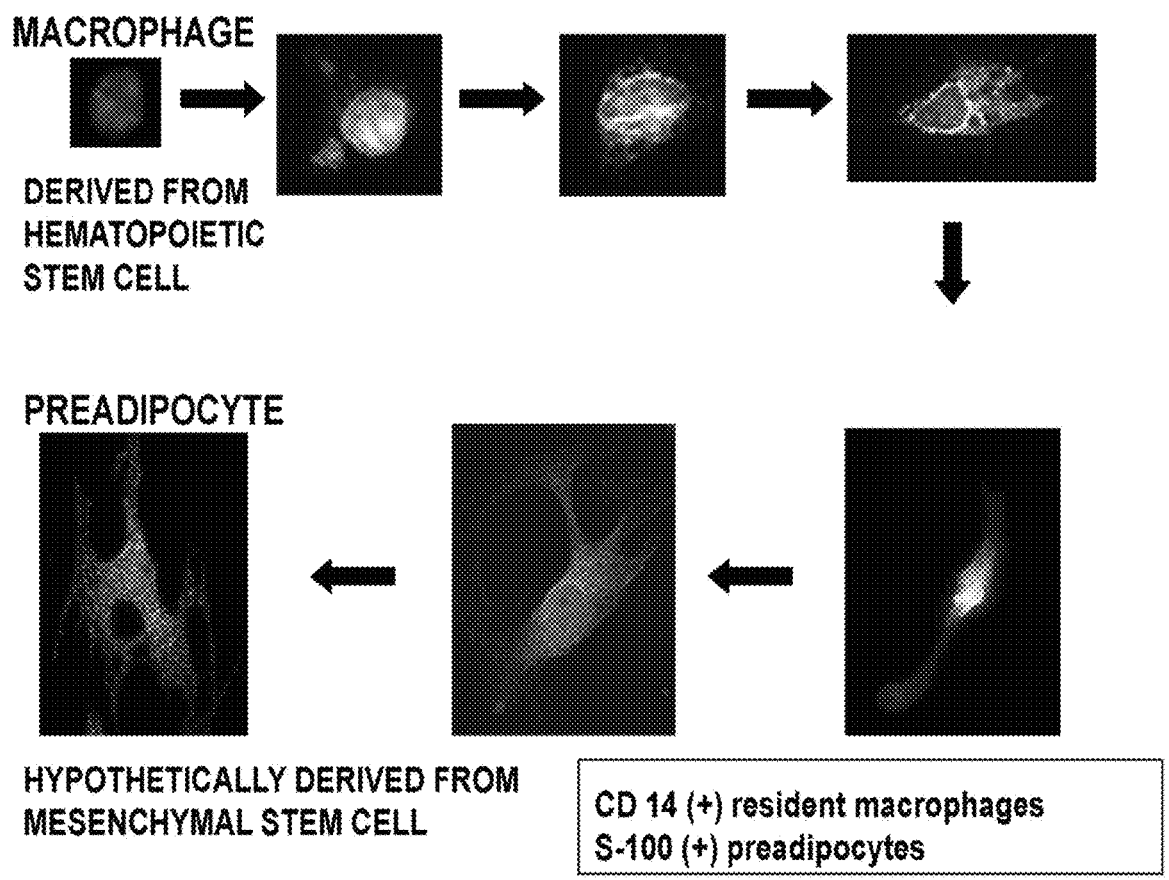
FIG. 3 illustrates another example of cell plasticity present in adipose tissue indicated by the capacity of adipose tissue macrophages (hematopoietic stem cell origin, CD14 (+) cells) to be differentiated to preadipocytes (mesenchymal stem cell origin, S-100 (+) cells). During ATMs differentiation to preadipocytes, cells express both CD14 (+) and S-100 (+) markers. Most preadipocytes observed were CD14 (+) to varying degrees. As macrophages differentiated towards a preadipocyte morphology, the cells expressed less CD14 and more DLK/S-100.

It is generally accepted that mature adipocytes do not regularly undergo mitosis, and thus, an increase in adipocytes usually reflects a differentiation of preadipocytes (24-25). However, several studies indicate that mature adipocytes could also have proliferative activity (53-54). Recent studies suggest adipocytes can dedifferentiate to preadipocytes [21] and can even differentiate to a multipotent cell population (FIG. 2) (55-56). Of note, adipocyte precursors and preadipocytes have also been recently observed to rapidly and efficiently differentiate into typical macrophages (57-58). (FIG. 2). Some reports indicate, although with very low efficiency. Adipose tissue macrophages (hematopoietic stem cell origin) can differentiate to preadipocytes (mesenchymal stem cell origin) (59). (FIG. 3). These results indicate the high degree of cell plasticity in the different cell components of adipose tissue.

The invention further provides PASCs as described herein. The PASCs are typically present in a composition that is essentially free of other cell types (e.g., at least 90% pure, typically 95% pure, and in some embodiments, at least 99% pure). In an alternative embodiment, the PASCs are present in combination with ADSCs, such as at a ratio of 50:50, 75:25, 25:75, or other ratio, as desired. ADSCs are currently used for soft tissue regeneration (face, breast, etc). Because PASCs differentiate much faster into fat and muscle cells than ADSCs (at least 3-fold faster), they would be more efficient than ADSCs. for such treatments. Combination between PASCs and ADSCs would be one option for combining the features of both cell types. Because PASCs cells are already adapted to severe cellular stress, similar to the environment of damaged tissue, they have a high rate of survival after transplantation and high grafting efficiency, which is critical for tissue regeneration.

Also provided is a composition comprising PASCs isolated according to the method described herein, or progeny thereof (including a cell line derived therefrom), and a therapeutically acceptable buffer solution, wherein the PASCs are suspended in a physiologically compatible buffer solution (e.g. PBS). Also provided is a composition comprising conditioned medium that has been recovered from a culture of PASCs isolated in accordance with the methods described herein. Strategies for preparing therapeutic conditioned media are described, for example, in Bhang et al. (60). Culture conditioned media contains various factors (cytokines, chemokines, growth factors, peptides, proteins) secreted by PASCs that have been maintained in culture for a period of about 24-72 hours. These factors have anti-inflammatory and/or immunomodulation properties that could be used for treatment of many diseases, especially those related to immunological or autoimmune diseases.

In one embodiment, the composition comprises PASCs isolated from lipoaspiration. In one embodiment, the lipoaspiration is performed on the subject to whom the composition is administered. In a typical embodiment, the composition is administered to the subject within 6 hours of the lipoaspiration. In other embodiments, the composition is administered within 12, 24, or 36 hours of the lipoaspiration.

Methods of Using PASCs

The invention provides a method of ameliorating tissue damage in a subject. The invention additionally provides a method of repairing or regenerating diseased or damaged tissue in a subject. In another embodiment, the invention provides a method of enhancing tissue function and/or a method of delivering cytokines to tissue of a subject. Typically, the method comprises administering a composition of the invention to the subject. Where the composition comprises PASCs, optionally, it is administered under conditions permitting the PASCs of the composition to divide and to populate a site of tissue damage. Migration of PASCs to the site of damage is not required in all embodiments, as factors released by the PASCs provide therapeutic benefits.

In some embodiments, the tissue damage comprises traumatic injury or disease-associated damage. Representative examples of traumatic injury comprise hypoxia, bone injury, laceration, gunshot wound, and spinal cord injury. In another embodiment, the disease-associated damage comprises damage associated with diabetes, vascular disease, infection, degenerative neurological disease, cancer. In one embodiment, the composition is used to regenerate soft tissue, such as for breast and face reconstruction, and other forms of plastic surgery and aesthetic medicine. In another embodiment, the composition is used to regenerate muscle tissue, such as for treatment of acute injuries and sports medicine. In yet a further embodiment, the composition is used to treat immune and autoimmune diseases, including, for example, Huntington's Disease, Multiple Sclerosis, Rheumatoid Arthritis, Lupus, Diabetes type I, Crohn's disease. In another embodiment, the composition is used as an anti-aging reagent, such as by injection in facial and other tissues for rejuvenation. The composition can comprise an extract of proteins, lipids and/or other substances from PASCs for use in cell rejuvenation, prepared as a cream, oil, or other topical application. The composition can be a personalized rejuvenation product, prepared from material isolated from the subject's own body. Based on these potential applications of PASCs, the creation of a "Bank of PASCs" could be ideal for use in preventive medicine.

Compositions of the invention can be used to treat injured soldiers. Limb vascular injuries represent 50-70% of all war injuries. Management of these injuries on the modern battlefield presents many unique and demanding challenges. Limb vascular injuries are produced by high explosives, munitions, and high-velocity missiles, often causing soft-tissue destruction. In these types of surgical interventions, many service members experience multiple revision surgeries and are faced with at least some scarring. Moreover, this type of wounding frequently leads to chronic pain and limited motion. Insufficient soft tissue coverage of bone and other vital structures is a frequent factor contributing to pain, limited motion and even amputation. Severe ischemia produces total necrosis of tissue, but in moderate ischemia, progenitor cells can survive and initiate tissue regeneration. Providing treatment as soon as possible after injury has not only saved lives, but has also greatly increased the degree to which limb function can be preserved for service members wounded in the battlefield. Time to regenerate new tissue and promote neovascularization is critical to avoid cell death and tissue necrosis in the injured area. Providing treatment as soon as possible after injury has saved lives and preserved optimal function for most of the personnel wounded in the battlefield. Because of their pluripotency, non-teratogenesis, fast cell differentiation process, high grafting efficiency, PASCs are ideal cells to provide injured military personnel with alternatives to prosthetics and to mitigate scarred, nonfunctional healing using patient's own pluripotent stem cells. PASCs could not only regenerate new tissue, but also improve the survival of cells within the zone of injury and actively enhance and direct the regenerative capacity of the local tissues to preserve and restore vital body components such as nerve, vasculature and bone, and the fragile soft tissue envelope surrounding them. The use of PASCs offers the potential to return functional soft tissue mass to the craniofacial region and to extremities of injured soldiers, and can facilitate their rehabilitation. Furthermore, PASC isolation and transplantation could be readily performed in the same operating room located in the battlefield or Level II-treatment facility, instead of transporting the injured soldier to a Level III-treatment facility.

PASCs have the potential to elucidate new avenues of cancer research, for example, with regards to cancer stem cells, quiescence, malignancy and post-treatment relapse. In some embodiments, the PASCs of the invention are used in screening for new therapeutic agents, such as for anti-cancer drug screening.

The primary cell population may be used immediately. Alternatively, in certain embodiments, the cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

Figure 6:
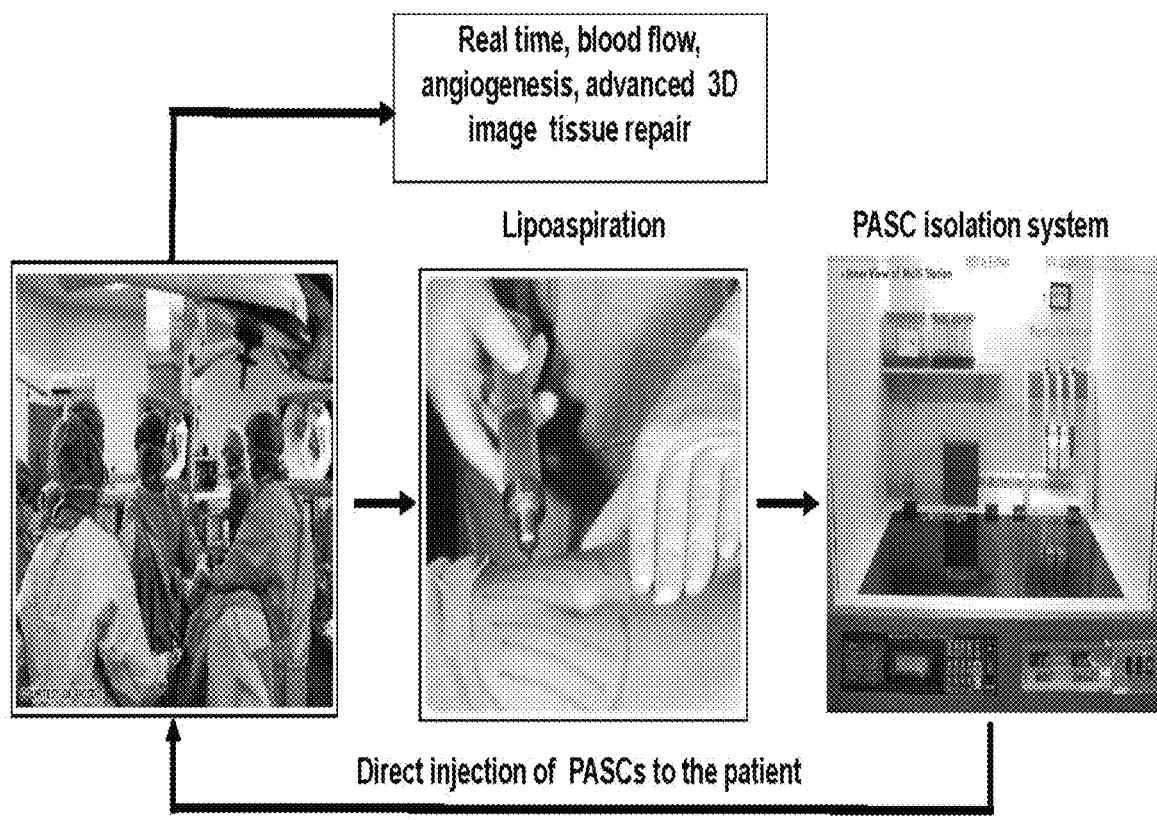
FIG. 6 is a schematic representation of the different procedures including liposuction, collagen digestion of the aspirated fat, PASCs isolation and injection of PASCs (via i.v. or into the damage tissue). This procedure is extremely fast between (5-7 hours) and efficient (1,000,000 PASCs/1 of lipoaspirate material). It is possible to measure in real time the number of PASCs injected into the patient, the flow of the injected cells, oxygen pressure, angiogenesis levels and other parameters according to the treatment. One of the advantages of this technology is the ability to treat patients suffering acute injury, stroke, massive heart attack, or burn immediately after the injury has occurred. There is a critical time frame for tissue repair of these types of injuries. PASCs are therefore ideal cells to treat such acute disorders. Furthermore, all procedures can be performed in the same operating room.

The isolation of human pluripotent stem cells from adipose tissue opens new avenues for autologous cell-based therapy that includes tissue engineering, reconstructive medicine and the treatment of degenerative and immune disorders (e.g. Parkinson's Disease, Alzheimer's Disease, diabetes, Huntington's Disease, etc.) (FIG. 6).

In one embodiment, PASCs are employed as antigen-specific immunomodulation cells (FIG. 20). Different factors secreted by PASCs (cytokines, growth factors, peptides) could also play a critical role in antigen-specific immunomodulation (FIG. 21).

PASCs significantly improved weight loss and glycemic levels in (i) NODscid diabetic mice and (ii) naturally occurred diabetic mice enhancing the period of survival (FIG. 22-23).

In summary, PASCs can be easily isolated from adipose tissue of any human being (or other mammal) without the use of exogenous genes or cell stress to induce pluripotency. PASCs have the potential to spontaneously differentiate to progenitors and mature cells. Unlike ES and iPSC, it is believed that PASCs can regenerate damaged tissues without forming teratomas.

Advantages of PASCs

Muse cells, another pluripotent stem cells resistant to cellular stress have been isolated be cell sorting, yielding a population of 100% CD105 (+)/SSEA3 (+) cells. Muse cells have been hindered by a low yield from other sources, such as dermal fibroblasts and bone marrow, as Muse cells make up only 1-3% of adult tissue. Furthermore, Muse cell isolation requires not only include cell sorting, but also cell expansion procedures which requires up to 6 weeks to yield 1,000,000 of Muse cells. In contrast, approximately one hundred million PASCs can be extracted from a mere 1-2 liters of tissue, enhancing the number of extractable PASCs without the need for cell expansion procedures and/or cell sorting.

The isolation procedure, typically a 4-8 hrs digestion in a proteolytic enzyme under serum deprivation, low temperatures and severe hypoxia, is both time-efficient and cost-effective, negating the necessity for cell sorting techniques, which require expensive reagents and equipment. The complete process of liposuction, collagen digestion of the aspirated fat, followed by PASC isolation (100,000,000 PASCs/lt of lipoaspirate material), and injection of PASCs (via i.v. or into the damage tissue) requires about 7-9 hours.

This procedure is extremely fast and efficient, offering a particular advantage in cases of acute injury, stroke, massive heart attack, burn, and other urgent conditions in which rapid healing and restoration of function is critical. All procedures can be performed in the same operating room.

Because PASCs are in a dormant stage in both the adipocyte and stromal vascular fractions, interaction of both components (co-culture) is important for the activation and release of PASCs. This phenomenon contributes to the production of very high numbers of PASCs (~100,000,000 PASCs/ltr of lipoaspirate) in a short period of time (6-8 hs). Furthermore, isolation of PASCs form the adipocyte or stromal vascular fraction alone, without co-culture, under the same stress conditions indicated herein, generate a low number of PASCs. Therefore co-culture of adipocyte and stromal vascular fractions is beneficial for producing a large number of PASCs.

PASCs express genes associated with cell death and survival, unlike ASCs, indicating a genetic predisposition to the transition from the quiescent to the active state as a consequence of severe cellular stress. The high Let-7/Lin28 ratio present in PASCs protects these cells from teratogenesis despite their pluripotency. The medial to low expression by PASCs of many genes involved in tissue development, cellular assembly and organization, cellular function and maintenance, DNA replication, repair, and cell cycling, is indicative of their intrinsic lack of tumorigenic susceptibility. Moreover, PASCs express numerous lymphocytic and hematopoietic genes, such as CCR1 and CXCL2, encoding chemokine receptors and ligands known to be involved in stem cell homing.

PASCs likely function according to a highly conserved cellular mechanism related to cell survival in response to severe cellular stress, as well as the functional regeneration of damaged tissues and amputated limbs in primitive species. DNA degradation and mutation contribute to the increasingly harsh milieu of the aging body. As PASCs are inherently resistant to cellular stress, and genetically resilient to DNA damage, their application for the investigation of age-related and degenerative diseases is both relevant and promising.

PASCs have phagocytic activity. Unlike macrophages that phagocytize entire cells, PASCs leave the nucleus of mature cells untouched, which could be used by PASCs as genetic information to generate identical and healthy mature cells. Furthermore, PASCs have the potential to behave as antigen-specific immunomodulation cells by cell to cell contact with B and/T cells. Different factors secreted by PASCs (cytokines, growth factors, peptides) could also play a critical role in antigen-specific immunomodulation.

Figure 24:
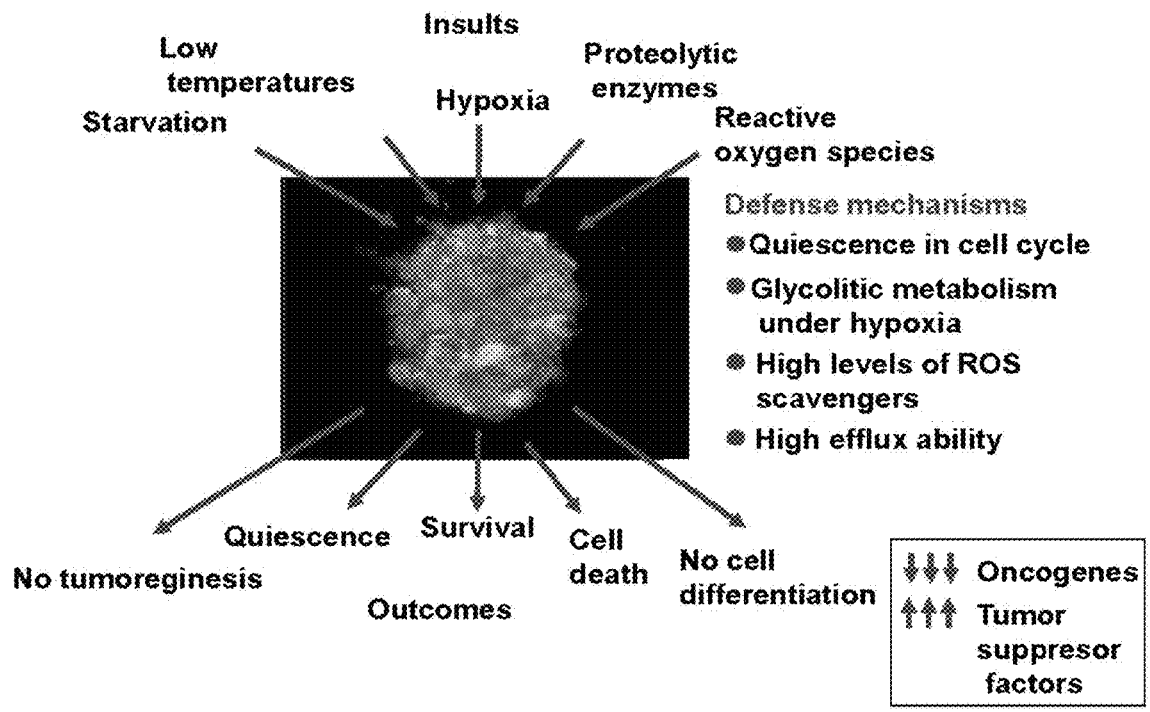
FIG. 24 represents many of the properties of PASCs that make them ideal pluripotent stem cells for tissue regeneration and cell therapy. PASCs are intrinsically present in a quiescent state under normal physiological circumstances within the cellular niche. Multiple adult stem cell lineages have been shown to exist in a quiescent state at various time points throughout their lifespan, including hematopoietic stem cells and epithelial stem cells, which quiescence is thought to play a role in the preservation of their self-renewal. Severe cellular stress (starvation, low temperatures, prolonged incubation with the proteolytic enzyme collagenase) activates PASCs leading to an increase in glycolitic metabolism and high levels of ROS scavengers. Furthermore, PASCs maintains their pluripotency, without undergoing cell proliferation and differentiation. PASCs do not produce teratomas in vivo due to in part their low level of expression of oncogenes coupled with high expression of tumor suppressor Finally, due to their high resistance to cellular stress, PASCs have a high degree of survival and regenerate damaged tissue with very high efficiency.

PASCs, are intrinsically present in a quiescent state under normal physiological circumstances within the cellular niche (34-35). Multiple adult stem cell lineages have been shown to exist in a quiescent state at various time points throughout their lifespan, including hematopoietic stem cells and epithelial stem cells, which allegedly plays a role in the preservation of their self-renewal (34, 35). Severe cellular stress (starvation, low temperatures, prolonged incubation with the proteolytic enzyme collagenase) activates PASCs leading to an increase in glycolitic metabolism and high levels of ROS scavengers. Furthermore, PASCs maintain their pluripotency, without undergoing cell proliferation and differentiation. PASCs do not produce teratomas in vivo, likely due to their low level of oncogene expression tumor and high level of tumor suppressor factors expression. Finally, PASCs due to their high resistance to cellular stress, have a high degree of survival and regenerate damage tissue with very high efficiency (FIG. 24).

Figure 25:
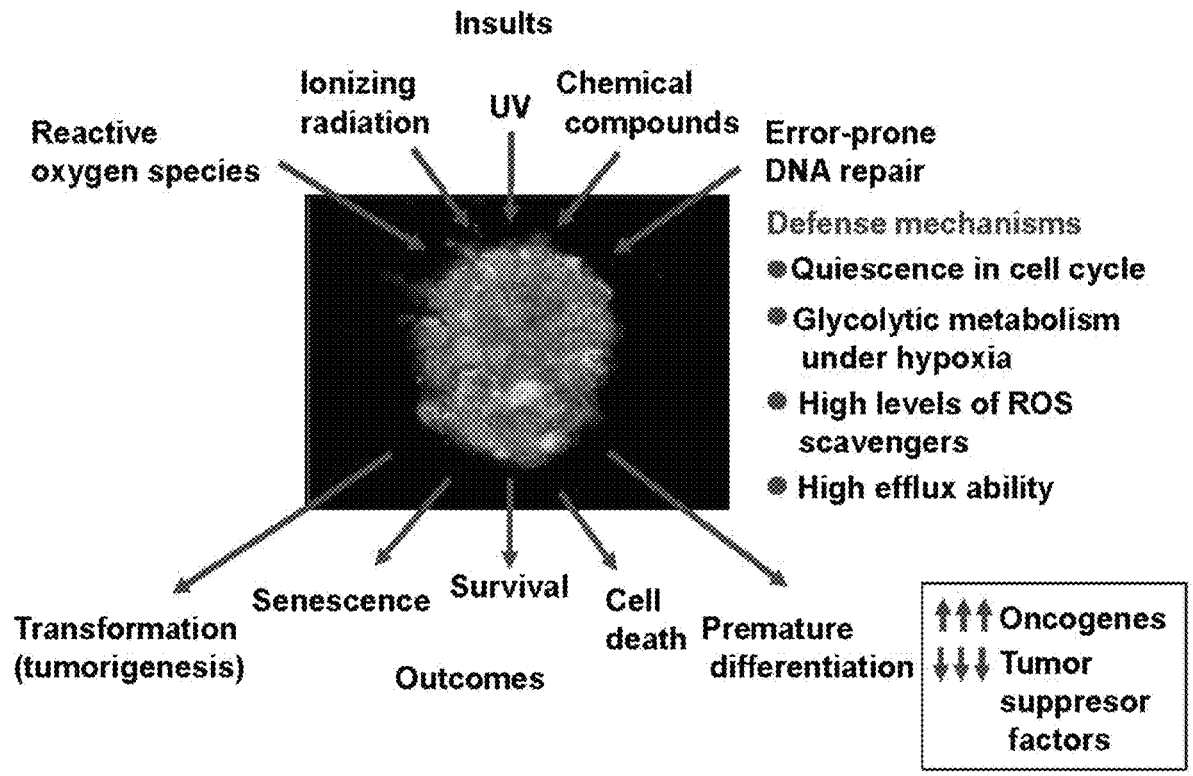
FIG. 25 illustrates the potential of PASCs to become cancer stem cells (CSCs) if they are activated under abnormal stress conditions (e.g. ionizing radiation, ultraviolet light, chemical compounds, error-prone DNA repair, etc). Similarly, programming PASCs with the Yamanaka's factors lead with the formation of iPS cells (cells with teratogenic potential). It may be possible to activate endogenous PASCs, which could account for the small population of cells that are converted into iPS cells. Such a theory is supported by previous studies regarding the possible role of adult organ-specific positive Oct4 (+) stem cells during asymmetric division in the generation of cancer cells. CSCs may potentially be generated by PASCs under abnormal stimulus. They may divide very quickly, with a very active glycolytic metabolism. CSCs can stimulate premature differentiation, cellular death, increase oncogene expression and exhibit low expression of tumor suppressor driving tumor growth. Furthermore, potential CSCs derived PASCs are resistant to chemo- and radiotherapy and are responsible for its relapse after treatment.

If cellular stress is performed under carcinogenic stress conditions (e.g. ionizing radiation, ultraviolet light, chemical compounds, error-prone DNA repair, etc), PASCs have the potential to become cancer stem cells (CSCs). For example, Muse cells (CD105 (+)/SSEA3 (+)) that are like PASCs are resistant to cellular stress. Programming of Muse cells by the introduction of the four Yamanaka's factors led to the formation of iPS (cells with tumorigenic activity). It may be possible to abnormal activation of endogenous Muse cells which account for the small population of cells that are converted into iPS cells (23). Such a theory is supported by previous studies regarding the possible role of adult organ-specific positive Oct4 (+) stem cells during asymmetric division in the generation of cancer cells (15). Similarly to Muse cells, PASCs could have the potential to be converted to CSCs under tumorigenic stimulus. Under these circumstances, PASCs could divide very fast, with a very active glycolytic metabolism and differentiate into CSCs. CSC derived from PASCs would have high differentiation, increase in oncogene expression and low expression of tumor suppressor factors driving tumor growth. Furthermore, CSCs derived PASCs could be resistant to chemo- and radiotherapy and be responsible for its relapse after treatment (FIG. 25). PASCs therefore provide a tool for the development of cancer therapies, specifically with regards to identification of agents for modulation of cancer stem cells, quiescence, malignancy and post-treatment relapse.

The methods and isolated cells described herein offer the following features: (i) it is possible to easily isolate pluripotent stem cells (PASCs) from both the adipocyte and stromal vascular fractions under severe stress conditions; co-culture between both fractions is beneficial for the production of large amounts of PASCs (100,000,000 PASCS/lt of lipoaspirate); (ii) a significant amount of PASCs, as individual cells and associated in clusters, can be isolated from both the adipocyte and stromal vascular fractions; (iii) hundreds of clusters containing thousands of PASCs can be obtained from a relatively small amount of adipose tissue; (iv) harvesting adipose tissue is a safe and non-invasive procedure; (v) from 200-2000 cc of lipoaspirate material obtained under local anesthesia, it is possible to isolate 20,000,000-200,000,000 PASCs; (vi) from the same preparation, it is also possible to isolate ADSCs from the stromal vascular fraction (e. g. ~200,000,000 ADSCs/liter of lipoaspirate material); (vii) clusters of PASCs can be formed within hours, of harvesting the lipoaspirate material; (viii) PASCs can be maintained in an undifferentiated state by culturing the cells for many days using non-adherent culture dishes; (ix) progenitors derived from PASCs can be isolated by culturing clusters of PASCs in adherent culture dishes; and (x) mature cells from the three germ layers (endodermal, ectodermal and mesodermal) can be also obtained with low efficiency (20%) by keeping the cluster of cells in culture for an extended time in adherent culture dishes; mature cells derived from PASCs can be obtained with very high efficiency (80-90%) by keeping clusters of PASCs in specific induced differentiation medium.

In summary, PASCs can be easily isolated with a high degree of purity without the need of using cell sorting or other methods for cell enrichment that could change the phenotype of PASCs. PASCs can differentiate to progenitors and mature cells, in a spontaneous process without and with the use of an induced differentiation medium. PASCs, unlike ESCs and iPSCs offer the capability to repair and regenerate in vivo damaged tissue without forming teratomas.

In addition, it is noted that various advantages of the methods described herein include, but are not limited to:
  (1) Harvesting pluripotent stem cells from adipose tissue by lipoaspiration is less painful than harvesting these cells from bone marrow cells;
  (2) PASCs are spontaneously originated with stress cell treatment and many clusters of PASCs can be formed from small amount of adipose tissue;
  (3) Many PASCs can be highly purified by a simple technique in a very short period of time without the need of cell sorting or other cell selection technique;
  (4) Because the quick procedure of cell isolation and high yield, PASCs can be reinjected into the patient without the need of cell expansion;
  (5) Alternatively, PASCs can be keep in culture and expanded following standard cell culture techniques;
  (6) It is possible to isolate (i) PASCs, (ii) progenitors derived from PASCs and (iii) mature cells derived from PASCs which allows cell therapy using either of PASCs/progenitors/mature cells; and
  (7) It is possible to screen new drugs using PASCs at different stage of cell differentiation.

Role of PASCs in Cancer

Tumor growth may be driven by a small population of cells with self-renewal capacity and high tumorigenic potency. These cells are called cancer initiating or cancer stem cells (CSCs). These cells are more resistant to chemo- and radiotherapy, as well as environmental factors, They sustain tumor growth and are responsible for its relapse after treatment. PASCs are highly resistant to cellular stress, and allow for isolation and characterization of such an endogenous cell population that displays cancer like resistance (FIG. 25). Furthermore, microarray data indicate activation of over half a dozen proto-oncogenes that are slightly overexpressed in PASCs relative to ADSCs. The level of expression of these proto-oncogenes would be expressed at significantly lower levels (several orders of magnitude) in PASCs compared to pluripotent embryonic stem cells and induced pluripotent stem cells (iPS) (23).

Conversion of PASCs into cancer stem cells (CSCs) can be induced if PASCs are activated under carcinogenic stress conditions (e.g. ionizing radiation, ultraviolet light, chemical compounds, error-prone DNA repair, etc). Similarly, programming PASCs with Oct4 (Pou5f1), Sox2, cMyc, and Klf4 (Yamanaka's factors) lead to the formation of iPS (cells with teratogenic potential) (FIG. 25).

Figure 16:
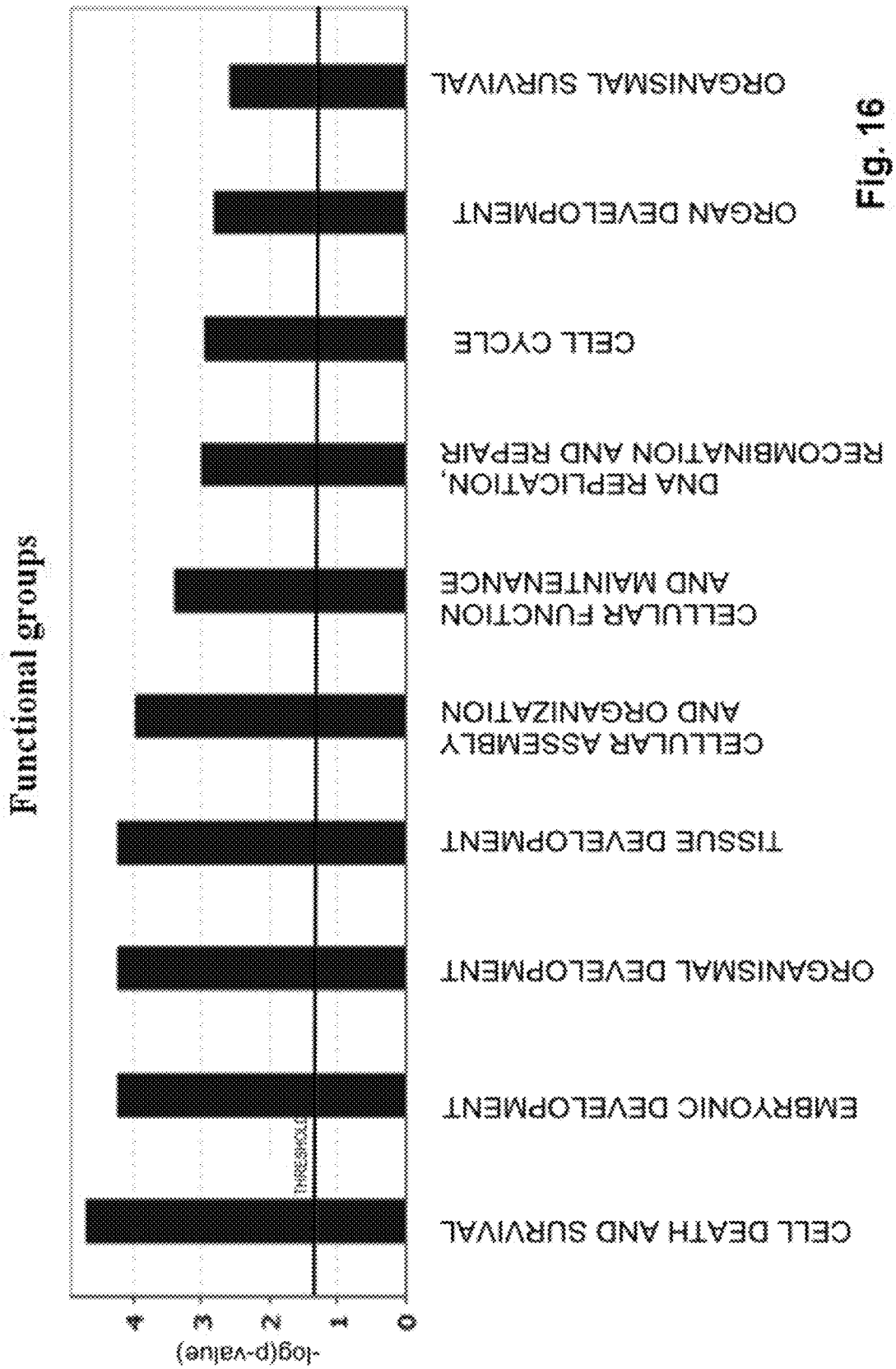
FIG. 16 indicates the top ten functional groups pathways of all differentially expressed genes (2 fold or higher) in PASCs versus ADSCs. Fischer's exact test was used to calculate a p-value determining the probability of the association between the genes in the data set with functional groups. Functional groups are displayed along the x-axis, while the y-axis displays logarithm of p values calculated by Fisher exact between the ratio of the number of genes differentially expressed genes (2 fold or higher) in PASCs vs ADSCs in a given functional group divided by total number of genes that make up that functional group or pathway with a threshold for statistical significance set at 0.05. The analysis was performed by Ingenuity Pathways analysis software.
Figure 17:
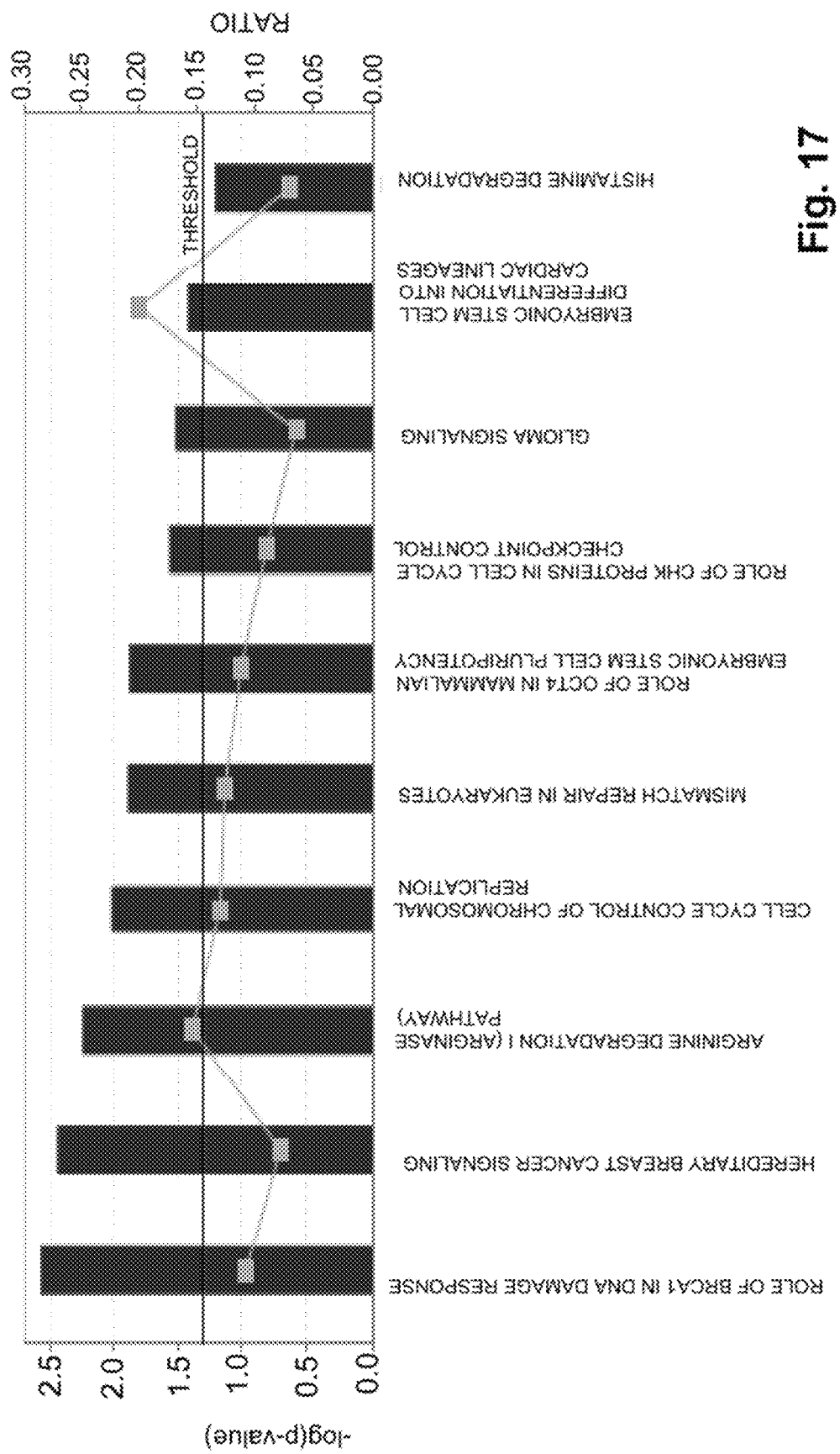
FIG. 17 indicates the top ten canonical pathways of all differentially expressed genes (2 fold or higher) in PASCs vs ADSCs. Fischer's exact test was used to calculate a p-value determining the probability of the association between the genes in the data set with canonical pathways. Canonical pathways are displayed along the x-axis, while the y-axis displays logarithm of p values calculated by Fisher exact between the ratio of the number of genes differentially expressed genes (2 fold or higher) in PASCs vs ADSCs in a given canonical pathway divided by total number of genes that make up that canonical pathway with a threshold for statistical significance set at 0.05. The analysis was performed by Ingenuity Pathways analysis software.

Canonical pathways include the role of Oct4 in embryonic stem cell pluripotency, BRCA1 in DNA damage and hereditary breast cancer signaling, cell cycle control of chromosomal replication, DNA repair, arginine degradation, and embryonic stem cell differentiation into cardiac lineages. These data provide further insight into the role of PASCs in DNA repair, cell cycle, oxidative stress, cancer cell regulation, as well as their intrinsic pluripotency (FIGS. 16-17).

This cell type, as isolated and activated by these techniques would allow for: (1) early detection and identification of CSCs for more accurate and earlier diagnosis; (2) a model for study of CSCs using endogenous and non-manipulated cells, ideal for use in high-throughput applications, and used to develop biomarkers for detection, as well as drugs and chemotherapeutic approaches for treatments; (3) controlling these cells, via understanding inherent activation and their role in a healthy human stem cell niche, leading to new approaches to inducing these cells' natural resting or senescent state. This resting state provides a pool of cells that can be used and activated for tissue repair of damaged endodermal, ectodermal, and mesodermal cell lineages. Unlike iPC, these cells have active tumor suppressors, and precursor proto-oncogenes (rather than induced oncogenes) making them much more suitable for safe use in regenerative applications, once properly differentiated.

Role of PASCs in Human Reproduction

A significant cause of infertility is reduced mitochondrial functionality in the oocytes of women undergoing in vitro fertilization (IVF) therapy. PASCs normally exist in a quiescent state and are activated by severe cellular stress. PASCs are inherently resilient to the growing environmental hostility of an advanced maternal age (AMA) ovary, in which oocyte mitochondria are highly susceptible to the detrimental effects of hypoxia and apoptosis. PASCs could therefore contribute to autologous mitochondrial transfer to oocytes of AMA women with infertility due to their intrinsic stress endurance and potential to adopt the germ cell lineage. This would avoid the deleterious heterogeneity that has arisen in previous trials with third-party and somatic cell transfers.

PASCs can be isolated from adipose tissue from a young female with healthy mitochondria, or from a sibling or mother with identical mitochondria. This source of healthy mitochondria can be used as a treatment in one of two ways: (1) by transferring healthy PASC mitochondria to the oocyte that will be fertilized, or (2) by differentiating the healthy PASCs to an oocyte phenotype and swapping out the "donor" PASC nucleus (that has healthy mitochondria in the cytoplasm) with the nucleus of the oocyte with dysfunctional mitochondria.

Furthermore, as inherent oocyte production in the mammalian female terminates at birth, excessive depletion of the existing pool of follicles due to reproductive abnormalities is essentially irreparable in vivo. Generation of human oocytes derived from PASCs offers a means of autologous transplantation to provide functional oocytes for common causes of infertility, including premature ovarian failure, reproductive aging associated with delayed childbearing, and poor oocyte quality, which can occur even in young women. In addition, the study of induced gametogenesis and oocyte generation from PASCs can provide further insight into the biological mechanisms of mammalian gametogenesis and the female reproductive function in its entirety.

The foregoing methods are intended to be illustrative and not limiting. Using the teaching provided herein, other methods of isolating and using PASCs will be available to one of skill in the art.

Examples

The following examples are presented to illustrate the present invention and to assist one of ordinary skill in making and using the same. The examples are not intended in any way to otherwise limit the scope of the invention.

Example 1: Isolation and Characterization of PASCs

Figure 9A:
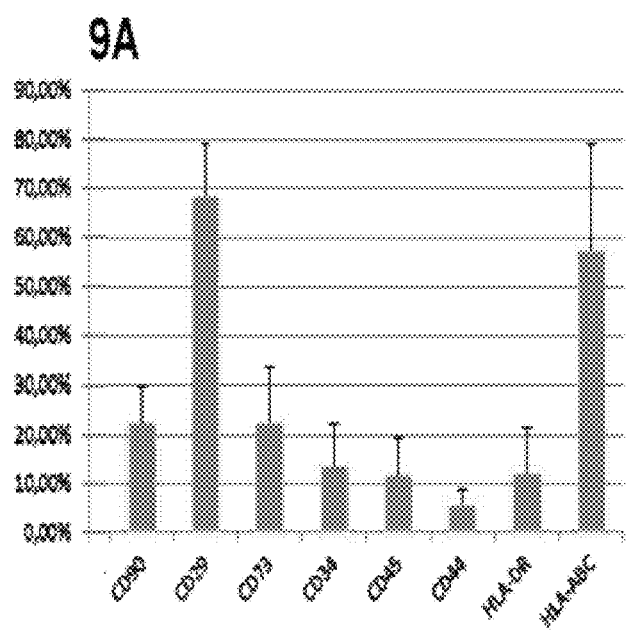
FIGS. 9A-9B show flow cytometry analysis of surface protein expression for clusters of differentiation (CD) markers in PASCs. PASCs were characterized by using the following CD markers: CD105 (marker of mesenchymal stem cells), CD29 (marker for T cells), CD90 (marker for thymocytes), CD73 (marker for lymphocyte differentiation), CD34 (marker for hematopoietic stem cells), CD45 (marker for hematopoietic stem cells), CD44 (marker for activated T lymphocytes), HLA-DR (marker for HLA class I) and HLA-DR (marker for HLA class II). (9A) Graphic bar represents the percentage of expression of surface markers on Muse Cells. (9B) Representative histograms of some clusters of differentiation (CD).
Figure 9B:
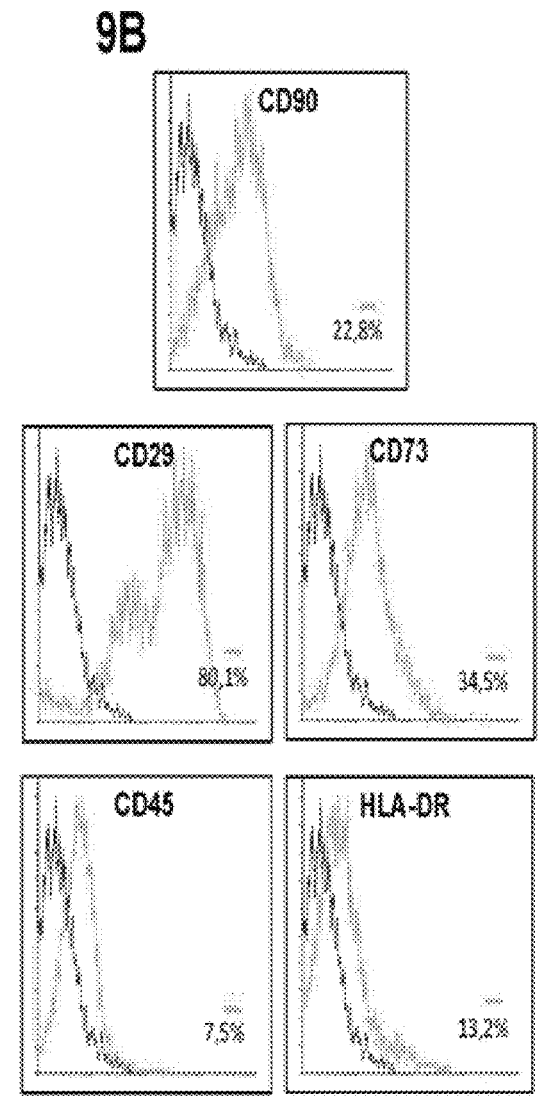

This example describes the isolation and characterization of PASCs. In summary, the example shows the following: PASCs can grow in suspension as individual cells and cell spheres reminiscent of embryonic stem cell clusters, and have the capacity for self renewal, yet grow at a moderate rate (FIG. 7) Karyotype studies indicate that PASCs have 23 pair of chromosomes which show normal integrity (FIG. 8) A small percentage of PASCs (10-20%) can be recognized by CD90 (marker for thymocytes), CD73 (marker for lymphocyte differentiation), CD34 (marker for hematopoietic stem cells), CD45 (marker for hematopoietic stem cells), CD44 (marker for activated T lymphocytes), and HLA-DR (marker for HLA class II) (FIG. 9A-B). In contrast, 60-70% of PASCs were recognized by CD105, CD29 (marker for T cells) and HLA-ABC (marker for HLA class I) (FIG. 9A-B). These results confirm that PASCs have the potential to be used in cell therapy for allotransplantation open the possibility of PASC cell transplantation between different individuals without immunorejection. Furthermore, these results clearly indicate the phenotypic differences between PASCs and Muse cells, another pluripotent stem cell resistant to cellular stress and isolated by CD105/SSEA3 cell sorting.

Figure 10A:
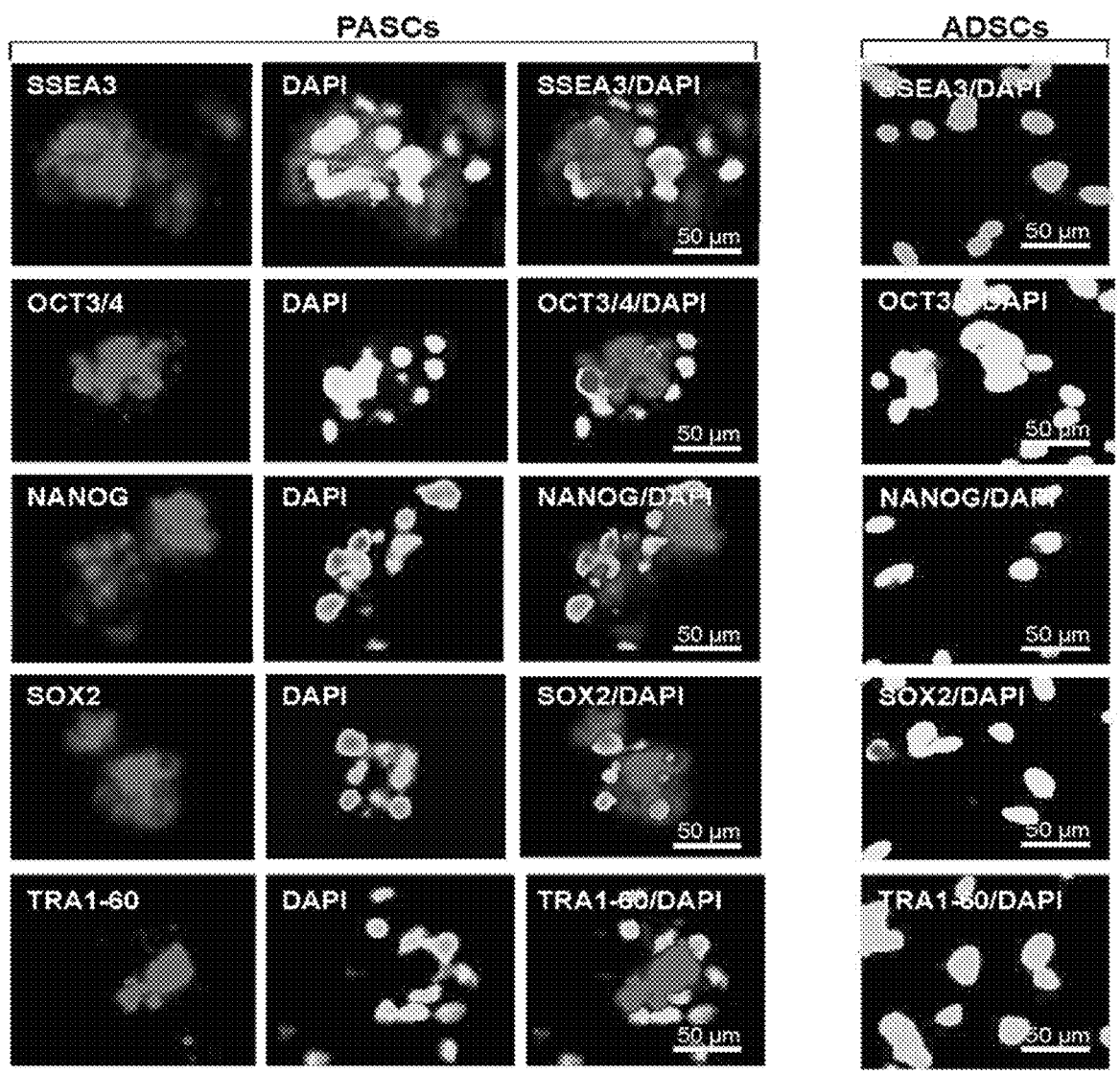
FIG. 10A indicates that PASCs form aggregates, along with individual cells, both expressing characteristic pluripotent stem cell markers (SSEA3, Oct3/4, Nanog, Sox2 and TR1-60), ADSCs were used as negative controls.
Figure 10B:
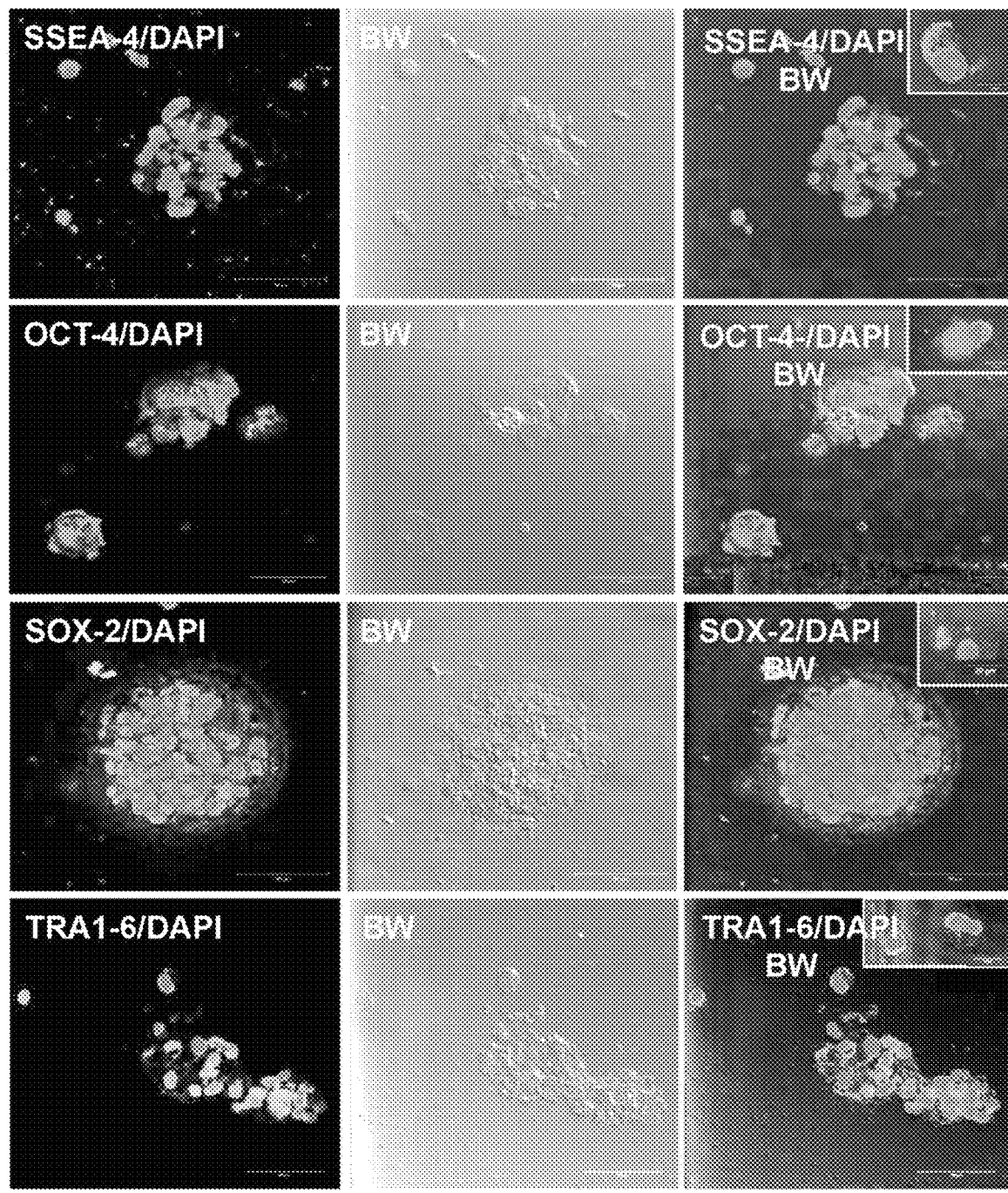
FIG. 10B indicates that all cells surviving the severe cellular stress treatment are indeed PASCs (see recognition of all cells by the pluripotent stem cell markers SSEA4, Oct3/4, Sox2 and TRA1-60 (see overlap between pluripotent stem cell markers, DAPI and total cells detected by light microscopy, BW).
Figure 11A:
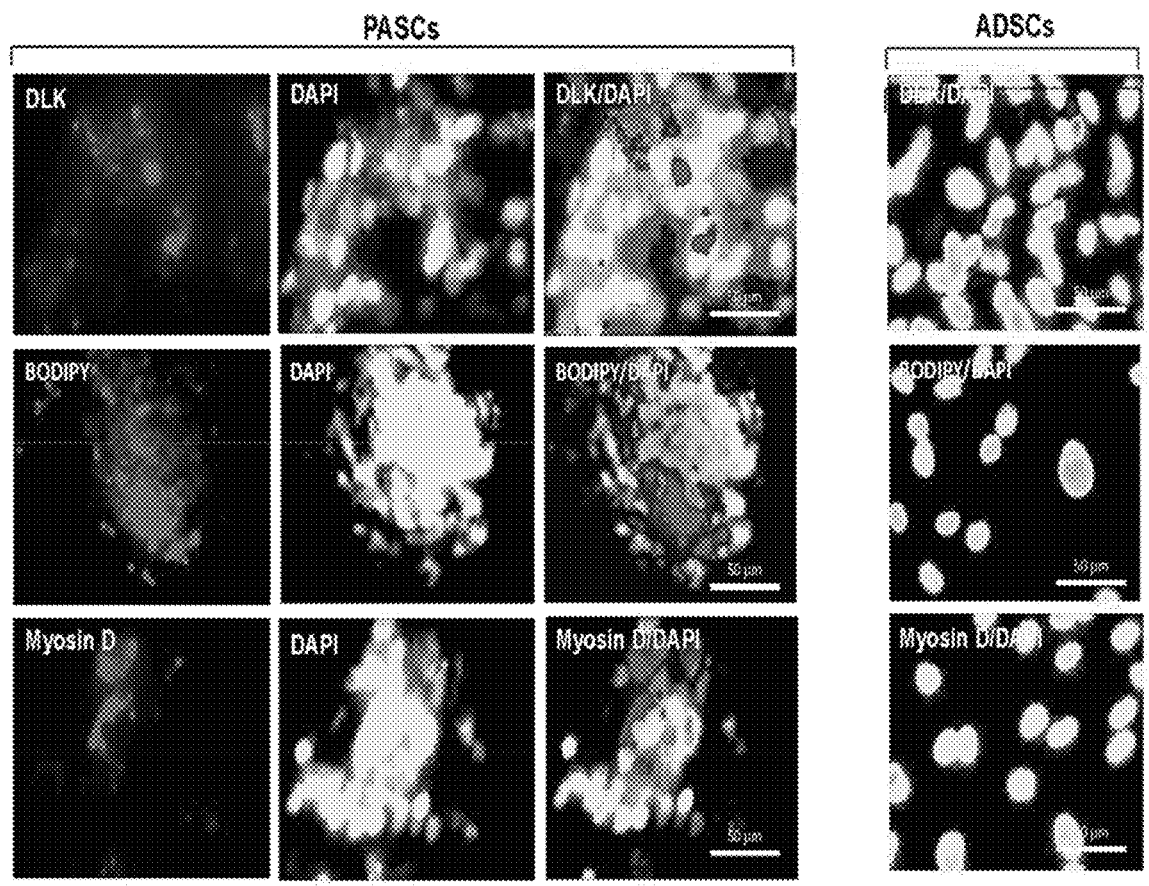
FIGS. 11A-11C show PASC differentiation into mesodermal cell lineages. (11A) Spontaneous differentiation of PASCs into a mesodermal lineage was determined by using antibodies to DLK (marker for preadipocytes, BODIPY-$C_{16}$ (fluorescent dye to detect lipid accumulation), and myosin D Heavy Chain) (marker for the heavy chain portion of the Myosin II protein found in skeletal muscle cells). (11B) PASC differentiation to adipocytes in adipogenic medium (3 and 6 days). Lipid accumulation of newly formed adipocytes was detected using BODIPY-$C_{16}$. (11C) PASC differentiation to myocytes in myogenic medium (3 and 6 days). Smooth muscle cells were detected using SMA antibody. ADSCs were used as controls.
Figure 11B:
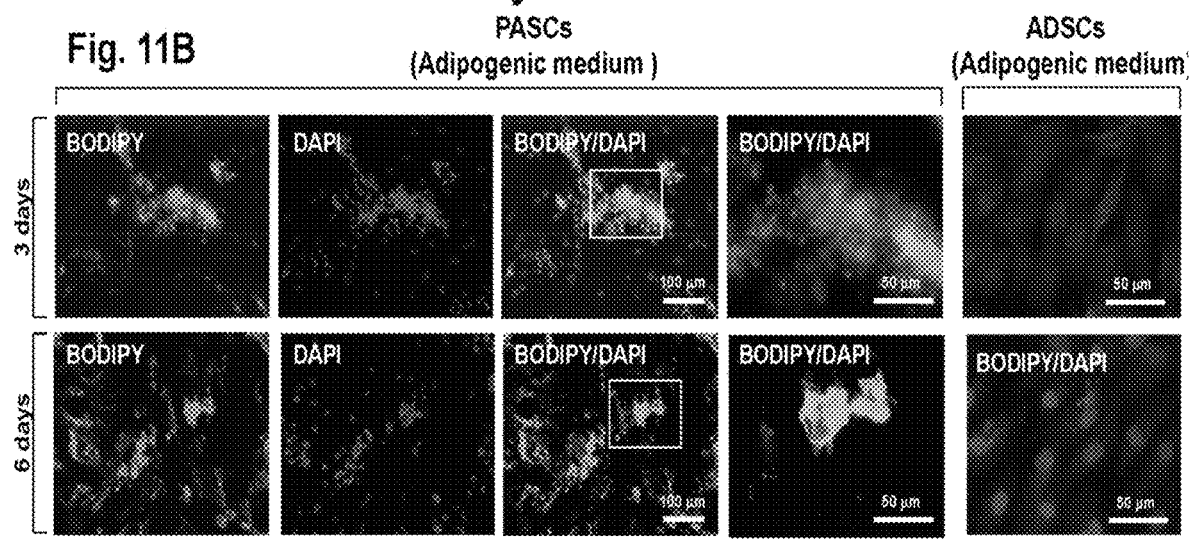
Figure 11C:
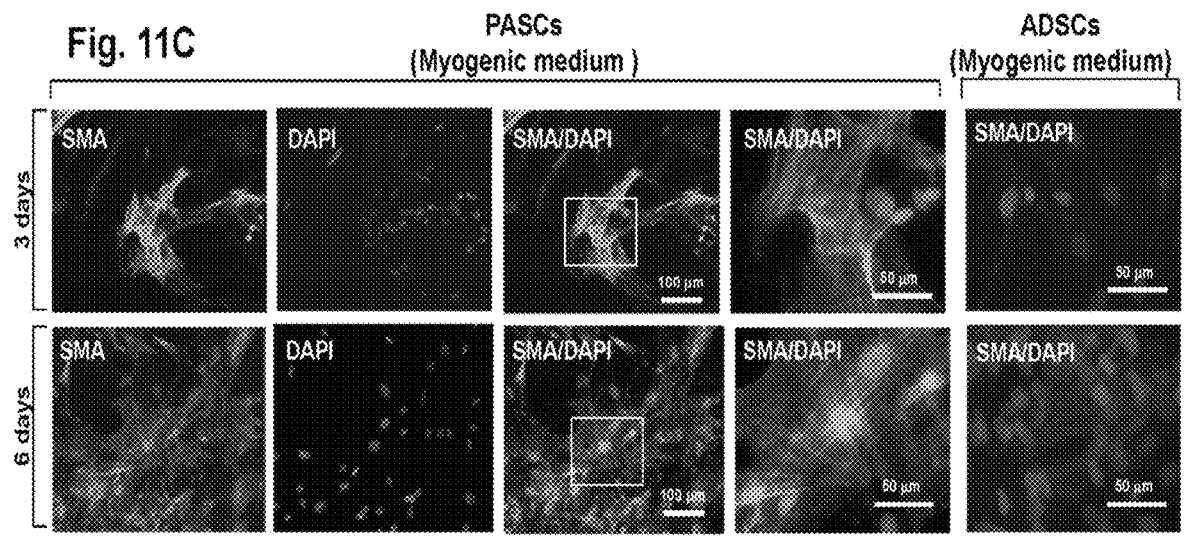
Figure 13A:
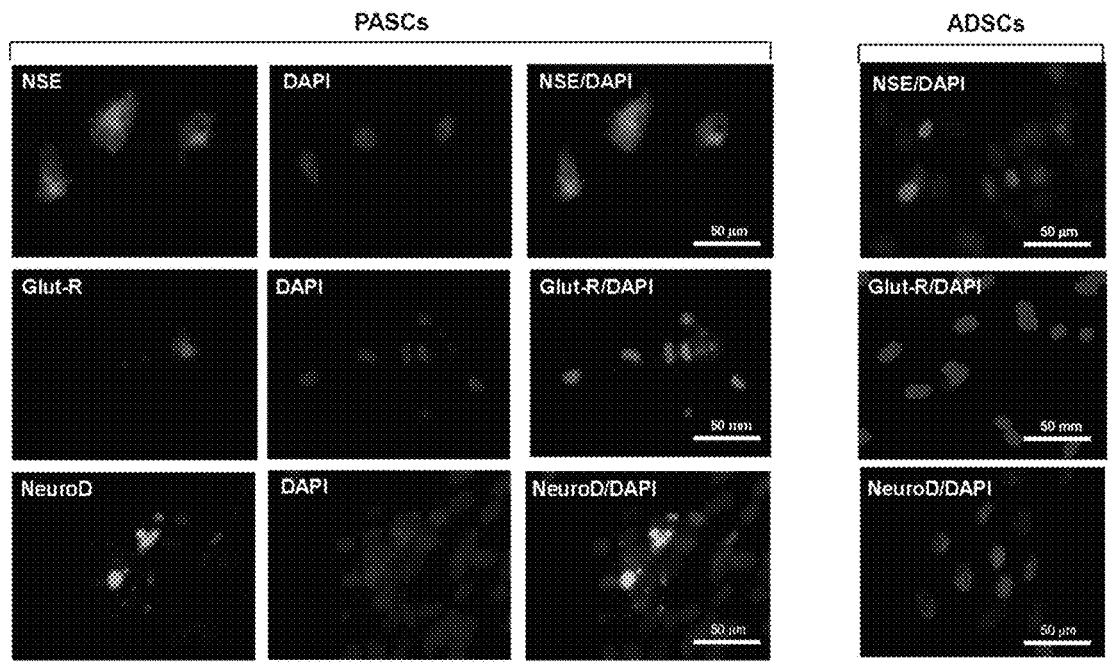
FIGS. 13A-13C illustrate PASC differentiation to ectodermal cell lineages. (13A) Spontaneous differentiation of PASCs into ectodermal cell lineages was determined using antibodies to neuron-specific enolase (NSE, a marker used to detect neocortical neuron progenitors), metabrotopic-glutamate receptor (Glut-R, a marker used to detect microglial and neural like cells) and NeuroD (a marker used to detect neocortical precursor cells). (13B) Morphological progression of PASCs into neurons throughout the incubations in both the first and second neurogenic differential mediums. PASCs exhibited a progression from the formation of large cell spheres with finger-like projections to long, neuron-like cells, which subsequently formed large networks. (13C) Neural cells derived from PASC were generated after incubation of PASCs in both first and second neurogenic differential medium. Neural like cells were characterized using nestin (marker of neural progenitor cell) and MAP2 (marker involved in the polymerization of microtubules). ADSCs were used as controls.
Figure 13B:
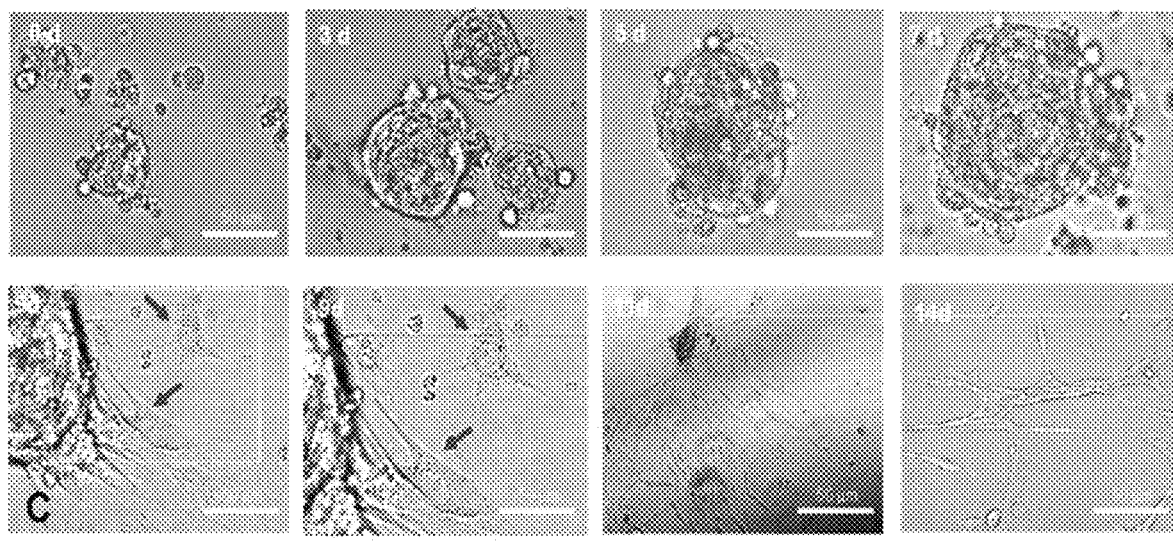
Figure 18:
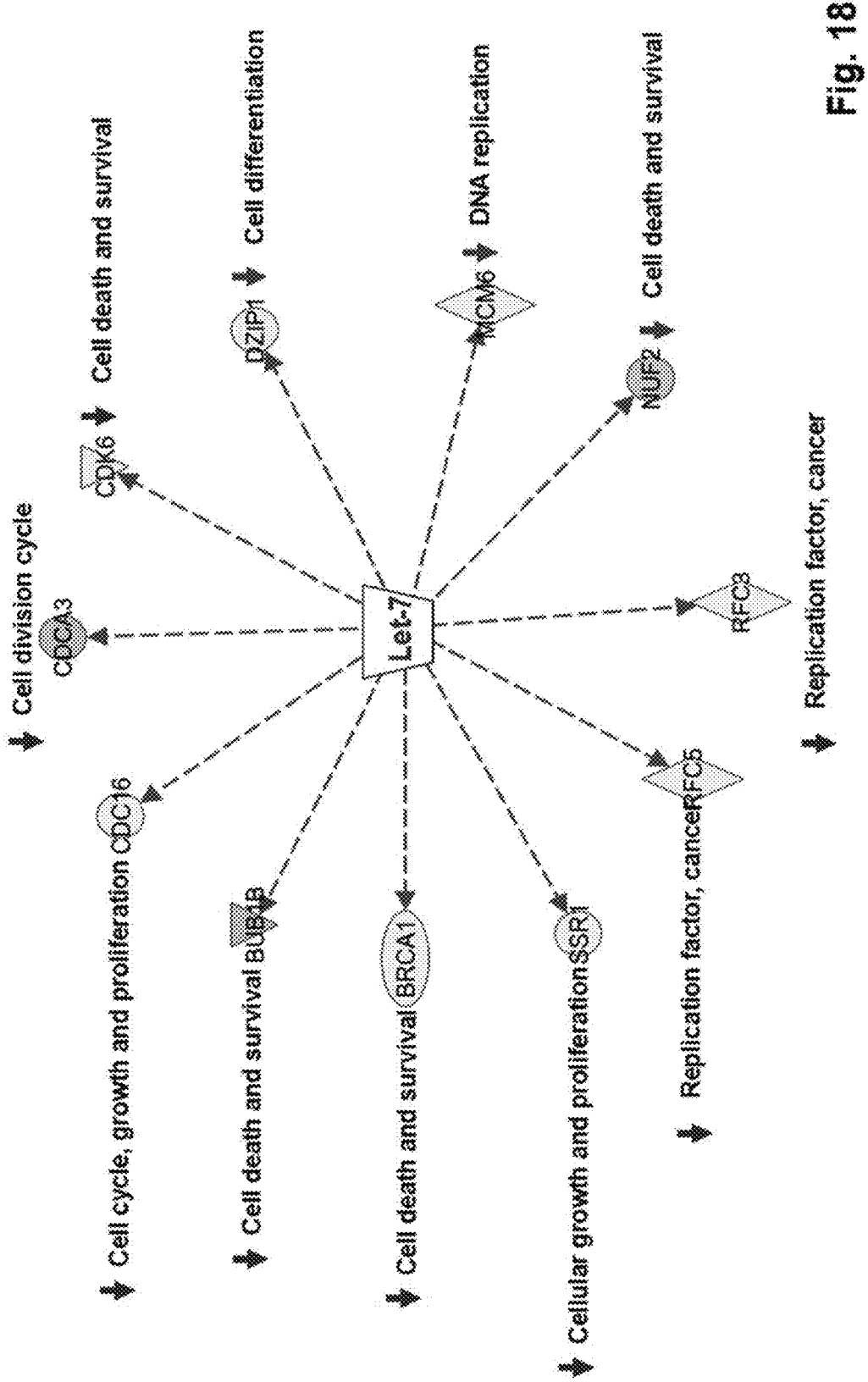
FIG. 18 shows that MicroRNA Let-7 is the most significant upstream regulator present in PASCs versus ADSCs. Let-7 regulates 11 downstream genes associated with decrease of cell cycle division (e.g. CDCA3, CDC16), cell differentiation (DZIP1), cellular growth and proliferation (SSR1), DNA replication (MCM6), replication factor and cancer (RFC3, RFC5) and cell death and survival (NUF2, BRCA1, BUB1B, CDC16. Over-expression of Let-7 in PASCs would potentially play a critical role in inhibiting Lin28 expression, and therefore would protect these cells from tumorigenic proliferation and teratoma formation.

In addition, PASCs are positive for the pluripotency markers SSEA3, TR-1-60, Oct3/4, Nanog and Sox2 (FIGS. 10A-B), and can spontaneously differentiate into mesenchymal, endodermal and ectodermal cell lineages with an efficiency between 20-23% (FIGS. 11A, 12A, 13A). In the presence of specific differentiation media, PASCs can be induced to mesenchymal, endodermal and ectodermal with an efficiency between 78-82%. (FIGS. 11B-C, 12B, 13B-C). While regular ASCs require 14-17 days of treatment in adipogenic medium to become adipocytes, PASCs can be rapidly converted to adipocytes like cells by only 5 days of treatment in adipogenic medium (FIG. 11B). And while regular ASCs require 21 days of treatment in myogenic medium to become myocytes, PASCs can be rapidly converted to myocyte like cells with only 5 days of treatment in myogenic medium (FIG. 11C). PASCs do not undergo cell proliferation or tumor formation, setting them apart from ES and iPS cells. At 4 months after transplantation into the testes of immune-deficient mice, PASCs ($10^6$ cells/mouse) did not form teratomas. In contrast, the tumorigenic cell line F19 formed teratomas at 3 weeks-post injection (FIG. 14). MicroRNA Let-7 is the most significant upstream regulator present in PASCs vs ASCs (FIG. 18). Lin28, a RNA-binding protein gene, maintains both pluripotency and tumorigenesis in ES and iPS cells. Over-expression of Let-7 in Muse cells would potentially play a critical role in inhibiting Lin28 expression, and therefore would protect these cells from tumorigenic proliferation and teratoma formation.

PASCs have a very low level of cell division and proliferation, without tumorigenic activity. In contrast, PASCs exhibit a very high level of expression of genes associated with immunity, inflammation, immune response, immune suppression, lymphocyte activation and T cell activation, suggesting a role for PASCs in dendritic cells or T-helper cells at the site of an infection (FIG. 15).

Figures 19A, 19B, 19C:
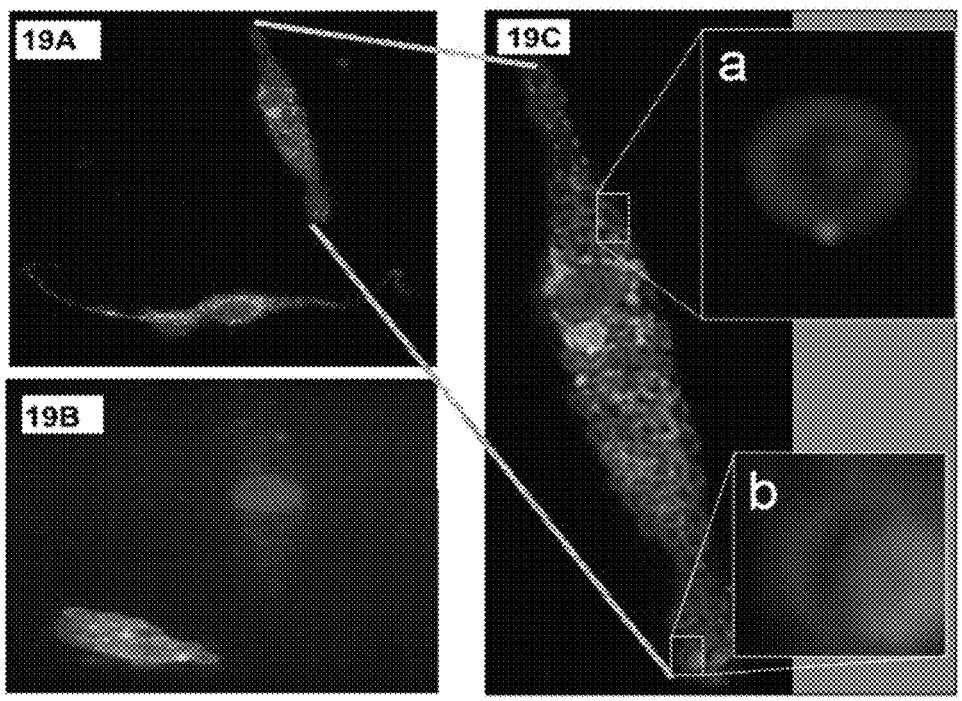
FIGS. 19A-19C show that PASCs have phagocytic activity. Formation of PASCs were detected after co-culture of adipocyte fraction (floating cells) and the stromal vascular fraction (adherent cells). There is a clear interaction between preadipocytes (S-100 (+) cells) and PASCs indicating by (CD34(+) cells, marker of hematopoietic stem cells) which could be the smallest and most primitive PASCs that appear to be formed. (19A) PASCs are firmly attach to approximately a third of the preadipocytes. This attachment is apparently selective since seemingly identical preadipocyte cells are completely engulfed in PASCs. (19B) Preadipocyte undergoing mitosis left undisturbed by PASCs while the preadipocyte directly above is engulfed by PASCs leaving only the DAPI positive nucleus uncovered. While both preadipocytes and PASCs are S-100+ and SSEA3, (FIG. 19C-a, 19C-b) indicate that peadipocytes would show positive S-100 staining with fluorescent light exposure of 1-2 seconds, with PASCs would display positive results with only a 1 millisecond exposure time. The great discrepancy in exposure strengths suggests that the PASCs express S-100 at much higher levels, or more readily allows S-100 anti-body bind to its domain. Individual PASCs were originally identified through the clear DAPI staining of their small nuclei. The preadipocytes could clearly be seen at different stages of being phagocytized. Unlike macrophages that phagocytize entire cells, PASCs leave the nucleus of preadipocytes untouched, (FIG. 19A) often times resulting in preadipocyte nuclei that are left bare in culture (FIG. 19B).

Microarray data indicate a substantial up-regulation of Sox2, Oct3/4, and Rex1 in PASCs relative to ADSCs. PASCs also exhibit gene expression patterns associated with the down-regulation of genes involved in cell death and survival, embryonic development, DNA replication and repair, cell cycle and potential factors related to oncogenicity. Gene expression analysis indicates that PASCs and ADSCs are mesenchymal in origin; however, PASCs also express numerous lymphocytic and hematopoietic genes, such as CCR1 and CXCL2, encoding chemokine receptors and ligands involved in stem cell homing. Gene ontology analysis of PASCs vs ASCs indicate that the most statistically significant categories of cellular functions include cell death and survival, embryonic development, tissue development, cellular assembly and organization, cellular function and maintenance, DNA replication, recombination and repair, cell cycle, organ development and organismal survival (FIG. 16). Canonical pathways provide further insight into the potential role PASCs in DNA repair, cell cycle, oxidative stress, cancer cell regulation, as well as their intrinsic pluripotency (FIG. 17). In addition, PASCs exhibit phagocytic activity. Unlike macrophages that phagocytize entire cells, PASCs leave the nucleus of mature cells untouched, which could be used by PASCs as genetic information to generate identical and healthy mature cells (FIG. 19)

Materials and Methods

Isolation of PASCs from Lipoaspirated Fat

Lipoaspirates (50 ml-2000 ml) were obtained from subcutaneous abdominal adipose of women undergoing liposuction. Lipoaspirate was repeatedly washed with PBS until blood was completely removed from the tissue. 50 ml-2000 ml of lipoaspirate was mixed with equal volume Dulbecco's Modified Eagle Medium 1× (DMEM, CellGro, MediatechInc, Manassas, VA) containing collagenase (0.1%, Sigma Aldrich) in 50 ml tubes and incubated for 30 min at 37° C. in a shaking incubator at 110 rpm. If adipose tissue was not completely digested the incubation was continued under the same conditions for additional 10-15 more minutes, followed by incubation in 4° C., while still in collagenase and nutritionally deficient medium (no FCS), for 6 hours. For this, the 50 ml tubes were transferred to a regular 4° C. refrigerator allowing the temperature to slowly drop from 37° C. to 4° C. Under these severe cellular stress conditions (prolonged collagenase incubation, lack of nutrients, low temperatures and high hypoxia) all cells present in the lipoaspirate digested material died, except PASCs highly resistant to such stress. Digested material was then centrifuged at 1500 rpm for 10 minutes at 4° C. Supernatant containing adipose cell debris (dead adipocytes, macrophages, red blood cells, adipose stem cells among other cell components) was removed by aspiration and the remaining cell pellets were combined and transferred to a new 50 ml tube. Cell pellet was then washed three times with 25 ml DMEM each time to assure that all collagenase was completely removed from cell pellet. Cell were re-suspended in DMEM comprised of 10% fetal bovine serum (FBS; Thermo Scientific Hyclone, Logan, UT) and 5% antibiotic-antimycotic solution (CellGro, Mediatech Inc, Manassas, VA), and plated as cells in suspension as well as adherent cells to further characterize the purity and pluripotency of PASCs. If PASCs will be injected in an animal model, freshly isolated PASCs will be resuspended in a small volume of saline solution and directly injected into the damaged area or via i.v. following standard protocols.

Cell Expansion, Clonality and Karytotype of PASCs

Cell expansion and clonality of PASCs were determined after 8 different passages. Cell clusters spheres were formed after few hours of plating freshly isolated PASCs in non-adherent dish ($1^{st}$ generation). Once, most of cell spheres reached a size >50 μm, cell clusters were disaggregated by pipetting and transfer to a new non-adherent dish ($2^{nd}$ generation). PASCs were grown forming new cell-clusters as before with a growth rate of 1½ days/cell division ($3^{rd}$ generation). The karyotypes of all expanded cells were determined by quinacrine-Hoechst staining following standard protocols.

Flow Cytometry Analysis

Floating PASCs were cultured in DMEM/10% FCS for 8 hours followed by FACS analysis. Cells were washed in 2% inactivate FCS/0.05% sodium Azide/PBS and were re-suspended in 100 μl of the same buffer and incubated at 4° C. for 1 hour in the presence or absence of primary unconjugated rat anti-human SSEA3 (EMD Millipore; Billerica, Massachusetts). Cells were then washed twice with the same buffer and incubated with the corresponding secondary FITC-conjugated anti-rat IgM (BD Biosciences; San Diego, CA) for 45 minutes at 4° C. Cells were then washed and re-suspended in 200 μl of the same buffer. Analysis of count and cell type was performed using a FACS Calibur flow cytometer and cEllQuest Pro software. For further characterize PASCs, other markers, such as CD105 (marker of mesenchymal stem cells), CD90 (marker for thymocytes), CD73 (marker for lymphocyte differentiation), CD34 (marker for hematopoietic stem cells), CD45 (marker for hematopoietic stem cells), CD44 (marker for activated T lymphocytes), HLA-DR (marker for HLA class II) were used for FACS following standard protocols.

Immunocytochemistry

Cells were fixed in 4% paraformaldehyde (20 min at R/T), washed in PBS, then incubated in 0.2% Triton for 20 min. After 2 successive washes in PBS, cells were blocked with 10% normal goat serum in 1% BSA solution for 60 min at R/T. Cells were then incubated with the primary antibodies overnight at 4° C. The following pluripotent stem cell markers were used: rat anti-human stage-specific embryonic antigen (SSEA3, Millipore, Billerica, MA), mouse anti-human octamer-binding transcription factor 3 and 4 (Oct3/4, Santa Cruz Biotech, Santa Cruz, CA), rabbit anti-human Nanog (Millipore, Billerica, MA), rabbit anti-human SRY-box 2 (Sox2, Millipore, Billerica, MA), and mouse anti-human TRA-1-60 (Abcam, Cambridge, MA); for mesenchymal cell lineages: rabbit anti-human preadipocyte factor 1 (Pref-1, [a.k.a. delta-like 1 homolog (drosophila), DLK1] preadipocyte marker, Santa Cruz Biotech, Santa Cruz, CA); mouse anti-human myosin D (MyoD, myocyte marker, R&D Systems, Minneapolis, MN), and mouse anti-human smooth muscle actin (SMA, myocyte marker, Thermo Scientific, Waltham MA); for endodermal cell lineages: mouse anti-human pan keratin (Santa Cruz, CA); rabbit anti-human α-fetoprotein (Dako, Santa Clara, CA); and mouse anti-human cytokeratin 7 (Millipore, Billerica, MA); and for ectodermal cell lineages: mouse anti-human neuron specific enolase (NSE, Millipore, Billerica, MA); rabbit anti-human glutamate receptor (Abcam, Cambridge, MA); rabbit anti-human NeuroD (Chemicon, Temecula CA); mouse anti-human nestin (Chemicon, Temecula CA); and rabbit anti-human microtubule-associated protein 2 (MAP2, AbDSerotech, Raleigh, NC). All primary antibodies were diluted 1:200 in PBS/0.1% BSA solution. Following treatment with primary antibodies, cells were washed 3 times with PBS and incubated for 1 hour at R/T with PBS/0.1% BSA containing secondary immunofluorescent antibodies (1:1000) Alexa Fluor 488 conjugated dye (mouse or rat, Invitrogen, Carlsbad, CA) or Texas Red conjugated dye (rabbit, Invitrogen, Carlsbad, CA). Cells were washed 4× with PBS and treated with PBS/0.2% DAPI for 10 minutes. Cells were then washed 3× with PBS. Images were acquired with an Evos immunofluorescence inverted microscope (Advanced Microscopy, Mill Creek, WA).

Results

I— PASCs Isolation from Lipoaspirated Human Adipose Tissue

Adipose tissue is composed of adipocytes (mature cells) and the stromal vascular fraction (SVF) containing a heterogeneous population of cells, including adipose tissue macrophages (ATMs), adipose stem cells (ASCs), mesenchymal stem cells, and fibroblasts (24-25). Isolated PASCs were activated from their quiescent state by exposing them to cellular stress (FIG. 4-5).

For this, lipoaspirate material was first incubated in collagenase for 30 min at 37° C. to release adipocytes (floating cells) and different cellular components present in the SVF as previously described (25). This material was then subjected to severe cellular stress, including long incubation with collagenase, low temperatures, low serum and hypoxia all cells die under these conditions, except PASCs because of their high resistance to cellular stress.

Optimal conditions for the release of PASCs were determined to be 6-8 hours incubation with collagenase in DMEM medium without FCS at 4° C. under very low 02, which subsequently gave way to a homogenous population of PASCs. This high purity is presumably due to the severity of the cellular stress conditions, responsible for the depletion of other cell types. As all other components of the adipose tissue lipoaspirate failed to survive, a population of highly purified PASCs was obtained, and therefore further purification processes were not necessary.

PASCs were plated in both adherent and non-adherent cell culture dishes. It was observed that PASCs can grow either in suspension or in adherence culture to form the characteristic cell clusters observed in ES cell-derived embryoid body, as described in bone marrow and dermal fibroblast-derived Muse cells in previous reports (FIG. 5) (22-23). Under both conditions, individual PASCs reached a diameter of around 10 μm and cell clusters reached a diameter of up to 50-100 μm by day 1 without major changes in the number of isolated cells and cluster cells (FIG. 7), confirming previous data of the limited of proliferative capacity of Muse cells (22).

II—PASCs have the Capacity of Self Renewal and Clonal Expansion

PASCs have the capacity for self renewal least for 8 different passages. Cell clusters spheres are formed after few hours of plating PASCs in non-adherent dish (1$^{st}$ generation). Once, most of cell spheres reached a size >50 μm, cell clusters were disaggregated by pipetting and transfer to a new non-adherent dish (2$^{nd}$ generation). PASCs were grown forming new cell-clusters as before with a growth rate of 1½ days/cell division (3$^{rd}$ generation). This indicates that PASCs have a very slow growth rate (FIG. 7)

III—PASCs have Normal Karyotype

The karyotypes of all expanded cells were normal without showing any chromosomal abnormalities. The 23 pair of chromosomes have shown normal integrity including the sex chromosomes XX (female donor) (FIG. 8)

IV—Characterization of PASCs by Fluorocytometry Analysis

Specific antibodies for SSEA3, a cell-surface glycosphingolipid frequently used to detect human ES cells and to purify Muse cells from bone marrow and dermis (61) and CD105, a classical marker of mesenchymal stem cells (43) was used for the FACS analysis. Approximately 40-50% of PASCs were positive for both markers. Interestingly, Muse cells (another pluripotent stem cells resistant to cellular stress) isolated by cell sorting were 100% positive for both SSEA3 and CD105 antibodies (22-23).

10-20% of PASCs were recognized by CD90 (marker for thymocytes), CD73 (marker for lymphocyte differentiation), CD34 (marker for hematopoietic stem cells), CD45 (marker for hematopoietic stem cells), CD44 (marker for activated T lymphocytes), HLA-DR (marker for HLA class II). In contrast, 40-60% of PASCs were recognized by CD105 (marker for mesenchymal stem cells), 60-70% by CD29 (marker for T cells) and HLA-ABC (marker for HLA class I) (FIG. 9A-B). These results confirm that PASCs have the potential to be used in cell therapy for allotransplantation. Interestingly, Muse cells derived from bone marrow and skin cells have different phenotype characteristics than PASCs. For example, Muse cells are not recognized by CD34 and CD29 while all Muse cells express SSEA3, CD105 and CD90 (22). Muse cells are isolated by cell sorting, using SSEA3/CD105 antibodies without the use of cellular stress treatment (22-23). These results indicate that PASCs and Muse cells have different phenotypes and are therefore different cell types.

V—Characterization of PASCs by Immunocytochemistry

Upon transfer and adherence to chamber slides for immunofluorescent staining, both the PASCs cell clusters and individual PASCs strongly expressed all of the characteristic pluripotent stem cell markers that were examined. These included SSEA3, a cell-surface glycosphingolipid frequently used to detect human ES cells and to purify Muse cells from bone marrow and dermis (61, 22-23); Oct3/4 a protein involved in the self-renewal of human ES cells; Nanog, a transcription factor involved in the self-renewal of human ES cells; Sox2, a transcription factor that controls genes involved in embryonic development; and TRA-1-60, which reacts with the antigen TRA-1-60 on the surface of embryonic germ cells and ES cells (FIG. 10A-B). Comparatively, ADSCs derived from the same lipoaspirated tissue were either negative or weakly positive for these pluripotent stem cell markers (FIG. 10A-B).

Example 2: Differentiation of PASCs into the Three Germline Cell Lineages

Material and Methods
Immunocytochemistry

Fixed PASCs were subjected to immunocytochemistry studies to determine their germline cell origin. For endodermal cell lineages: mouse anti-human pan keratin (Santa Cruz, CA); rabbit anti-human α-fetoprotein (Dako, Santa Clara, CA); and mouse anti-human cytokeratin 7 (Millipore, Billerica, MA); and for ectodermal cell lineages: mouse anti-human neuron specific enolase (NSE, Millipore, Billerica, MA); rabbit anti-human glutamate receptor (Abcam, Cambridge, MA); rabbit anti-human NeuroD (Chemicon, Temecula CA); mouse anti-human nestin (Chemicon, Temecula CA); and rabbit anti-human microtubule-associated protein 2 (MAP2, AbDSerotech, Raleigh, NC). All primary antibodies were diluted 1:200 in PBS/0.1% BSA solution. Following treatment with primary antibodies, cells were washed 3 times with PBS and incubated for 1 hour at R/T with PBS/0.1% BSA containing secondary immunofluorescent antibodies (1:1000) Alexa Fluor 488 conjugated dye (mouse or rat, Invitrogen, Carlsbad, CA) or Texas Red conjugated dye (rabbit, Invitrogen, Carlsbad, CA). Cells were washed 4× with PBS and treated with PBS/0.2% DAPI for 10 minutes. Cells were then washed 3× with PBS. Images were acquired with an Evos immunofluorescence inverted microscope (Advanced Microscopy, Mill Creek, WA).

Induced Differentiation of PASCs

Various differentiation media were used to induce differentiation of Muse cells-AT to the three germline cell lineages.

For adipocyte formation, adherent PASCs were treated with adipogenic differentiation medium containing DMEM with 0.5 mM isobutylmethylxanthine, 1 μM dexamethasone, 10 μM insulin, 200 μM indomethacin and PPAR-γ (ZenBio, Inc, Research Triangle Park, NC) over 3 or 6 days at 37° C. and 5% CO2. Adipocytes were detected using fluorescence lipid drop marker BODIPY-C$_{16}$(1:1000, Invitrogen, Carslbad, CA) following manufacturer specification.

For myocyte formation, adherent PASCs were incubated in DMEM containing with 10% FBS, 5% NHS, 50 μM hydrocortisone, and 1% antibiotic-antimycotic solution over 3 or 6 days at 37° C. and 5% CO2. Smooth muscle cells were identified by expression of smooth muscle actin (SMA) and skeletal muscle cells myosin D.

For hepatocyte and biliary cell induction, adherent PASCs were incubated in hepatocyte differentiation medium for 3 or 6 days, as previously described adherent PASCs were incubated in DMEM supplemented with 10% FBS, 10 μg/ml insulin, 5.5 μg/ml transferring, 6.7 ng/ml sodium selenite (ITS; Gibco, Life Technologies, Grand Island, NY), 10 nM dexamethasone (Sigma-Aldrich, St. Louis, MO), 100 ng/ml hepatocyte growth factor (HGF, Peprotech, Rocky Hill, NJ) and 50 ng/ml and fibroblast growth factor-4 (FGF-4, R & D Systems, Minneapolis, MN) (62). for 3 or 6 days. Hepatocytes were identified by immunohistochemistry using cytokeratin 7 and α-fetoprotein expression (see above).

For neural cell formation, Muse cells-AT were incubated as non-adherent cells in ultra-low attachment plates (Corning Incorporated, Life Sciences, Manassas, VA) in the presence of neural differentiation medium 1 containing Neurobasal medium (Gibco, Life Technology, Grand Island, NY) supplemented with B-27 supplement serum free (Gibco, Life Technology, Grand Island, NY), 100 μg/ml kanamycin (Gibco, Life Technology, Grand Island, NY), 2 mM glutamine (Sigma-Aldrich, St. Louis, MO), 30 ng/ml bFGF (Peprotech, Rocky Hill, NJ) and 30 ng/ml EGF (Peprotech, Rocky Hill, NJ) for 7 days (63). Cells were then transferred to polystyrene culture slides (BD Biosciences, San Jose, CA) and cultured for another 7 days as adherent cells in the presence of neural differentiation medium 2 containing 1 DMEM supplemented with 2% FCS, 25 ng/ml bFGF and 25 ng/ml BDNF (Peprotech, Rocky Hill, NJ). Neural cells were identified by immunohistochemistry using nestin and MAP2 as indicated above.

Results

I—Mesodermal Differentiation of PASCs

Adipose tissue has been shown to harbor ASCs with the ability to differentiate into the mesenchymal cell lineages: adipocytes, chondrocytes, myocytes and osteoblasts [16, 20]. However, ASCs in the appropriate differentiation medium require approximately 2½ weeks to develop mature adipocytes, and myocyte differentiation, with characteristically fused nuclei, takes approximately 3 weeks (24-25).

To determine the potential of PASCs to spontaneously differentiate into cells of mesodermal lineage, PASCs were grown as adherent cells in culture medium only containing DMEM, 10% FCS+Antibiotics for 3 days. Spontaneous differentiation of PASCs into a mesodermal lineage was determined by immunocytochemistry. Mesodermal markers included DLK, a marker for preadipocytes (59), BODIPY-$C_{16}$, a fluorescent dye used to detect lipid accumulation (25, 64-65), and myosin D (Heavy Chain), a marker for the heavy chain portion of the Myosin II protein found in skeletal muscle cells (66, 67). After cultured as adherent cells for 3 days, PASCs displayed significant expression of DLK, (21±8% of all DAPI-positive cells), BODIPY-$C_{16}$ (61±13% of all DAPI-positive cells) and Myosin D (25±4% of all DAPI-positive cells), as compared to ASCs, which were slightly positive only in response to DLK (17±7% of all DAPI-positive cells) (FIG. 11A).

In the presence of adipogenic medium, demonstrated over the course of 3 and 6 days, PASCs accumulated considerable concentrations of lipid drops indicated by the formation of BODIPY-$C_{16}$ (+) droplets, which characterized 80±4% (3d) and 83±3% (6d) of all DAPI-positive cells (FIG. 11B). In contrast, ASCs showed a weak yet detectable signal for BODIPY-$C_{16}$ (+) due to the presence of lipid accumulated in the cytoplasm as a result of ASC commitment to the pre-adipocyte cell fate (FIG. 11B). At 3 days that there is a stark morphological difference between PASCs and ASCs, perhaps most apparent in the smaller size of PASCs, which is very evident in the nucleus size, as indicated by DAPI. However, this morphology is actually much more similar at day 6, at which point the nucleus size has grown significantly in PASCs, and is roughly the same as ASCs. BODIPY labeling of lipids with the intensity observed in the PASCs is typically observed in ASCs after 2-3 weeks in culture (25, 6-65). Predictably, ADSCs fully differentiated to adipocytes after 17 days of incubation in adipogenic medium (25).

In the presence of myogenic medium for 3 and 6 days, PASCs differentiated into smooth muscle cells, with the characteristic morphology of smooth muscle fibers and strong expression of SMA that characterized 77±3% (3d) and 83±4% (6d) of all DAPI-positive cells (FIG. 11C). Under the same culture conditions, ADSCs were only slightly positive after 6 days of incubation (25±4% of all DAPI-positive cells) (FIG. 10C).

Differentiation of ASCs to myocytes required ADSCs exposure to myogenic medium for at least 21 days (data not shown, (25, 66-67). These results demonstrate that while both types of adipose-derived stem/progenitor cells have the capacity to differentiate, activated PASCs differentiate towards both adipocyte and myocyte lineages much more quickly than ASCs.

II—Endodermal Differentiation of PASCs

Spontaneous differentiation of PASCs to an endodermal lineage (hepatocytes) was detected in PASCs cultured in DMEM/10% FCS for 3 days. PASCs were recognized by α-fetoprotein (19±7% of all DAPI-positive cells), which is expressed during the development of endoderm and progenitors of hepatocytes (68) and pan keratin (21±8% of all DAPI-positive cells), a marker for filaments characteristic of biliary tract epithelial cells [27] (FIG. 12A). In the cluster of cells, α-fetoprotein strongly recognized fatty acids in dimeric and trimeric forms localized in both the cytoplasm and plasma membrane of PASCs (FIG. 12A), as was previously described in human hepatoblastoma cell line HepG2 (68). In contrast, ASCs were negative for these endodermal cell markers (FIG. 12A).

PASCs previously incubated in hepatogenic differentiation medium for 3 and 6 days were positive for cytokeratin 7, an intermediate filament protein in biliary cells that characterized 69±2% (3d) and 80±7% (6d) of all DAPI-positive cells, as well as for α-fetoprotein which recognized 90±4% (3d) and 91±5% (6d) of all DAPI-positive cells (FIG. 12B), while ASCs were negative (FIG. 12B). These results demonstrate that PASCs differentiation mirrors previous studies of pluripotent stem cells differentiation to hepatocytes in terms of both time in culture (3 days) and differentiation efficiency (4-5).

III—Ectodermal Differentiation of PASCs

PASCs were cultured for 3 days in DMEM/10% FCS with antibodies characterized by ectodermal cell markers including neuron-specific enolase (NSE), a marker used to detect neocortical neuron progenitors (69-70), metabrotopic-glutamate receptor (Glut-R), a marker used to detect microglial and neural like cells (71-72) and NeuroD, a marker used to detect neocortical precursor cells. Again, PASCs showed significant expression of all these markers with 30±5% (Glut-R), and 15±5% (NeuroD) of all DAPI-positive cells (FIG. 13A), confirming their potential to spontaneously differentiate into ectodermal cells, as opposed to control ASCs (FIG. 13A).

The morphological progression of PASCs into neurons was monitored throughout the incubations in both the first and second neurogenic differential mediums (see Material and Methods) following similar protocols previously used for the differentiation of ES and iPS cells into cells of neural origin (69-73). PASCs exhibited a progression from the formation of large cell spheres with finger-like projections to long, neuron-like cells, which subsequently formed large networks (FIG. 13B) (69). PASCs cultured in suspension for 7 days in neural differentiation medium 1 (see Material and Methods) progressively form large cell clusters. Subsequent treatment as adherent cells for 7 days in neural differentiation medium 2 ((see Material and Methods) induced the formation of neuron-like cells detectable by morphology and by axon and dendrite-specific markers.

Figure 13C:
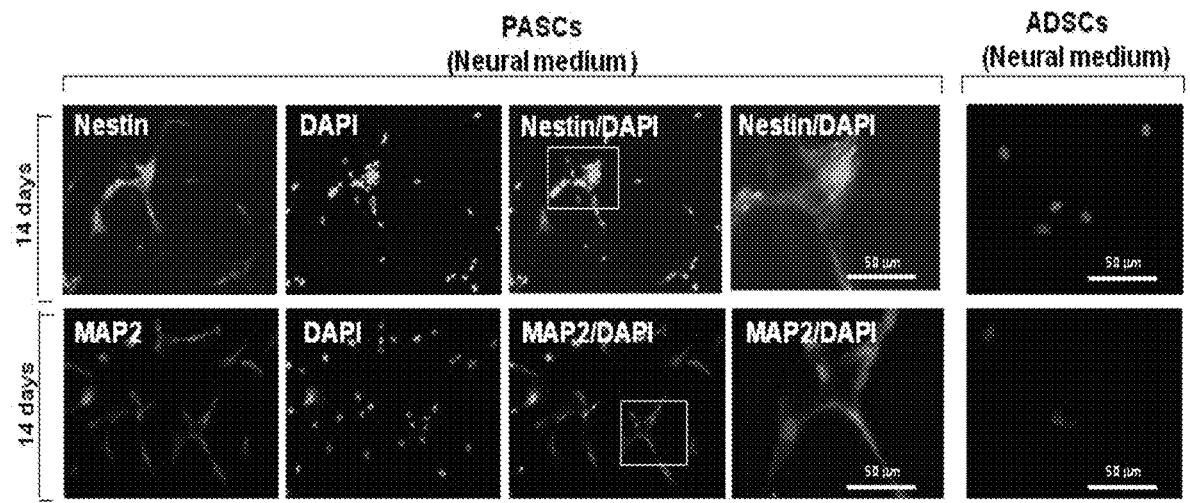
Figures 14A, 14B, 14C, 14D, 14E, 14F, 14G:
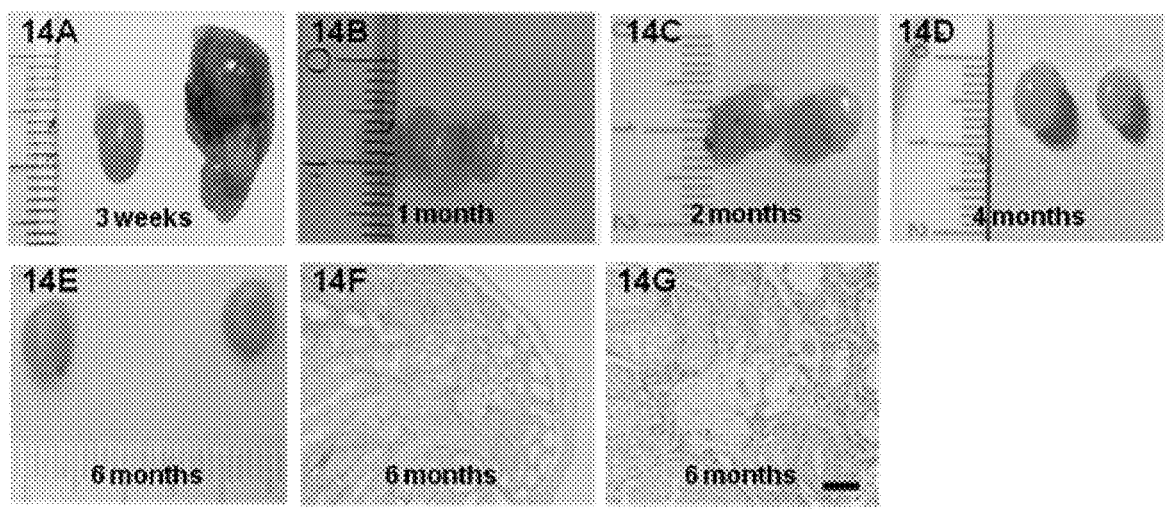
FIGS. 14A-14G show that PASCs do not produce teratomas. NODscid mice were intratesticular injected with $10^6$ PASCs for teratoma formation assay. (14A) The cell line F19 was used as positive control formed teratoma after 21 days-post injection. Muse cells did not form teratoma at (14B) 1 month, (14C) 2 months (14D) 4 months, (14E) $10^5$ PASCs injected into the testis of NODscid mice after 6 months post-injection did not form teratomas. (14F-14G) Histological studies of testis obtained from NODscid mice after 6 months post-injection ($10^5$ PASCs) shows normal testicular tissue. Arrows indicate PASCs-injected testicles. On the left, their respective controls.

Immunocytochemistry studies on PASCs having previously undergone the two-tiered neurogenic differentiation revealed expression of both nestin, a stimulant of survival, renewal and proliferation of neural progenitor cells (74). which characterized 65±11% of all DAPI-positive cells and MAP2, a protein involved in the polymerization of microtubules [43] which recognized 92±2% of all DAPI-positive cells (FIG. 13C). ASCs were negative for nestin, while MAP2 exhibited a minimal degree of non-specificity inherent to the marker (5% of all DAPI-positive cells) (FIG. 13C).

Example 3: Gene Expression of PASCs

Material and Methods
Microarray Analysis

PASCs and ASCs were isolated from lipoaspirate material of three different patients. RNA was extracted using an RNeasy Mini Kit (Qiagen) and analyzed by Hokkaido System Science Co. Ltd. Array signals were processed and normalized using the GeneSpring GX version 12.1.0 (Agilent Technologies). Data has been deposited into the Gene Expression Omnibus databank with the access number GSE46353. The criteria for selecting differentially-expressed genes were preset as at least 2-fold difference in either direction plus statistical significance (P<0.05, unpaired t test). Microarray analysis was performed using the software program IPA via a license to Ingenuity (analysis (dot) ingenuity(dot)com) to identify (1) functional pathways (cell function, physiological function, diseases), canonical signaling pathways networks of related genes derived from genes changed in the analyzed comparisons and upstream regulators. Further information regarding gene function was obtained from the program GeneDecks V3 at genecards(dot)org [20]. Statistical analyses were carried out by Fischer's exact test (as performed automatically by the software). In determining which genes are only expressed in either PASCs or ASCs, all samples, having been performed in triplicate, had to display uniform detection (indicated with at least 100 standard units) or absence (at most 30 standard units) along with a P-value <0.05.

Results

I—Gene Expression of PASCs in Comparison with ASCs

Tables S1-2 show PASCs cell gene expression in comparison with ASCs performed by microarray in RNA obtained from three different patients. Differential expression of at least a 2-fold change between Muse—AT cells versus ASCs was observed in 435 up and 434 and down-regulated genes respectively (p<0.05, Tables S1-S2). The most predominant up-regulated genes of PASCs versus ASCs included CXCL2 (777.8 fold), ESCM2 (153.2 fold) DLL1 (147.4 fold), NR4A2 (139.2 fold), ADAMTS9 (115.3 fold), BMX (91.5 fold), MYZAP (87.6 fold), ALDH1A2 (47.1 fold) and SOD2 (41.4 fold), indicating that these genes were otherwise turned off or suppressed in ASCs (Table S1). The most predominant down-regulated genes included AK5 (136.6 fold), GRE1142 (115.2 fold), CEP55 (93.6 fold), BUB1B (66.4 fold), CDCA3 (62.5 fold), NUF2 (54.8 fold) and DEPDC1 (52.7 fold) (Table S2) (26). (Each of Tables S1-S6 referenced herein can be found in Reference 26.)

Tables S1-2 also show that many of the differentially expressed genes in PASCs are highly conserved, with homologues present in numerous small organisms (yeast, S. Cerevisiae, C. elegans, chlamydomonas, T californica, drosophila, etc.). This indicates the possibility that Muse cells play a role in a highly conserved cellular mechanism related to cell survival in response to severe cellular stress (32-33).

Tables S3-4 show show genes only expressed in PASCs cell and not in ASCs. Ninety-nine genes were expressed in all PASCs samples and absent in all ASC samples. Genes expressed only in PASCs included TNFSF14 (p<0.0002), IL3RA (p<0.0007), CSF3 (p<0.0013), IL10RA (p<0.004), GATA2 (p<0.005), and BMP7 (p<0.02) (Table S3). Interestingly, PASCs expressed numerous CD-markers that ASCs did not, while no CD-markers were unique to only the ASCs (Table S4).

Tables S5 show genes only expressed in ASCs and not in PASCs. There are 41 genes expressed by ASCs that are absent in PASCs (Table S5). These genes were largely related to mitosis and cell cycling, and included ESCO2 (p<0.0007), KIF20A (p<0.0009), CENPF (p<0.0023), NEK2 (p<0.0029), RAB3B (p<0.0031), and FGF5 (p<0.0068).

14 individual genes related to DNA repair were up-regulated in PASCs vs ASCs (Table S6A). Additionally, eight ABC-cassette genes were more highly expressed in PASCs. (Table S6B). Finally, in order to examine methods of cell communication, the expression of gap junction related genes was analyzed, and it was observed that PASCs expressed three connexin genes GJA4, GJB2, GJB4, as well as C1orf71 (CNST), which encodes the recently described connexin recycling protein, consortin [44] (Table S6C).

FIG. 14 represents microarray analysis of functional group of genes expressed in PASCs and not in ASCs and vice versa. PASCs have very low expression of genes related with mitosis, cell cycle, cell proliferation, cell adhesion, DNA repair, cell survival, ubiquitination, actin remodeling, metabolism and genes activated in iPS in comparison with ASCs. For the contrary, PASCs have very high level of expression of genes related with immunity, inflammation, immune regulation, immune response, immune suppression, lymphocyte activation, T cell marker, T cell proliferation, T cell activation, co-stimulation. PASCs may regulates dendritic cells or T-helper cells at the site of an infection.

II—Gene Ontology Analysis

Gene ontology analysis was performed, and observed differential expression in PASCs correlated strongly to categories of cellular functions, the most statistically significant being: cell death and survival (p=2.04E-05 to 3.15E-02), embryonic development (p=5.92E-05 to 3.15E-02), tissue development (p=5.92E-05 to 3.15E-02), cellular assembly and organization (p=1.07E-04 to 3.15E-02), cellular function and maintenance (p=4.04E-04 to 3.15E-02), DNA replication, recombination and repair (p=1E-0.3 to 3.15E-0.2), cell cycle (p=1.12E-0.3 to 3.15E-0.2), organ development (p=1.54E-0.3 to 3.15E-0.2) and organismal survival (p=2.63E-0.3 to 2.63E-0.3) (FIG. 15, Tables S1-S2 of reference (26).

III—Canonical Pathways

The most highly expressed canonical pathways include the role of Oct4 in embryonic stem cell pluripotency (SOX2, NR6A1, BRCA1, ASH2L, POU5F1), BRCA1 in DNA damage and hereditary breast cancer signaling (POLRJ2/POLR2J3, FANCB, POLR2J, CDK6, RPA1, PIK3R2, RFC5, BIM BRCA1, RFC3), cell cycle control of chromosomal replication (MCM6, ORC3, CDK6, RPA1), DNA repair (RPA1, RFC5, RFC3), arginine degradation (ALDH4A1, OAT), and embryonic stem cell differentiation into cardiac lineages (SOX2, POU5DF1) (FIG. 17). These data provide further insight into the potential role PASCs in DNA repair, cell cycle, oxidative stress, cancer cell regulation, as well as their intrinsic pluripotency.

Up and down-regulation of critical genes involved in cell death and survival (e.g. SGK1 (up1.6×), MDH1, ATF2, HSPA8, PDL43, BRD1, CALM1, NR4A2, GATA2, CDK6, NUF2, CDK6, BRC1, BUB1B and CCXL2) could contribute to Muse-AT cell resistance to severe cellular stress exposure.

The BRC1 DNA damage and repair pathway] is down-regulated in PASCs versus ASCs, indicating the high capacity of PASCs to resist DNA damage as a result of severe cellular stress.

IV—Upstream Regulator Analysis

MicroRNA Let-7 is the most significant upstream regulator present in PASCs vs ASCs. Let-7 regulates 11 downstream genes associated with decrease of cell cycle division (e.g. CDCA3, CDC16), cell differentiation (DZIP1), cellular growth and proliferation (SSR1), DNA replication (MCM6), replication factor and cancer (RFC3, RFC5) and cell death and survival (NUF2, BRCA1, BUB1B, CDC16) (FIG. 18).

Lin28, a RNA-binding protein gene, maintains both pluripotency and tumorigenesis in ES and iPS cells. Let-7, a microRNA that regulates embryonic development, cell differentiation and tumor suppression, have the opposite effect (75). While over-expression of Let-7 blocks Lin28 gene expression, strong Lin28 expression degrades Let-7, maintaining a balance between the two reciprocally counteractive genes (75).

ES and iPS cells have a very high Lin28/Let7 ratio, which has been thought to play a major role in their tumorigenic propensities (75). In the absence of a strong Lin28 influence, Muse cells retain their pluripotent capacity (75). Over-expression of Let-7 in Muse cells would potentially play a critical role in inhibiting Lin28 expression, and therefore would protect these cells from tumorigenic proliferation and teratoma formation.

Example 4: Role of PASCs in Immune and Autoimmune Diseases

Material and Methods
Formation of PASCs after Co-Culture Between Adipocyte and the Stromal Vascular Fraction Human adipose tissue was finely minced and treated with collagenase for 60 minutes at 37° C., in the transport buffer. The cell suspension was then filtered through a pre-moistened 150-micron nylon mesh (Small Parts Inc., Miami Lakes, FL) and centrifuged for 2 min at 50×g at RT. The upper phase (floating adipocytes) was separated from lower phase (SVF). Adipocyte fraction was washed twice and diluted in adipocyte culture medium (DMEM, 1% BSA, 3% FCS, 100 U/ml Penicillin, 100 µg/ml Streptomycin). The lower phase was subjected to centrifugation for 5 minutes at 500×g. The cell pellet (SVF) was resuspended in PBS and subjected a Ficoll density gradient to further purify the SVF. The interface containing the SVF fraction was removed and washed with 5 ml of PBS at RT. After a final centrifugation for 5 minutes at 500×g, the cell pellet was resuspended in culture medium (RPMI medium supplemented with 10% FCS, 100 U/ml penicillin, 100 µg/ml streptomycin, 2 mM L-glutamine, 1% NEAA, 1% sodium pyruvate, and 10 ng/ml GM-CSF). Cells from the SVF fraction ($10^6$/ml) and adipocyte fraction ($10^6$/ml) were allowed to equilibrate separately overnight in their respective cell culture media. Coverslips were placed in each well for immunofluorescence studies. Twenty-four hours later, resuspended adipocyte fraction was added to the wells containing the SVF fraction at an approximate 1:1 ratio. The pooled cells were co-cultured for 2-24 hours at 37° C. in 5% $CO_2$. At the end of the incubation period the adipocyte fraction was resuspended and transferred by pipette and placed in another well containing 1 ml of adipocyte culture medium (see above). The remaining SFV fraction was washed five times with 1 ml PBS, and cultured for an additional two days in fresh regular medium (see above). Coverslips were then collected for immunofluorescence (see below). Adipocyte and SVF fraction were also separately cultured under the same conditions described above. Immunohistochemistry was performed using standard protocols and different markers, S-100 and DLK (Santa Cruz, CA), markers for preadipocytes; CD34 marker for hematopoietic stem cells and early formation of adipose stem cells (Zymed, San Francisco, CA) and different pluripoten stem cell markers (Nanog, SOX2, Oct3/4, see above) were used.

Effect of PASCs on Splenocytes Contain Specific CD4 (+) T Cell Epitope for Diabetes Type I Splenocytes of a NOD BDC2.5 transgenic mice were isolated using standard conditions. These splenocytes contain CD4 (+) T cells, which only recognize a specific peptide named Mimetope (Mim) whose sequence is part of chromogranin A (ChgA) (76). Splenocytes ($5\times10^5$ cells) were cultured in 24-well clusters with Mimetope for 72 hours in the presence (co-culture) or absence of PASCs ($10^3$-$10^5$ cells/well). The number of splenocytes (cell proliferation) were determined by FACS on stained carboxyfluorescein-diacetate succinimidyl ester (CFSE) splenocytes before and after incubation with Mim±PASCs. IFNγ production was determined by FACS and RIA respectively.

Effect of PASC Conditioned Medium on Splenocytes Contain Specific CD4 (+) T Cell Epitope for Diabetes Type I $10^6$ PASCs were cultured in non-adherent dishes in DMEM/10% FCS. Conditioned medium was collected after 48 hours. Splenocytes ($5\times10^5$ cells) isolated from NOD BDC2.5 transgenic mice were cultured in 24 well clusters with Mimetope for 72 hours in the presence or absence of PASC conditioned medium at different dilutions (½ to 1/500 dilutions). For splenocytes quantification, CFSE labeled splenocytes were incubated with Mim±PASC conditioned medium. CFSE dilution was analyzed by FACS to determine cell proliferation. IFNγ production was determined by RIA.

Effects of PASCs in Mice Diabetic Models (A) NODscid mice were made diabetic by multiple (45 mg/kg, four consecutive days) injections of streptozotocin (STZ). PASCs were injected ($10^6$ cells, i.p.) into diabetic (glycemia >240 mg/dl) NODscid mice once or twice (as indicated). Glycemia and body weight were determined at time zero as well as at different times post injection using standard conditions. (B) Diabetic NOD mice are a strain of mice in which spontaneous diabetes occurs. Soon after onset of hyperglycemia in the NOD mice, PASCs were injected ($10^6$ cells, i.p.). Glycemia and body weight were determined at time zero as well as at different times post injection using standard conditions. Some animals received a $2^{nd}$ injection of PASCs ($10^6$ cells, i.p.)

Results
I—Phagocytic Activity of PASCs

Formation of PASCs were detected after co-culture of adipocyte fraction (floating cells) and the stromal vascular fraction (adherent cells) (59). There is a clear interaction between preadipocytes (S-100 (+) cells) and PASCs (SSEA3 (+) cells, red). (FIG. 18A) PASCs are firmly attached to approximately a third of the preadipocytes. This attachment is apparently selective since seemingly identical preadipocyte cells are completely engulfed in PASCs. (FIG. 18B) shows a pre-adipocyte undergoing mitosis left undisturbed by PASCs while the preadipocyte directly above is engulfed by PASCs leaving only the DAPI positive nucleus uncovered. While both preadipocytes and PASCs are S-100+ and SSEA3, (FIG. 18C-a, C-b) indicate that pre-adipocytes would show positive S-100 staining with fluorescent light exposure of 1-2 seconds, with PASCs would display positive results with only a 1 millisecond exposure time. The great discrepancy in exposure strengths suggests that the PASCs express S-100 at much higher levels, or more readily allows S-100 anti-body bind to its domain. Individual PASCs were originally identified through the clear DAPI staining of their small nuclei. There phagocytosis of preadipocytes by the much smaller PASCs. The preadipocytes could clearly be seen at different stages of being devoured. Unlike macrophages that phagocytize entire cells, PASCs leave the nucleus of preadipocytes untouched, (FIG. 18A) often times resulting in preadipocyte nuclei that are left bare in culture (FIG. 18B).

II—PASCs as Antigen-Specific Immunomodulation Cells

Figures 20A, 20B, 20C, 20D, 20E:
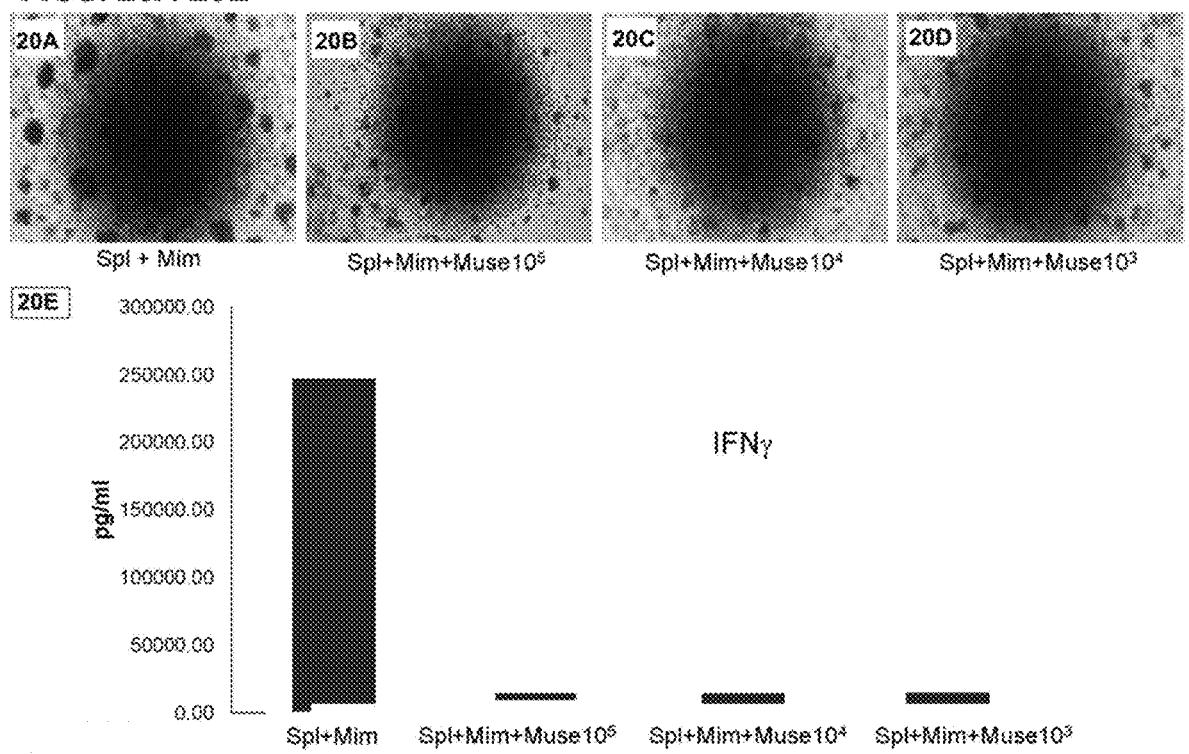
FIGS. 20A-20E illustrate the role of PASCs as antigen-specific immunomodulatory cells. Splenocytes of NOD BDC2.5 transgenic mice contain CD4 (+) T cells, which only recognize a specific peptide named Mimetope (Mim) whose sequence is part of chromogranin A (ChgA). Splenocytes ($5 \times 10^5$ cells) were cultured in 24-well clusters with Mimetope for 72 hours in the presence (co-culture) or absence of PASCs ($10^3$-$10^5$ cells/well). The number of splenocytes (cell proliferation) was determined by FACS on stained carboxyfluorescein-diacetate succinimidyl ester (CFSE) splenocytes before and after incubation with Mim±PASCs. IFNγ production was determined by FACS and RIA respectively. Co-culture of PASCs with NOD BDC2.5 transgenic mice splenocytes stimulated with Mim significantly reduced the secretion of INFγ by Ag-specific stimulated splenocytes. The histograms show dilution of CFSE in T CD3$^+$ gated cells. T cell proliferation was not affected by PASC conditioned media. (20A) NOD BDC2.5 splenocytes (spl) were stimulated with a mimotope (Mim) and culture for 72 h without and with (20B) $10^5$ PASCs, (20C) $10^4$ PASCs and (20D) $10^3$ PASCs. (20E) INFγ secretion by splenocytes stimulated with Mim was dramatically diminished by the presence of PASCs in the culture.

PASCs significantly reduced the number of BDC2.5 splenocytes stimulated by Mimetope in a dose-response manner. $10^3$-$10^4$ PASCs produced maximum inhibition in cell proliferation (FIG. 20A-D). The effect of PASCs on INFγ secretion by BDC2.5 splenocytes stimulated by Mimetope was more dramatic. $10^3$ PASCs completely inhibited INFγ levels (FIG. 20E).

Figures 21A, 21B, 21C, 21D:
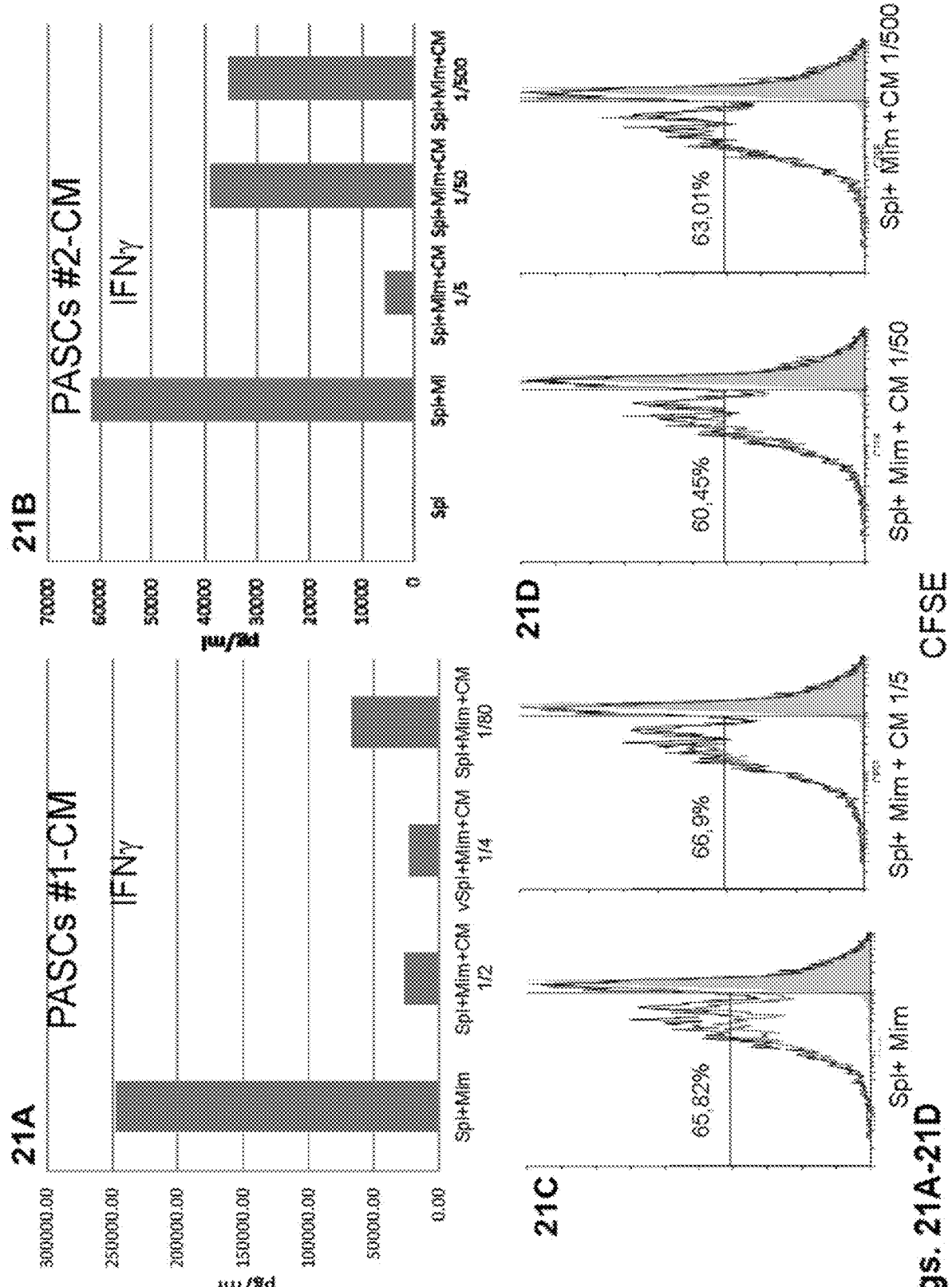
FIGS. 21A-21D illustrate that PASC conditioned medium contains factors (cytokines, growth factors, peptides) that play a critical role in antigen-specific immunomodulation. NOD BDC2.5 transgenic mice splenocytes were stimulated with a Mimetope (Mim) and cultured with several indicated dilutions of PASC conditioned media for 72 hours. PASC conditioned media significantly reduced the secretion of INFγ by Ag-specific stimulated splenocytes. An ELISA kit was used to quantify mouse INFγ. Conditioned medium of PASCs isolated from two different patients (PASC-CM #1 and PASC-CM #2) t were kept in culture for 72 hours. NOD BDC2.5 splenocytes were stained with carboxyfluorescein-diacetate succinimidyl ester (CFSE), incubated with Mim for 72 h and CFSE dilution was analyzed by FACS as measured of cell proliferation. The histograms show dilution of CFSE in T CD3$^+$ gated cells. T cell proliferation was not affected by PASC conditioned media. (21A, 21C) effects of PASC-CM #1; (21B, 21D) effects of PASC-CM #2.

PASC conditioned media significantly reduced the secretion of INFγ by Ag-specific stimulated splenocytes. PASC-CM #1 and #2 obtained from PASCs isolated from two different patients showed similar results at ⅕ dilution (FIG. 21A-B). However, T cell proliferation was not affected by both PASC conditioned media (FIG. 21C-D).

II—Effects of PASCs in Mice Diabetic Models

Figure 22A:
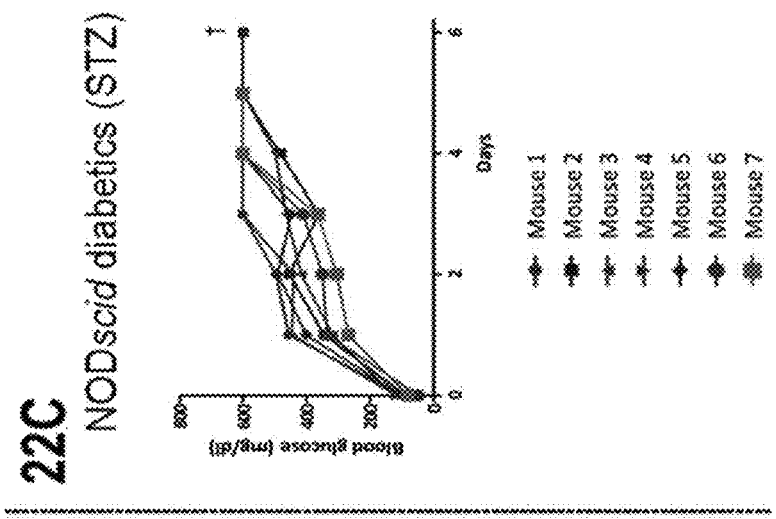
FIGS. 22A-22C show the effect of PASCs in a diabetic mouse model. (22A) NODscid mice were made diabetics by multiple (45 mg/kg, four consecutive days) injections of streptozotocin (STZ). PASCs were injected ($10^6$ cells, i.p.) into diabetic (glycemia >240 mg/dl) NODscid mice once or twice (as indicated). Glycemia and body weight were registered once a week. (22A) Most of PASCs-treated mice survived for a prolonged period maintaining an increase in body weight gain until nearly 6 weeks. Six out of seven mice survived 8 weeks-post treatment and five out of seven, reached week-11 post-treatment. (22B) Most of the PASCs-treated mice maintained oscillating glycemia below 500 mg/dl at least during 6-weeks post-treatment. (22C) All diabetic NODscid mice receiving PBS (control group) had glycemia ≥500 mg/dl by day 5 and, died or were moribund at day 6 after first injection.
Figure 22B:
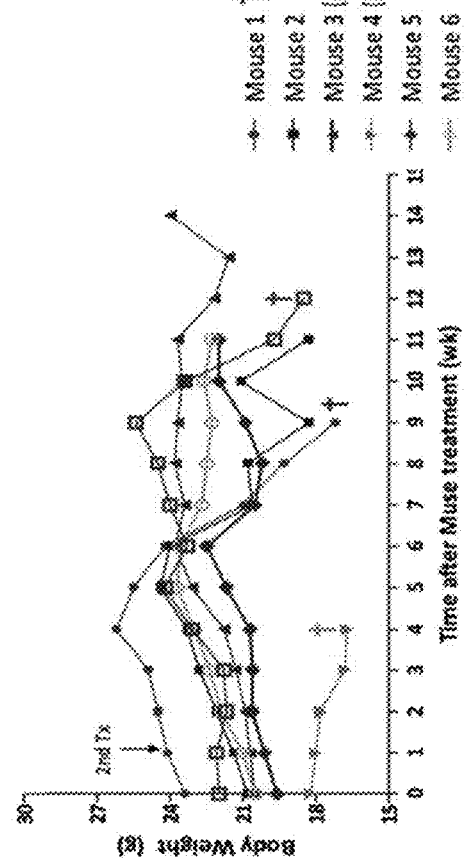
Figure 22C:
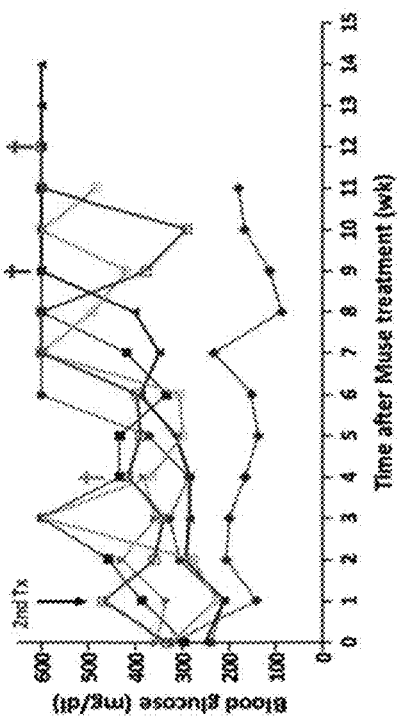

The effects of PASCs were first analyzed in a NODscid mice in which diabetes was induced by multiple injections of streptozotocin. All diabetic NODscid mice receiving PBS (control group) had glycemia ≥500 mg/dl by day 5 and, died or were moribund at day 6 after first injection (FIG. 22C). In contrast, most of PASCs-treated mice effects ($10^6$ cells, i.p.) survived for prolonged period maintaining an increase in body weight gain almost until 6 weeks (FIG. 22A). Six out of seven mice survived 8 weeks-post transplant and five out of seven, reached week-11 post-treatment (FIG. 22A). Most of the PASCs treated mice maintained oscillating glycemia below 500 mg/dl at least during 6-weeks post-treatment (FIG. 22B). These results clearly indicate that PASCs dramatically improved the loss of weight and glucose levels at least after 6 weeks of treatment. It is likely that these effects are related with the capacity of PASCs to regenerate new pancreatic and kidney cells in the diabetic animal model.

Figures 23A, 23B, 23C:
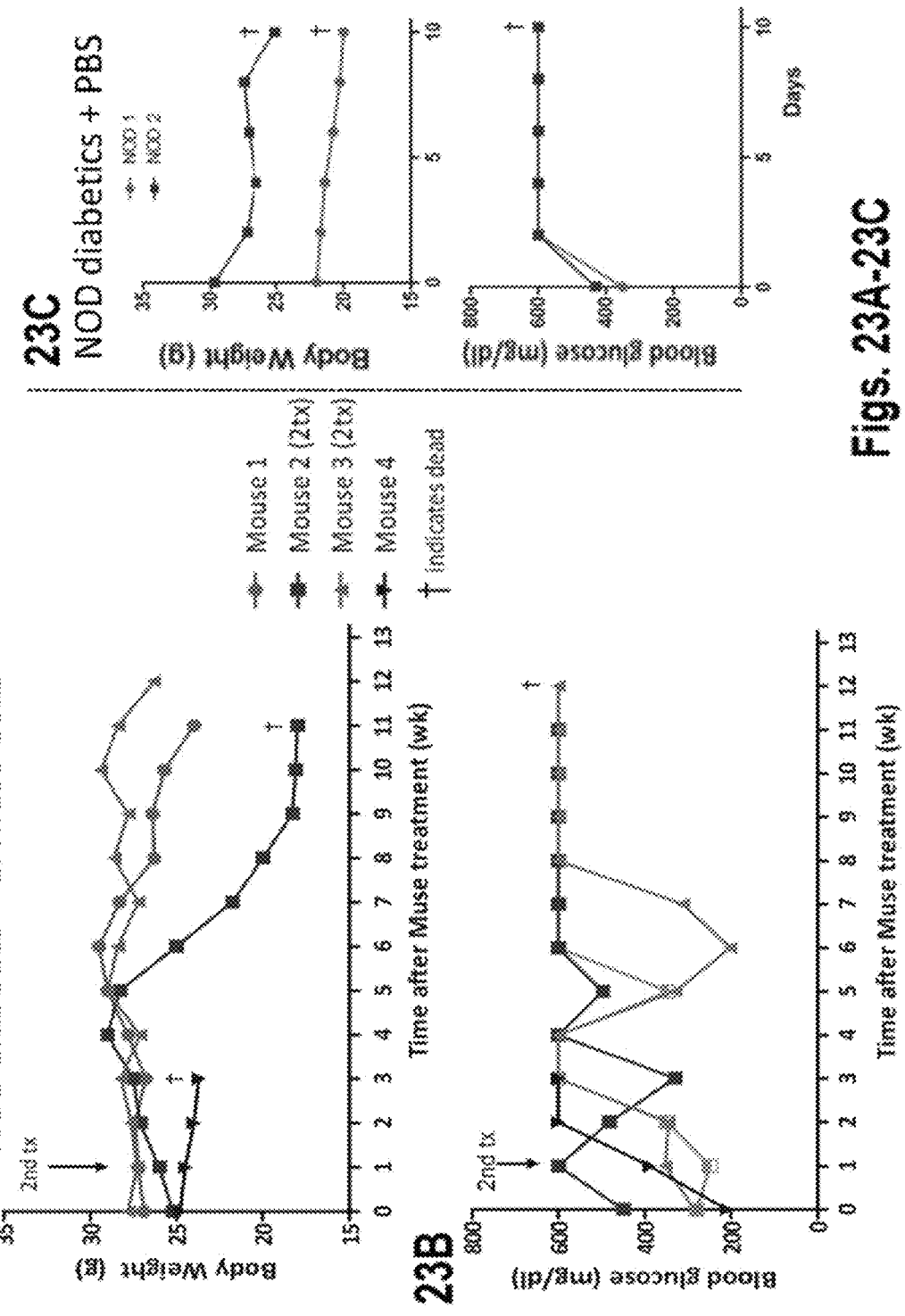
FIGS. 23A-23C show the effect of PASCs in a naturally occurring diabetic NOD mouse model. Soon after the onset of hyperglycemia, PASCs were injected ($10^6$ cells, i.p.) into NOD mice. (23A) Three out of four PASCs-injected NOD diabetic mice showed an increase in body weight gain until 5-weeks post-treatment. (23B) Blood glucose showed oscillating levels with a marked delay to reach ≥500 mg/dl during a prolonged period. (23C) All diabetic NOD mice receiving PBS (control group) reached blood glucose levels ≥500 mg/dl (day 4) with constant loss of body weight. At day 10, NOD diabetic mice died (n=2). These results indicate that PASCs-treated mice survived for prolonged periods and exhibited a significantly higher survival rate than controls.

The effects of PASCs were also analyzed in naturally occurring diabetes NOD mice. Soon after onset of hyperglycemia, NOD mice reached blood glucose levels ≥500 mg/dl (day 4) with constant lost of body weight. At day 10, NOD diabetic mice died (n=2) (FIG. 23C). Contrary, three out of four Muse cells-injected NOD diabetic mice showed an increase in body weight gain until 5-weeks post-treatment (FIG. 23A). Blood glucose showed oscillating levels with a marked delay to reach ≥500 mg/dl during a prolonged period (FIG. 23B). Undoubtedly, the transplanted diabetic mice had higher survival than controls. These results clearly indicate that PASCs dramatically improved the loss of weight and glucose levels at least after 6 weeks of treatment. It is likely that these effects are related with the capacity of PASCs to regenerate new pancreatic and kidney cells in the NOD mice.

REFERENCES

1. Evans M J and Kaufman M H. Nature 1981, 292:154-6.
2. Martin G R. Proc Natl Acad Sci USA 1981, 78: 7634-8.
3. Thomson J A, et al. Science 1998, 282: 1145-7.
4. Przyborski S A. Stem Cells 2005, 23:1242-50.
5. Takahashi K and Yamanaka S. Cell 2006, 126: 663-76.
6. Stadtfeld M and Hochedlinger K. Genes Dev 2010, 24: 2239-63.
7. Okita K, Yamanaka S. Philos Trans R Soc Lond B Biol Sci 2011, 1575:2198-207.
8. Budniatzky, I. Nat Rev Genet 2011, 12:253-65.
10. Gutierrez-Aranda I, et al. Stem Cells 2010, 28:1568-1570.
11. Lee A S, et al. Nat Med 2013, 19:998-1004.
12. Fong C Y, et al. J Cell Biochem 2010, 111:769-81.
13. Kim, K, et al. Nature, 2010, 467:285-290.
14. Trosko J E. Stem Cell Rev 2008, 4:81-8.
15. Trosko J E. Anat Rec (Hoboken) 2014, 297:161-73.
16. Kim D, et al. Cell Stem Cell 2009, 4:472-6.
17. Yu J, et al. Science 2009, 324: 797-801.
18. Jiang Y, et al. Nature 2002, 418:41-9.
19. Dimomeletis I, et al. Exp Hematol 2010, 38:1105-14.
20. Kucia M, et al. Expert Opin Biol Ther 2007, 7:1499-514.
21. Obokata, H, et al. Nature 2014, 505: 641-47
22. Kuroda Y, et al. Proc Natl Acad Sci USA 2010, 107:8639-43.
23. Wakao S, et al. Proc Natl Acad Sci USA 2011, 108:9875-80.
24. Gimble J M, et al. Circ Res 2007, 100:1249-1260.
25. Zuk P A, et al. Mol Biol Cell 2002, 13:4279-4295.
26. Heneidi S, et al. PLoS One 2013, 8:e6475224.
27. Vasiliou V, Nebert D W. Hum Genomics 2005, 2:138-143.
28. Fukai T, et al. Antioxid Redox Signal. 2011; 15:1583-1606.28.
29. Huang J, et al. Circ Res 2010, 106:1753-1762.
30. Hristov M, et al. Circ Res 2007, 100:590-597.
31. Tai M H, et al. Carcinogenesis 2005, 26:495-502.
32. Kultz D. Annu Rev Physiol 2005, 67:225-57.
33. Meier P, et al. Nature 2000, 407: 796-801.
34. Blanpain C, et al. Cell 2004, 118:635-35. Li L, Bhatia R.
35. Clin Cancer Res 2011, 17:4936-41.
36. Medici D, et al. Nat Med 2010, 16:1400-1406.
37. Xiao N, J et al. Blood 2012, 119: 4898-4907.
38. Haeckel E. Anthropogenie oder Entwickelungsgeschichte des Menschen, 3rd edn. In: Engelmann W, editor. Leipzig1877, p. 144.
39. Brunt K R, et al. Can J Physiol Pharmacol 2012, 90:327-35.
40. Maehle A H 2011. Notes Rec R Soc Lond 2011, 65:359-78.
41. Majo F, et al. Nature 2008, 456:250-4.
42. Kolf C M, et al. Arthritis Res Ther 2007, 9:204.
43. Uccelli A, et al. Nat Rev Immunol 2008, 8:726-36.
44. Zuk P A, et al. Tissue Eng 2001, 7:211-28.
45. Seydoux G, et al. Cell 2006, 127:891-904.
46. Mitalipov S, Wolf D. Adv Biochem Eng Biotechnol 2009, 114:185-99.
47. Greenberg, A. S. and M. S. Obin, Am J Clin Nutr 2006, 83:461S-465S.
48. Fantuzzi, G. J Allergy Clin Immunol 2005, 115: 911-9.
49. Farmer S R. Cell Metab 2006, 4:263-273.
50. Rosen E D, MacDougald O A. Nat Rev Mol Cell Biol 2006, 7: 885-896.
51. Siersbaek R, Mandrup S. Cold Spring Harb Symp Quant Biol 2011, 76:247-255.
52. Cristancho A G, Lazar M A. Nat Rev Mol Cell Biol 2011, 12:722-734.
53. Sugihara, H., et al. Differentiation 1986, 31:42-9.
54. Sonoda, E., et al. Endocrinology 2008, 149: 4794-8.
55. Jumabay, M., et al. J Mol Cell Cardiol 2009, 47: 565-75.
56. Jumabay, M., et al. Cardiovasc Res 2010, 85:17-27.
57. Cousin, B, et al. Faseb J 1999, 13:305-12.
58. Prunet-Marcassus, B., et al. Exp Cell Res 2006, 312:727-36.
59. Chazenbalk G, et al. PLoS One 2011, 6: e17834.

60. Blanpain C, et al. Cell 2004, 118:635-48.
60. Bhang, S H, et al. Molecular Therapy 2014, 22:862-72.
61. Byrne, J. Journal of Cellular Biotechnology 2011, 1:eP3
62. Oyagi S, et al. J Hepatol 2006, 44:742-748.
63. Hermann A, et al. J Cell Sci 2004, 117:4411-4422.
64. Listenberger L L, Brown D A. Curr Protoc Cell Biol Chapter 2007, 24: Unit 24.
65. Fink T, Zachar V. Methods Mol Biol 2011, 698:243-251.
66. Di Rocco G, et al. J Cell Sci 2006, 119:2945-295
67. Beier J P, et al. Cell Biol Int 2011, 35:397-406.
68. Carlini P, et al. Biometals 2007, 20:869-878.
69. Gottlieb D I, et al. Cells Tissues Organs 1999, 165:165-172.
70. Karumbayaram S, et al. Stem Cells 2009, 27:806-811.
71. Li M, et al. Curr Biol 1998, 8:971-974.
72. Reubinoff B E, et al. Nat Biotechnol 2001, 19:1134-1140.
73. Zhang S C, et al. Nat Biotechnol 2001, 19: 1129-1133.
74. Suzuki S, et al. J Histochem Cytochem 2010, 58:721-730.
75. Thornton J E, Gregory R I. Trends Cell Biol 2012, 22:474-82.
76. Hendy G N, et al. Clinical and investigative medicine 1995, 18:47-65.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating traumatic injury or disease-associated damage in a subject, the method, comprising:
    (i) isolating pluripotent stem cells (PASCs) by a method comprising:
        (a) releasing adipose cells, including an adipocyte fraction and a stromal vascular fraction, from an adipose tissue sample using a proteolytic enzyme that breaks the peptide bonds in collagen;
        (b) co-incubating the released adipocytes and the released stromal vascular fraction for 2-36 hours, wherein 4-24 hours of said co-incubation takes place under stress conditions in a medium containing a proteolytic enzyme, in the absence of nutrients, under hypoxic conditions, and decreasing the temperature to 4° C.;
        (c) recovering viable cells following the co-incubation in step (b) by centrifuging to produce a cell pellet, removing supernatant containing adipocyte cell debris by aspiration, washing the cell pellet to remove the proteolytic enzyme, and resuspending the recovered cells in media wherein the recovered cells comprise PASCs; and
    (ii) administering a composition comprising the PASCs to the subject under conditions permitting the PASCs of the composition to divide and populate a site of tissue damage.

2. The method of claim 1, further comprising culturing the recovered cells for up to 48 hours.

3. The method of claim 1, wherein the disease-associated damage comprises damage associated with diabetes, vascular disease, infection, degenerative neurological disease, cancer, or autoimmune disease.

4. The method of claim 3, wherein the degenerative neurological disease comprises Parkinson's Disease, Alzheimer's Disease, or Huntington's Disease.

5. The method of claim 3, wherein the degenerative neurological disease is Parkinson's Disease.

6. The method of claim 1, wherein the traumatic injury comprises hypoxia, bone injury, laceration, gunshot wound, or stroke.

7. The method of claim 1, wherein the disease-associated damage comprises damage associated with infection.

8. The method of claim 1, wherein the disease-associated damage comprises damage associated with ageing.

9. The method of claim 1, wherein the adipose tissue sample of step (a) is obtained via lipoaspiration.

10. The method of claim 9, wherein the lipoaspiration is performed on the subject to whom the composition is administered.

11. The method of claim 9, wherein the composition is administered to the subject within 6 hours of the lipoaspiration.

12. The method of claim 1, wherein the composition is administered intravenously.

13. The method of claim 1, wherein the adipose tissue is allogeneic to the subject.

14. The method of claim 1, wherein the adipose tissue is autologous to the subject.

15. The method of claim 1, wherein the composition comprises 20,000,000-200,000,000 PASCs.

16. The method of claim 1, wherein the composition is at least 95% pure PASCs.

17. The method of claim 1, wherein the PASCs have been frozen and thawed prior to administration to the subject.

18. A method of treating Parkinson's disease in a subject, the method, comprising:
    (i) isolating pluripotent stem cells (PASCs) by a method comprising:
        (a) releasing adipose cells, including an adipocyte fraction and a stromal vascular fraction, from an adipose tissue sample using a proteolytic enzyme that breaks the peptide bonds in collagen;
        (b) co-incubating the released adipocytes and the released stromal vascular fraction for 2-36 hours, wherein 4-24 hours of said co-incubation takes place under stress conditions in a medium containing a proteolytic enzyme, in the absence of nutrients, under hypoxic conditions, and decreasing the temperature to 4° C.;
        (c) recovering viable cells following the co-incubation in step (b) by centrifuging to produce a cell pellet, removing supernatant containing adipocyte cell debris by aspiration, washing the cell pellet to remove the proteolytic enzyme, and resuspending the recovered cells in media wherein the recovered cells comprise PASCs; and
    (ii) administering a composition comprising the PASCs to the subject under conditions permitting the PASCs of the composition to divide and populate a site of tissue damage.

19. The method of claim 18, further comprising culturing the recovered cells for up to 48 hours.

* * * * *